US006589157B2

(12) United States Patent
Fontayne et al.

(10) Patent No.: US 6,589,157 B2
(45) Date of Patent: Jul. 8, 2003

(54) DRIVE MECHANISM FOR MEDICAL INSTRUMENT

(75) Inventors: Diego Y. Fontayne, Montebello, NY (US); Robert A. Joachim, Glen Rock, NJ (US)

(73) Assignee: Integrated Implant Systems, L.L.C., Arlington, VA (US)

( * ) Notice: Subject to any disclaimer, the term of this patent is extended or adjusted under 35 U.S.C. 154(b) by 0 days.

(21) Appl. No.: 09/858,668

(22) Filed: May 17, 2001

(65) Prior Publication Data
US 2002/0026147 A1 Feb. 28, 2002

Related U.S. Application Data
(60) Provisional application No. 60/205,053, filed on May 18, 2000.

(51) Int. Cl.[7] .......................... A61N 5/00; A61M 31/00
(52) U.S. Cl. ................................................ 600/3; 604/61
(58) Field of Search ................ 604/61, 62; 606/96, 606/130; 600/429, 439; 378/164; 623/914

(56) References Cited

U.S. PATENT DOCUMENTS

| 4,576,591 A | | 3/1986 | Kaye et al. ............... 604/62 |
|---|---|---|---|
| 4,762,515 A | | 8/1988 | Grimm .................... 604/61 |
| 4,838,265 A | * | 6/1989 | Cosman et al. ........... 378/164 |
| 5,305,203 A | * | 4/1994 | Raab ....................... 606/130 |
| 5,514,101 A | | 5/1996 | Schulz et al. ............. 604/61 |
| 6,002,859 A | * | 12/1999 | DiGioia et al. ........... 623/914 |
| 6,214,013 B1 | * | 4/2001 | Lambrecht et al. ....... 606/96 |

FOREIGN PATENT DOCUMENTS

| GB | 2 190 590 | 11/1987 |
|---|---|---|
| WO | 97 22379 | 6/1997 |

* cited by examiner

Primary Examiner—Max F. Hindenburg
Assistant Examiner—Nikita R. Veniaminov
(74) Attorney, Agent, or Firm—Heller Ehrman White and McAuliffe

(57) ABSTRACT

A medical instrument includes a drive train assembly that causes precise index movement of the medical instrument, based on an operator-selected indexing amount resulting from actuation of a pitch adjustment knob on the medical instrument. The drive train assembly also causes a stylet to move distally within the outer housing of the medical instrument, to thereby push a seed from an extended shuttle of a seed cartridge located within the medical instrument, to a distal end of a needle cannula that is coupled to a distal end of the medical instrument.

4 Claims, 79 Drawing Sheets

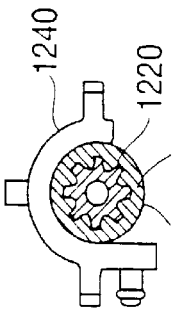
FIG. 17F
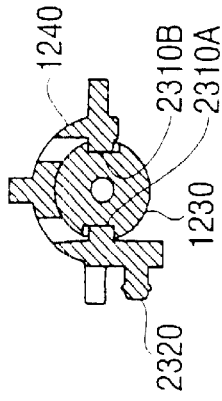
FIG. 17E
FIG. 17C
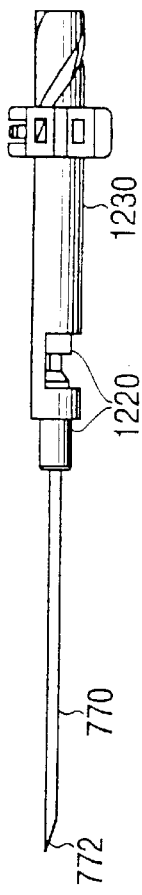
FIG. 17A
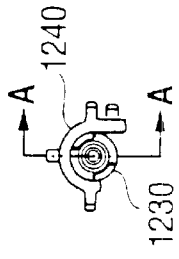
FIG. 17B
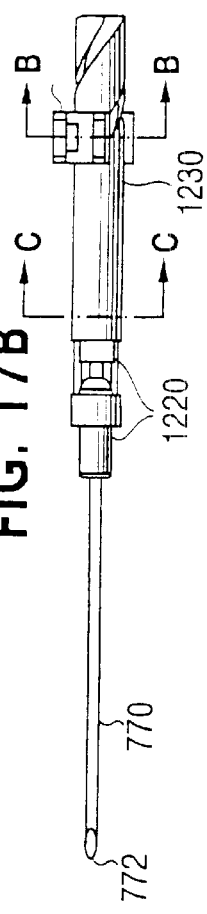
FIG. 17G
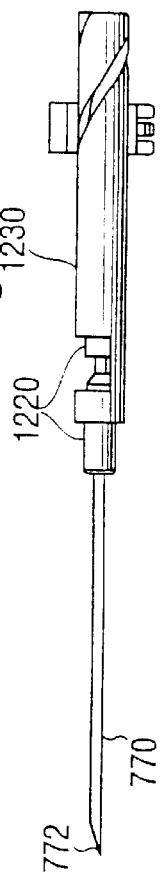
FIG. 17D
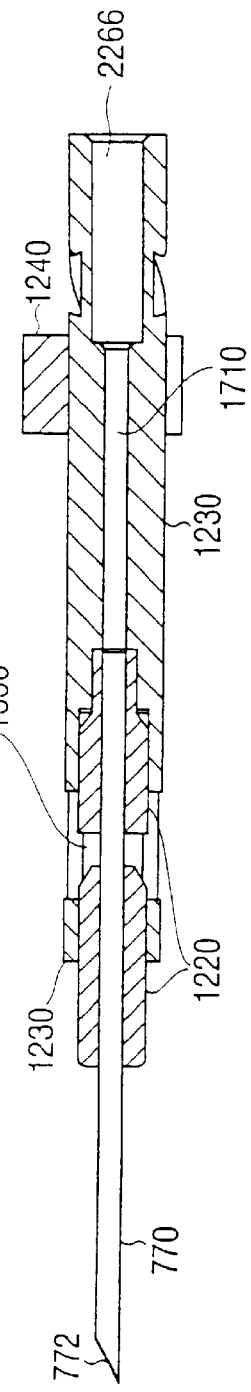

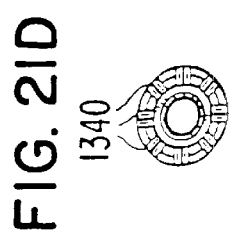
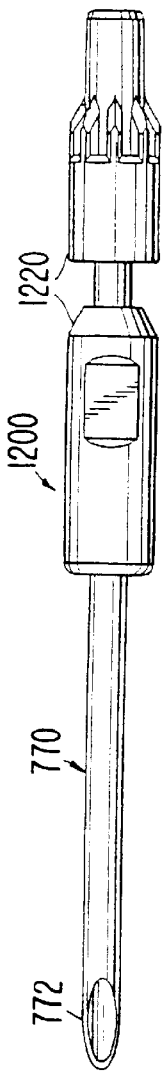
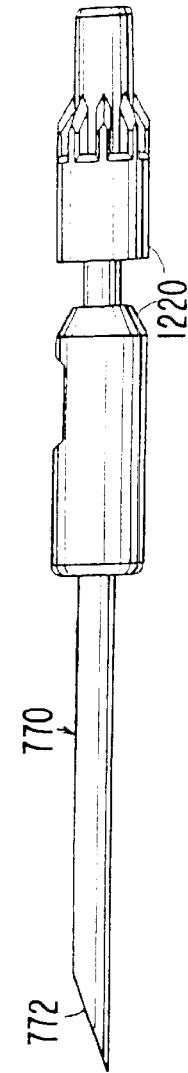
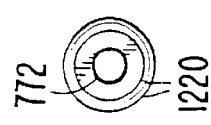
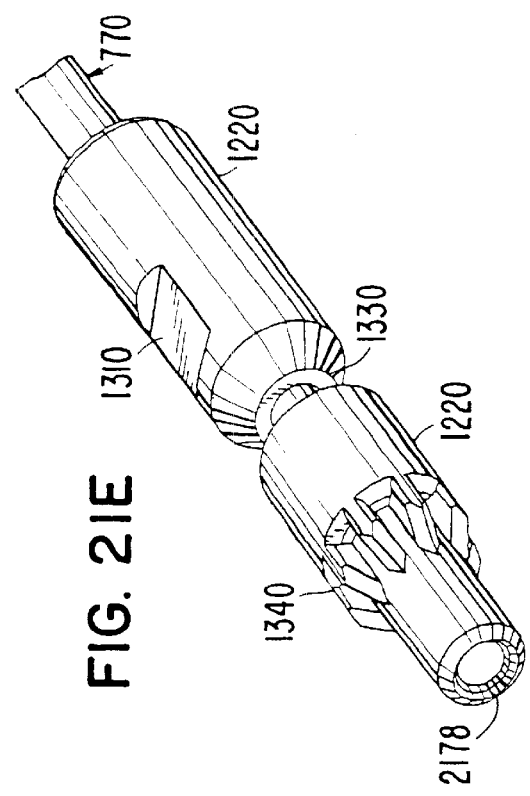

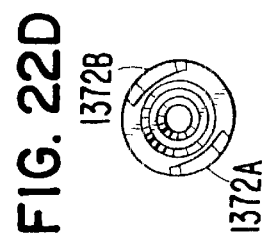
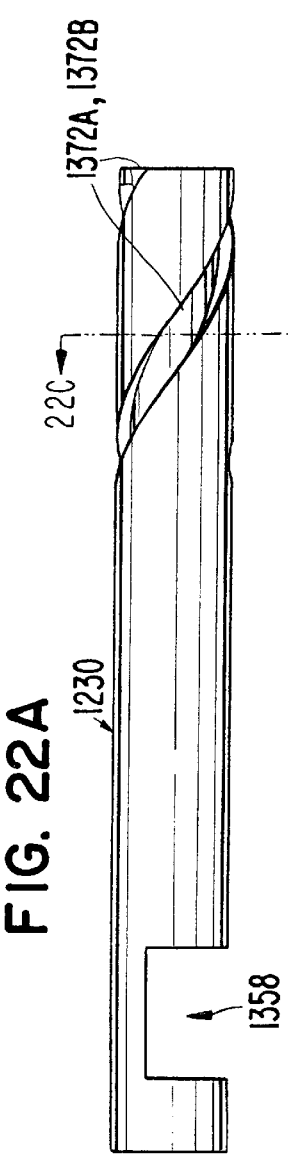
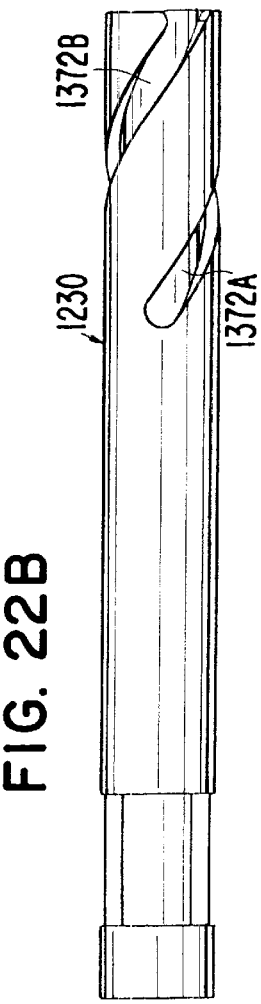
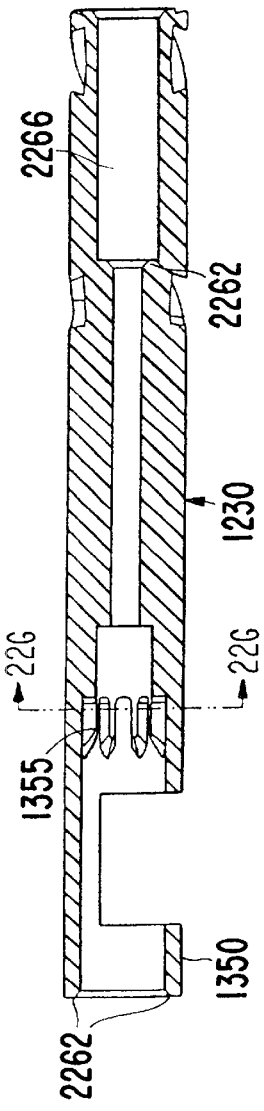
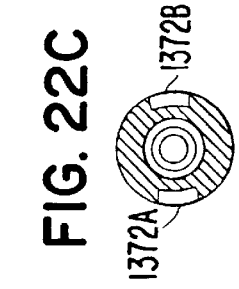
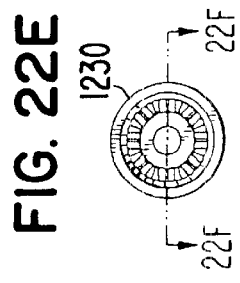

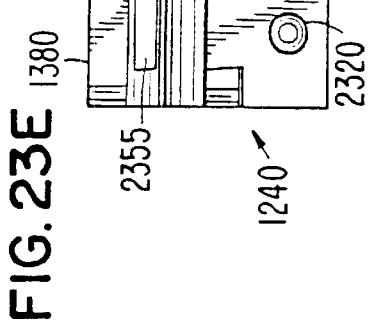
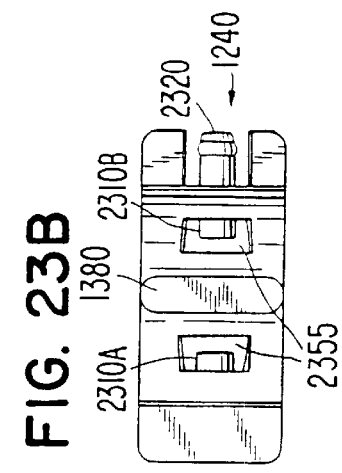
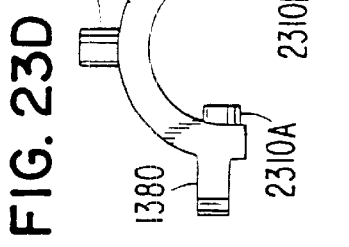
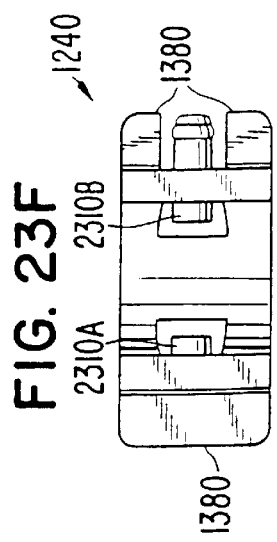
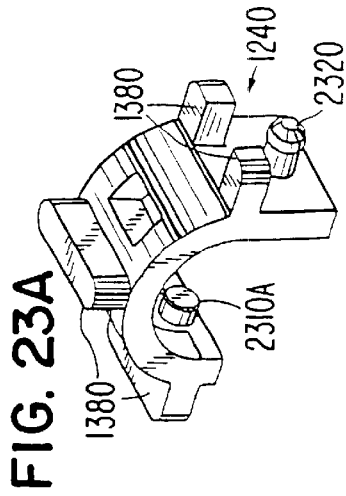
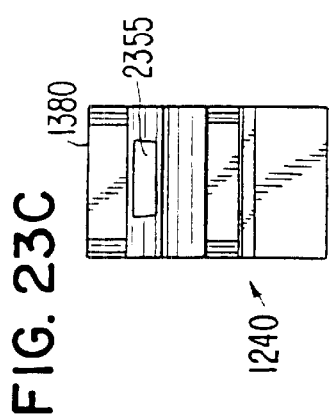

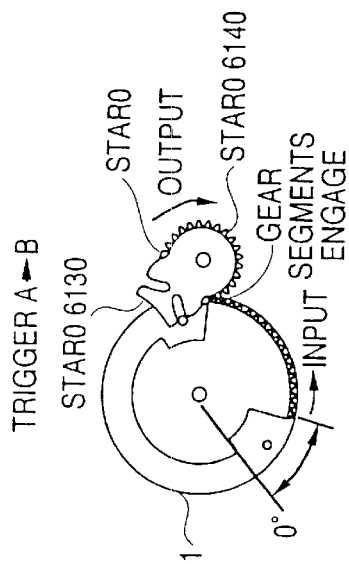
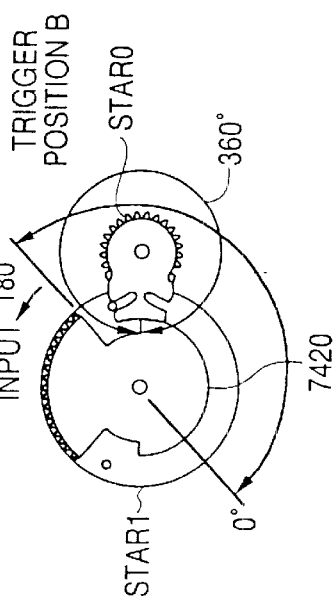
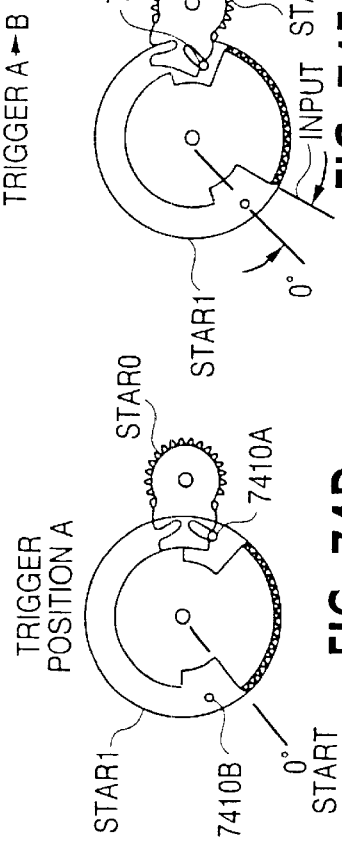
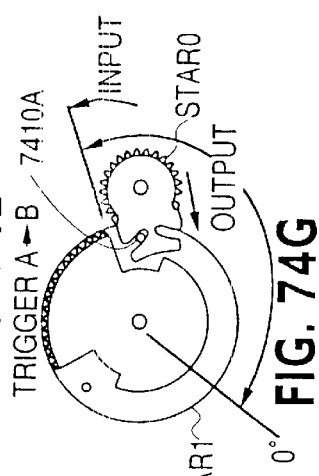
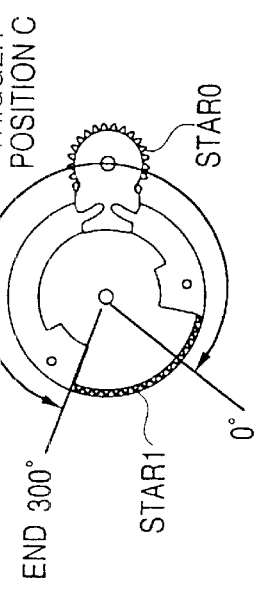
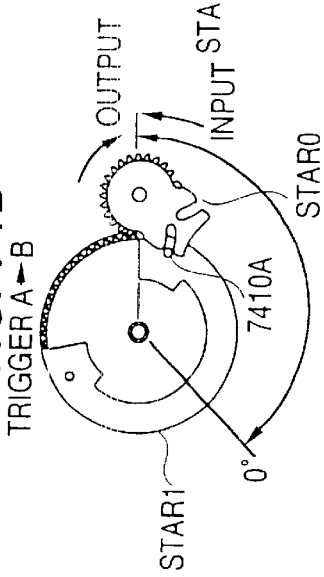

DRIVE MECHANISM FOR MEDICAL INSTRUMENT

This application claims priority to U.S. Provisional Application No. 60/205,053, filed May 18, 2000, which is incorporated in its entirety herein by reference.

BACKGROUND OF THE INVENTION

1. Field of the Invention

The present invention relates to a medical instrument used to implant seeds, such as radioactive seeds, into a patient's body. In particular, the present invention relates to a drive mechanism for a medical instrument.

2. Description of the Related Art

For treating prostate cancer, radioactive seeds are provided to various locations within a patient's prostate gland, by way of a medical instrument, also called a seed implantation device. Typically, a base unit which includes an ultrasound unit is used to determine the exact location of the patient's prostate gland with respect to the base unit. The base unit is capable of being moved either towards the patient or away from the patient.

The ultrasound unit includes a probe, which is inserted into the patient's rectum while the patient is lying on his back. A grid template is mounted onto the base unit, whereby the grid template includes a plurality of rows and columns of needle holes in which a needle can be inserted. Typically, the grid template includes a 13 by 13 matrix of needle holes, whereby adjacent holes on a row or a column are spaced 5 mm apart. Every other row is labeled with a number (e.g., 1, 2, etc.) on the grid template, and every other column is labeled with an alphabetic character (e.g., A, B, etc.). There is a direct relation between the centerline axis of the ultrasound probe and the position of the holes of the grid template.

Based on information obtained from the ultrasound unit, a needle is positioned through a particular hole (e.g., B5 hole) on the grid template, and then the needle is inserted into a region within the patient's body in which the prostate gland is located. By using the ultrasound unit, a precise position of the proximal and distal positions (relative to the ultrasound unit) of the prostate gland can be determined and recorded. The distal position (relative to the ultrasound unit) of the prostate gland is also called the "zero retraction point". Once the prostate gland position information is obtained, a seed implantation plan can be determined by a doctor, where the plan corresponds to a sequential process for injecting seeds into particular locations within the patient's prostate gland. Such treatment is generally started by placing the end of the needle (e.g., bevel end of a bevel needle or the end of a trocar needle) at the zero retraction point, and then start applying seeds with respect to that reference point.

For a conventional seed implantation device, a needle is first placed into a particular needle hole of a grid template, and then the seed implantation device is held in place by a doctor and attached to the needle. The seed implantation device is then used to inject one or more seeds into the patient's body through the needle. When finished with that hole, the seed implantation device is detached from the needle, and placed aside. Then, the needle is removed from the grid template, and a new needle is positioned at another needle hole of the grid template, according to the specific plan for treating the patient's prostate gland. Alternatively, some physicians prefer to insert an entire row of needles onto the grid template, and thereby move from needle to needle. Other physicians implant all needles required at the deepest depth position, and then continue with all needles required at the next-deepest depth position, and so forth. One conventional seed implantation device is called a MICK applicator, and requires the operator to physically reposition the MICK applicator back onto a new needle positioned onto the grid template. Such an applicator is described in U.S. Pat. No. 5,860,909, entitled Seed Applicator for Use in Radiation Therapy.

The MICK applicator is manually moved by the operator between seed implant locations. This results in inaccuracies due to the operator not being capable of precisely retracting the medical instrument to a next seed implant position, due to human error and the size and weight of the medical instrument.

SUMMARY OF THE INVENTION

The present invention includes a drive mechanism for a medical instrument, that provides for precise indexing of the medical instrument between seed implant locations.

The present invention also includes a stylet carriage assembly within a medical instrument, which includes a stylet for pushing a seed from a seed cartridge shuttle all the way to a distal end of a needle cannula that is coupled to the medical instrument.

The present invention also includes a drive mechanism for a medical instrument, which provides for needle spin movement at precise times during movement of the medical instrument between seed implant positions.

Needle spin allows trapped air to be vented, preventing vacuum or pressurization of the air. In addition, friction between the seeds and the needle are reduced by relative dynamic motion.

In one configuration, a medical instrument includes a drive assembly that provides for drive movement of the medical instrument. When a handle on the medical instrument is moved from a first home position to a second position, the drive assembly causes a carriage assembly within the medical instrument to move in a distal direction, so as to cause a stylet coupled to the carriage assembly to move in the distal direction. The stylet is in line with a seed provided within an extended shuttle of a seed cartridge also located within the medical instrument, and the stylet pushes the seed all the way to a distal end of a needle cannula that is coupled to a distal end of the medical instrument. That way, the seed is in position to be deposited within a patient.

When the handle is moved from the second position to a third, fully engaged position, the medical instrument is caused to index or move a precise amount, by way of the drive assembly. During the index movement of the medical instrument, the stylet is maintained at its fully-extended, most-distal, position. Also, during the index movement of the medical instrument, the drive assembly controls spin movement of the needle cannula, so that the needle cannula spins as it moves between seed implant positions.

As the handle is retracted from the third position to the second position, the needle cannula spins in an opposite direction, while the medical instrument remains in place (does not index). As the handle is further retracted from the second position to the first position, the stylet moves back to its most-proximal position within the medical instrument, to thereby be positioned for a next seed to be implanted at the next seed implant location within the patient.

The drive mechanism is configured to provide an assortment of internal movements within the medical instrument, such as drive carriage movement and index movement of the entire medical instrument, based on small movements of the handle.

According to one aspect of the present invention, a drive mechanism for a medical instrument includes at least one gear that causes index movement of the medical instrument in accordance with operator-actuation of a trigger on the medical instrument.

According to another aspect of the present invention, a medical instrument includes a coupling portion for coupling to a needle cannula. The medical instrument also includes a stylet that is provided within a housing of the medical instrument and that is configured to move from a rest position in which the stylet is spaced apart from the needle cannula, to an engaged position in which the stylet moves within the needle cannula, to thereby propel a seed obtained from a cartridge within the medical instrument into a distal end of the needle cannula.

According to yet another aspect of the present invention, a method for implanting at least one seed into a patient includes actuating a trigger of a medical instrument from a first position to a second position, to thereby cause a seed to be placed at a distal end of a needle coupled to the medical instrument. As a result of the actuating step, moving a stylet within the medical instrument from a first position to a second position, whereby the stylet is moved from a proximal position within the medical instrument to a distal position within the medical instrument, and whereby the stylet pushes a seed to the distal end of the needle coupled to the medical instrument as a result.

BRIEF DESCRIPTION OF THE DRAWINGS

The invention will become more fully apparent from the following detailed description when read in conjunction with the accompanying drawings with like reference numerals indicating corresponding parts throughout, and wherein:

FIGS. 17A through 17G show various views and cross sections of the needle spin assembly and needle coupling assembly, according to the present invention;

FIGS. 21A, 21B, 21C, 21D and 21E show top, side, front, back and perspective views, respectively, of the needle assembly, according to the present invention;

FIGS. 22A, 22B, 22C and 22D show side, top, front and back views, respectively, of the needle assembly according to the present invention;

FIGS. 22E, 22F and 22G show separate cross sections obtained from FIGS. 22A, 22C and 22D, according to the present invention;

FIGS. 23A through 22F show various views of the collar that is used to cause the needle assembly to spin (when the collar is disposed within slots of the needle cam and moved), according to the present invention;

FIGS. 74A–G show different engagements of gear Star-1 with gear Star-0, in accordance with trigger movement from position A to position C, according to the preferred embodiment of the invention;

DETAILED DESCRIPTION OF THE PREFERRED EMBODIMENTS

Preferred embodiments of the present invention will be described in detail hereinbelow, with reference to the drawings.

The present invention is directed to a drive mechanism for a medical instrument, more particularly, for a seed implantation device, which is configured so that it can be coupled to a targeting fixture for attachment to a needle positioned through a needle hole on a grid template. The medical instrument is also configured to receive a seed cartridge, and to remove a seed from the seed cartridge in order to provide the seed to a needle that can be attached to a front portion of the medical instrument. Details of the targeting fixture on which the medical instrument can couple to, more particularly, to a cradle unit or a sheath unit of the targeting fixture, is a subject of a first related application entitled "TARGETING FIXTURE", Provisional Application Serial No. 60/205,094, filed May 18, 2000, a second related application entitled "TARGETING FIXTURE TO A GRID TEMPLATE", Provisional Application Serial No. 60/205,054, filed May 18, 2000, and a third related application entitled "GRID SHEATH FOR MEDICAL INSTRUMENT", Provisional Application Serial No. 60/265,075, filed Jan. 31, 2001, each of which is incorporated in its entirety herein by reference. Details of the seed cartridge is a subject of a fourth related application entitled "CARTRIDGE-MOVEABLE SHIELD", Provisional Application Serial No. 60/205,055, filed May 18, 2000, which is incorporated in its entirety herein by reference. Seeds within the cartridge are capable of being examined for potency, by using a device called a well chamber holder, which is the subject of a fifth related application entitled "WELL CHAMBER HOLDER", Provisional Application Serial No. 60/205,298, filed May 19, 2000, which is incorporated in its entirety herein by reference.

Figure 10:
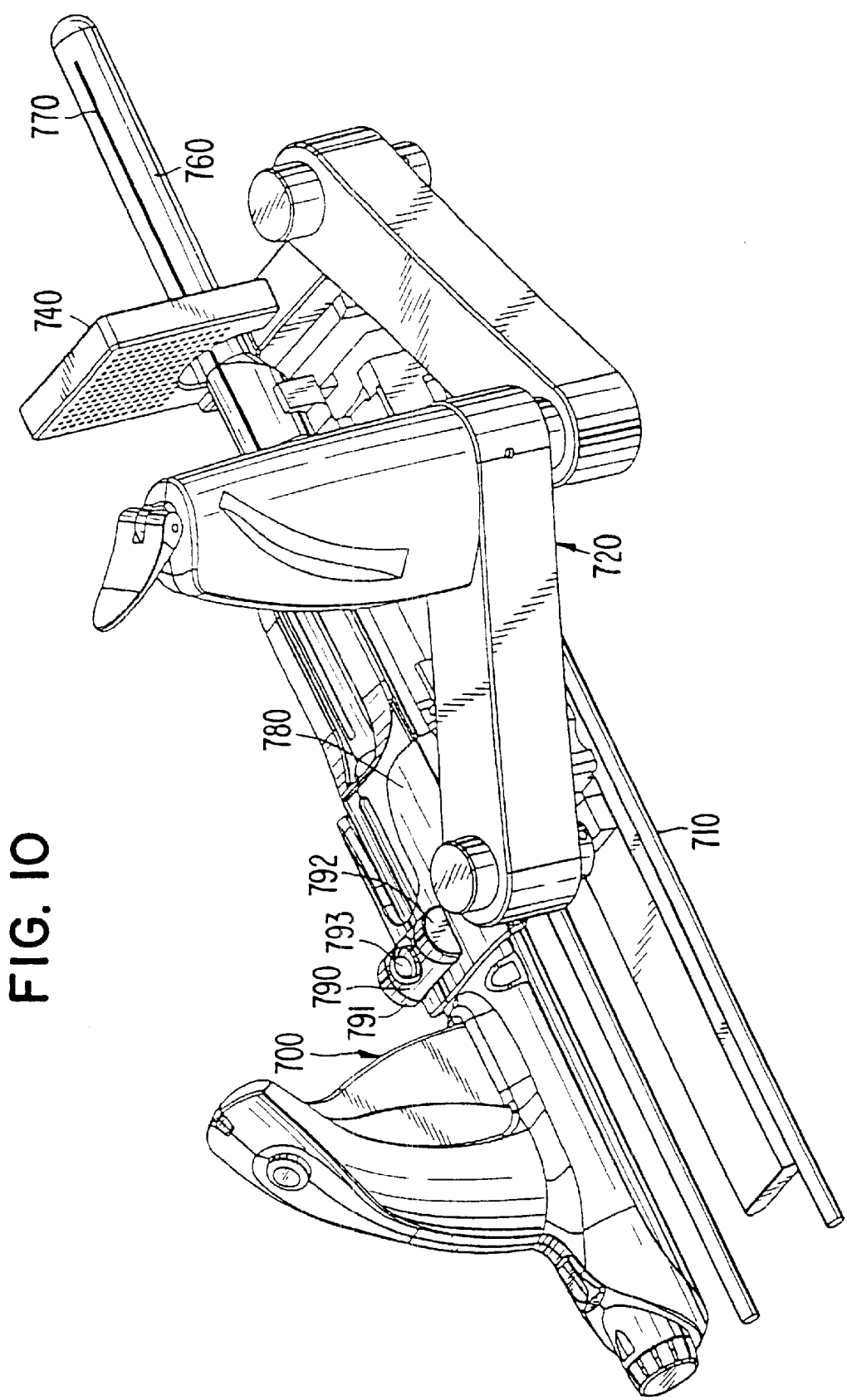
FIG. 10 shows a medical instrument in accordance with the present invention, coupled to a sheath unit of a targeting fixture.

FIG. 10 shows a medical instrument 700 in accordance with the present invention, which is coupled to a sheath unit 780 of a targeting fixture 720. The sheath unit 780 allows the medical instrument 700 to be fitted into place at a proper x,y,z location (or x,y location, depending upon which type of targeting fixture is used) with respect to a grid template 740, and also allows for the medical instrument 700 to be attached to a needle (also called a "needle cannula" hereinbelow) 770 placed into a particular hole of the grid template 740. Alternatively, the medical instrument may be coupled to a sheath unit as described in the third related application, whereby a distal end of that sheath unit is pushed against the grid template to thereby maintain the medical instrument in place (with the medical instrument coupled to the sheath unit frame) to allow for a medical procedure to take place.

Figure 1:
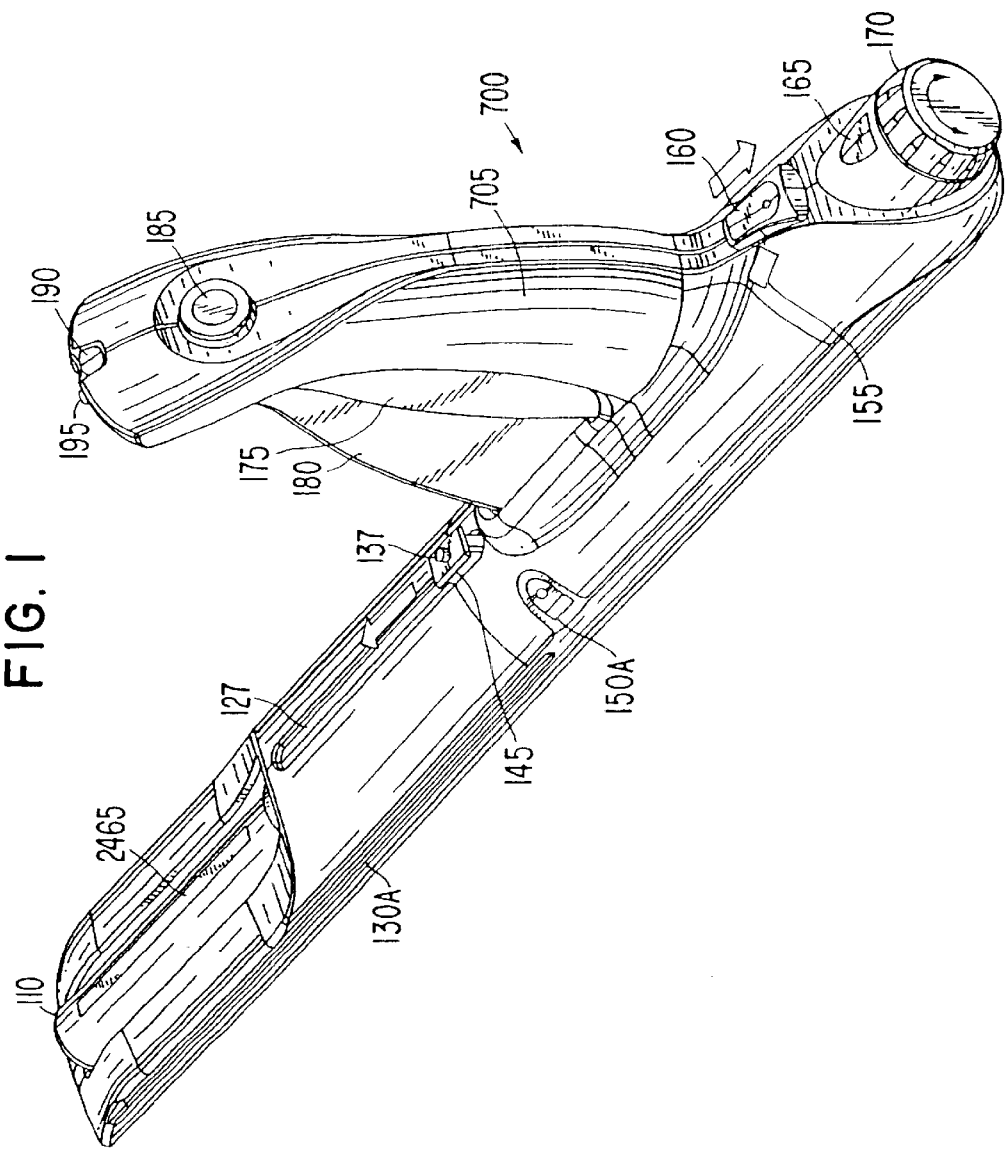
FIG. 1 shows a top perspective view of the medical instrument, which has housed within it a seed cartridge at a front portion of the medical instrument, according to the invention.
Figure 2:
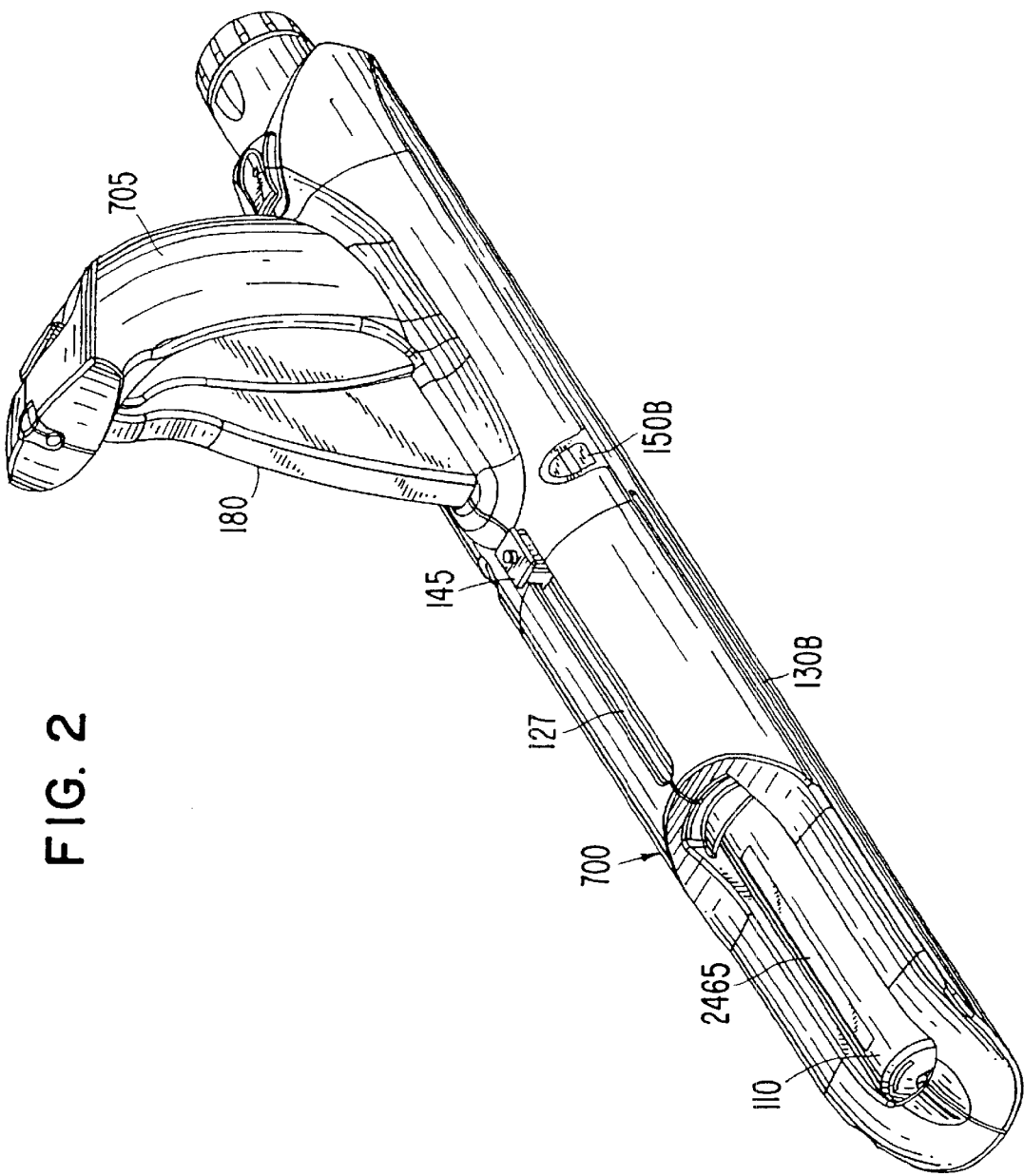
FIG. 2 shows a different top perspective view of the medical instrument, which has housed within it a seed cartridge at a front portion of the medical instrument, according to the invention.
Figure 3:
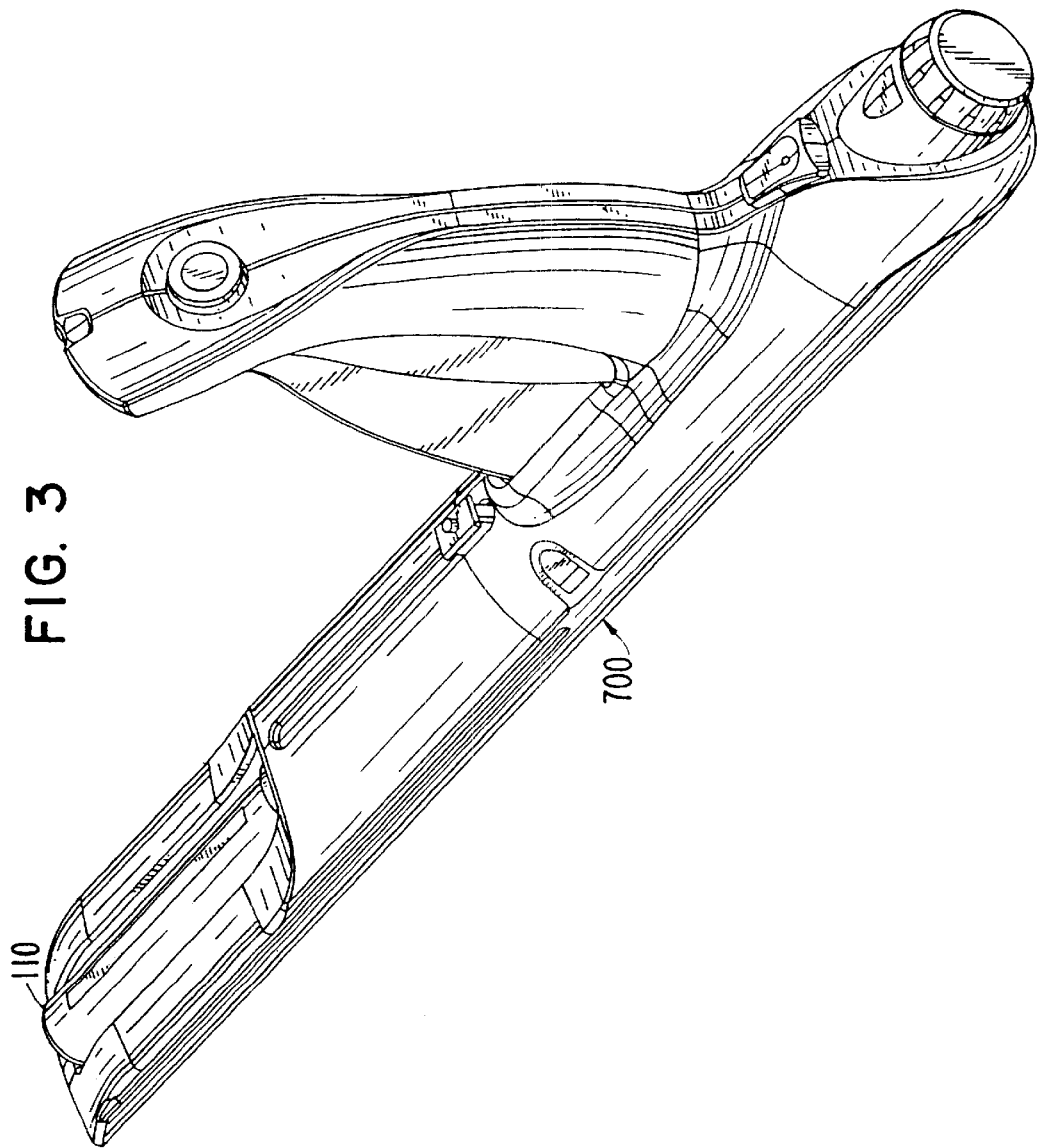
FIG. 3 shows yet another different top perspective view of the medical instrument, which has housed within it a seed cartridge at a front portion of the medical instrument, according to the invention.
Figure 4:
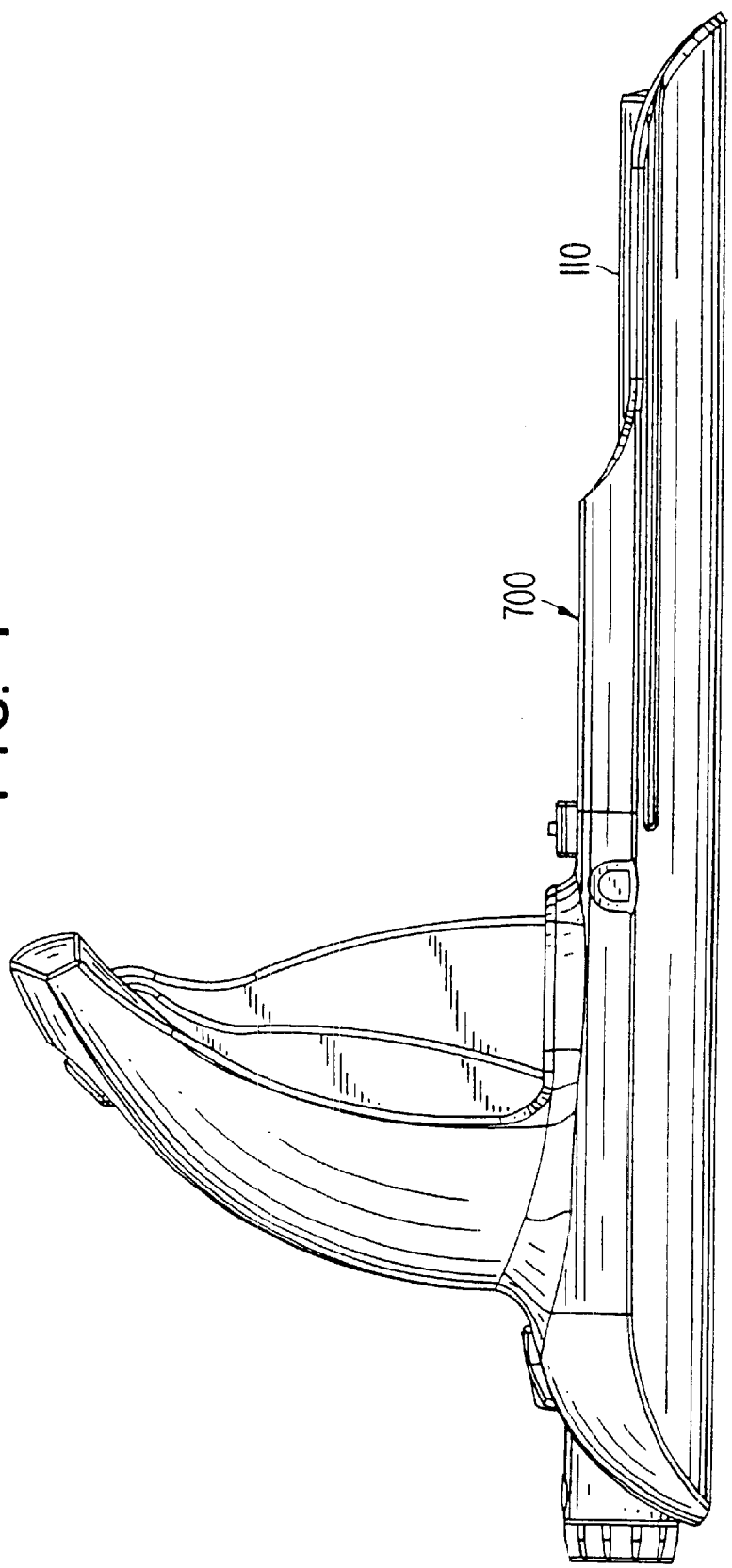
FIG. 4 shows a side view of the medical instrument, which has housed within it a seed cartridge at a front portion of the medical instrument, according to the invention.
Figure 5:
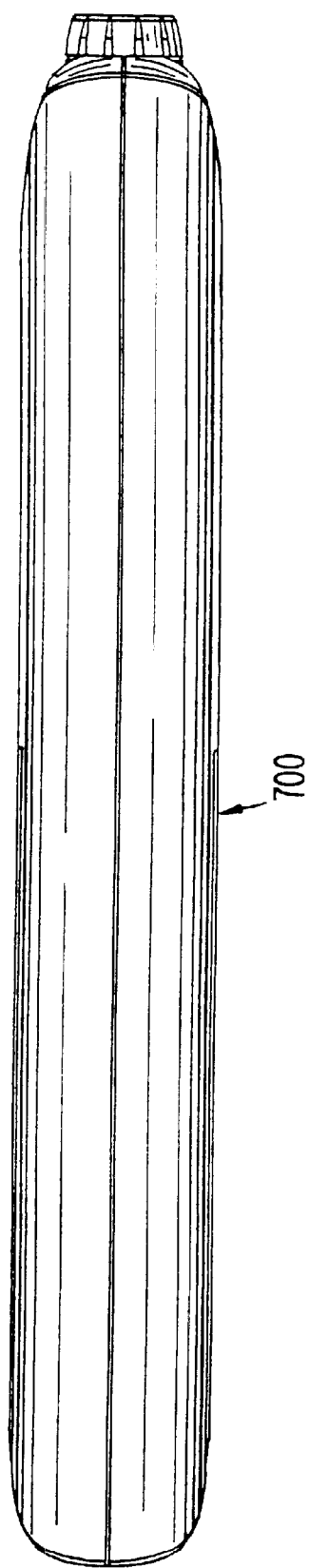
FIG. 5 shows a bottom view of the medical instrument, according to the invention.
Figure 6:
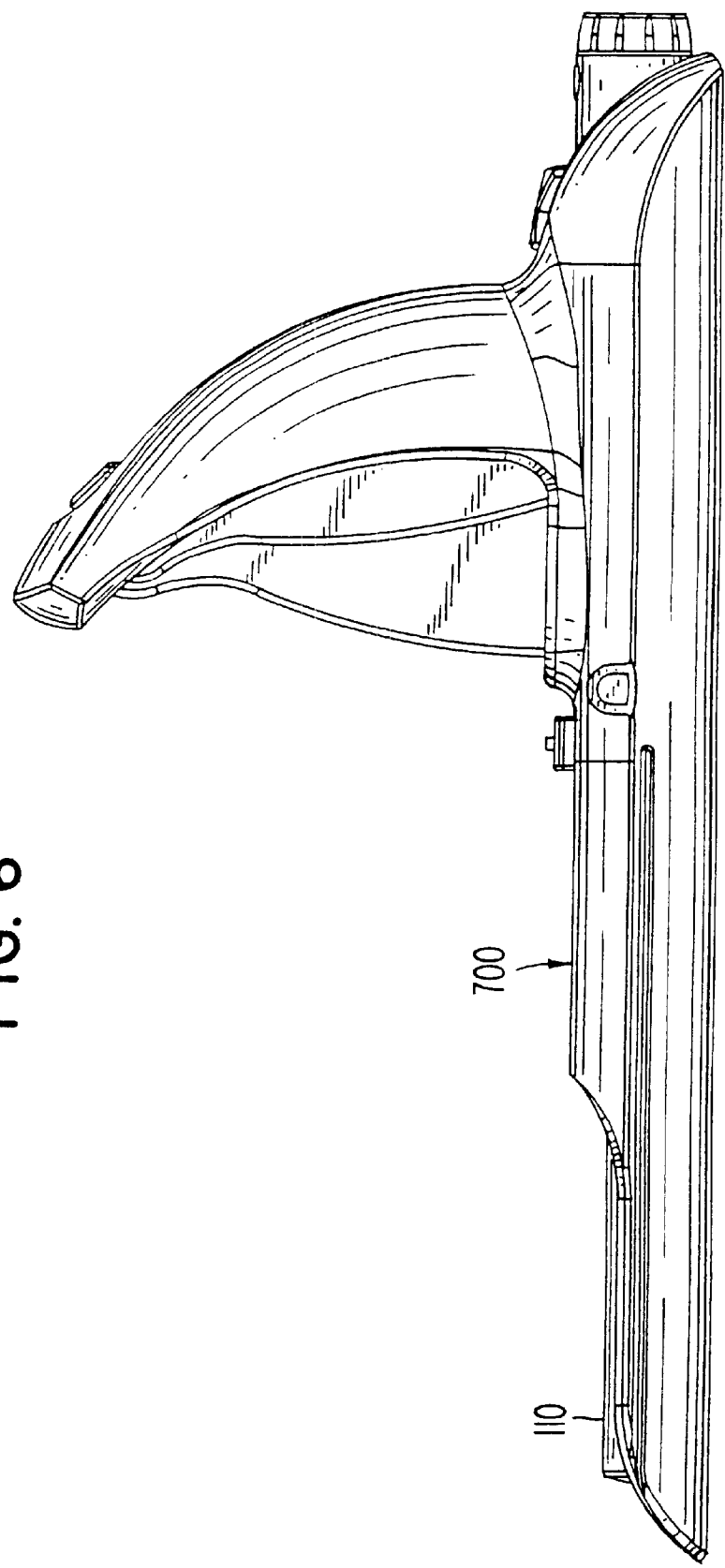
FIG. 6 shows the opposite side view, with respect to the view of FIG. 3, of the medical instrument, which has housed within it a seed cartridge at a front portion of the medical instrument, according to the invention.
Figure 7:
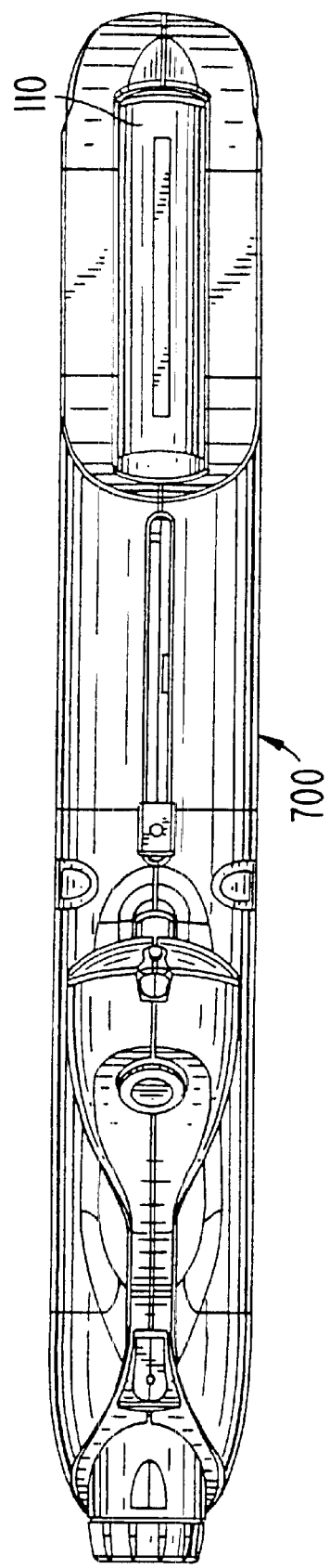
FIG. 7 shows a top view of the medical instrument, which has housed within it a seed cartridge at a front portion of the medical instrument, according to the invention.
Figure 8:
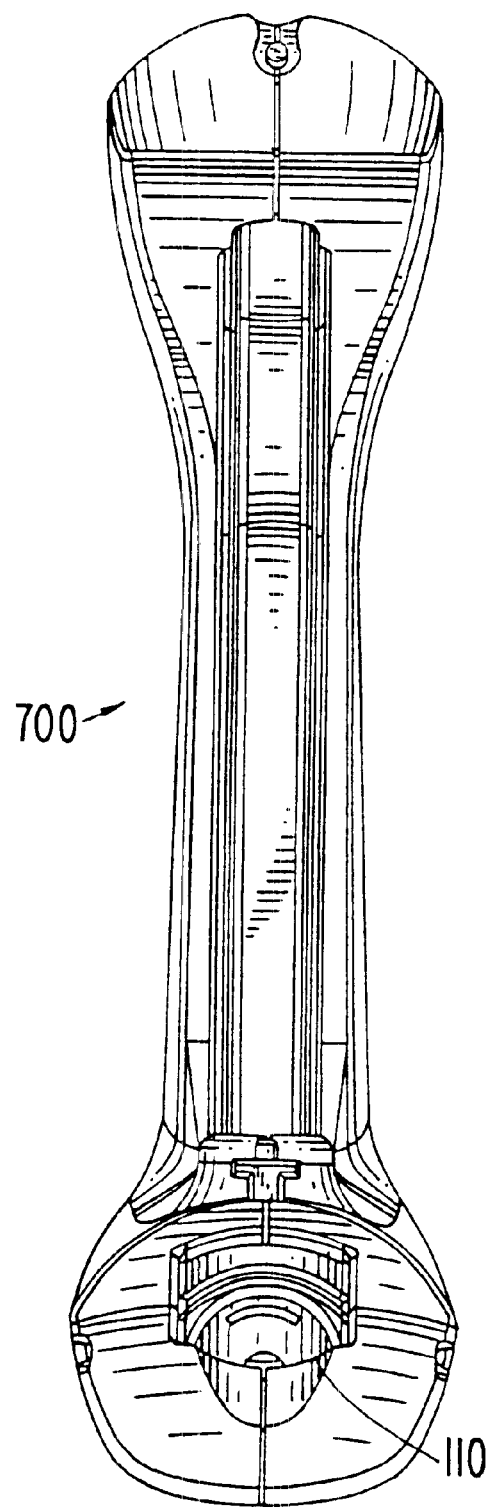
FIG. 8 shows a front view of the medical instrument, which has housed within it a seed cartridge at a front portion of the medical instrument, according to the invention.
Figure 9:
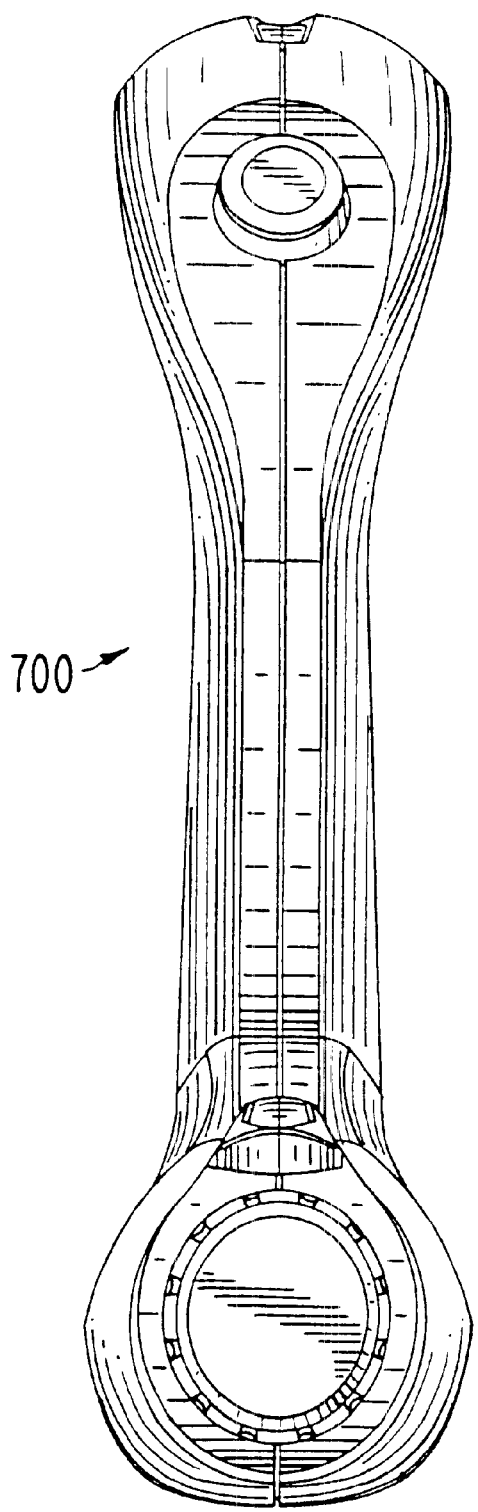
FIG. 9 shows a back view of the medical instrument, according to the invention.

Referring back to FIG. 10, the sheath unit 780 includes slots (not shown, but see the description in the first and second related applications). A key way (not shown, but see the related applications) is respectively provided in each of the slots. Each key way is preferably a lubricated plastic part, and juts out of its respective slot in order to engage with a sheath interface slot 130A, 130B provided on opposite sides of the medical instrument 700. FIGS. 1 and 2 show the slots 130A, 130B on the sides of the medical instrument 700. The key ways of the sheath unit 780 are held in place within the slots of the sheath unit 780 by way of set screws, which are screwed in via screw holes on the sheath unit 780.

Referring back to FIG. 10, the sheath unit 780 has a U-shaped opening at its top portion. The length of this U-shaped opening is preferably sized to allow an operator to discern the seed count indicator located on the cartridge. The sheath unit 780 has a cylindrical element 790 that is fitted onto its top portion. The cylindrical element 790 is fitted with first and second side buttons 791, 792 and a top button 793. The functions of these buttons will be explained later. In short, the first and second side buttons 791, 792 are simultaneously (or individually, in an alternative configuration) engaged by pushing both (or at least one, in the alternative configuration) of them inwards. This action allows a nut box interface 145 disposed on the top of the medical instrument 700 to move relative to the medical instrument 700. The nut box interface 145 can be seen in FIGS. 1 and 2. The nut box interface 145 couples to an element (not shown) on the bottom of the upper surface of the sheath unit 790, below the buttons 791, 792, 793.

When the targeting fixture 720 is placed into its proper position with respect to the grid template 740, the medical instrument 700 can be inserted and held in place within the sheath unit 780. The side slots 130A, 130B of the medical instrument 700 are fitted onto the key ways of the sheath unit 780, and the medical instrument 700 is pushed in a direction towards the grid template 740. The medical instrument 700 is locked in place when the nut box interface 145 couples to the element on the bottom of the upper surface of the sheath unit 780. In the preferred embodiment, a clicking sound is heard at that time, informing the user that the medical instrument 700 is correctly positioned within the sheath unit 780.

The medical instrument 700 is also positioned so as to be engaged with the needle 770. The precise coupling of the needle 770 to the medical instrument 700 will be described in detail in a later section. In particular, a needle hub and a needle cam will be described, each having registration ribs for coupling to each other and each being disposed within a distal frame portion of the medical instrument, to provide coupling of the needle 770 to the medical instrument 700.

When the top button 793 disposed on the cylindrical element 790 of the sheath unit 780 of FIG. 10 is pushed downwards from its normal, upwards position, the nut box interface 145 of the medical instrument 700 disengages from the sheath unit 780, thereby allowing the medical instrument 700 to be freely moved by sliding it back out of the sheath unit 780. That way, the medical instrument can be slid out of the sheath unit 780.

Figure 11:
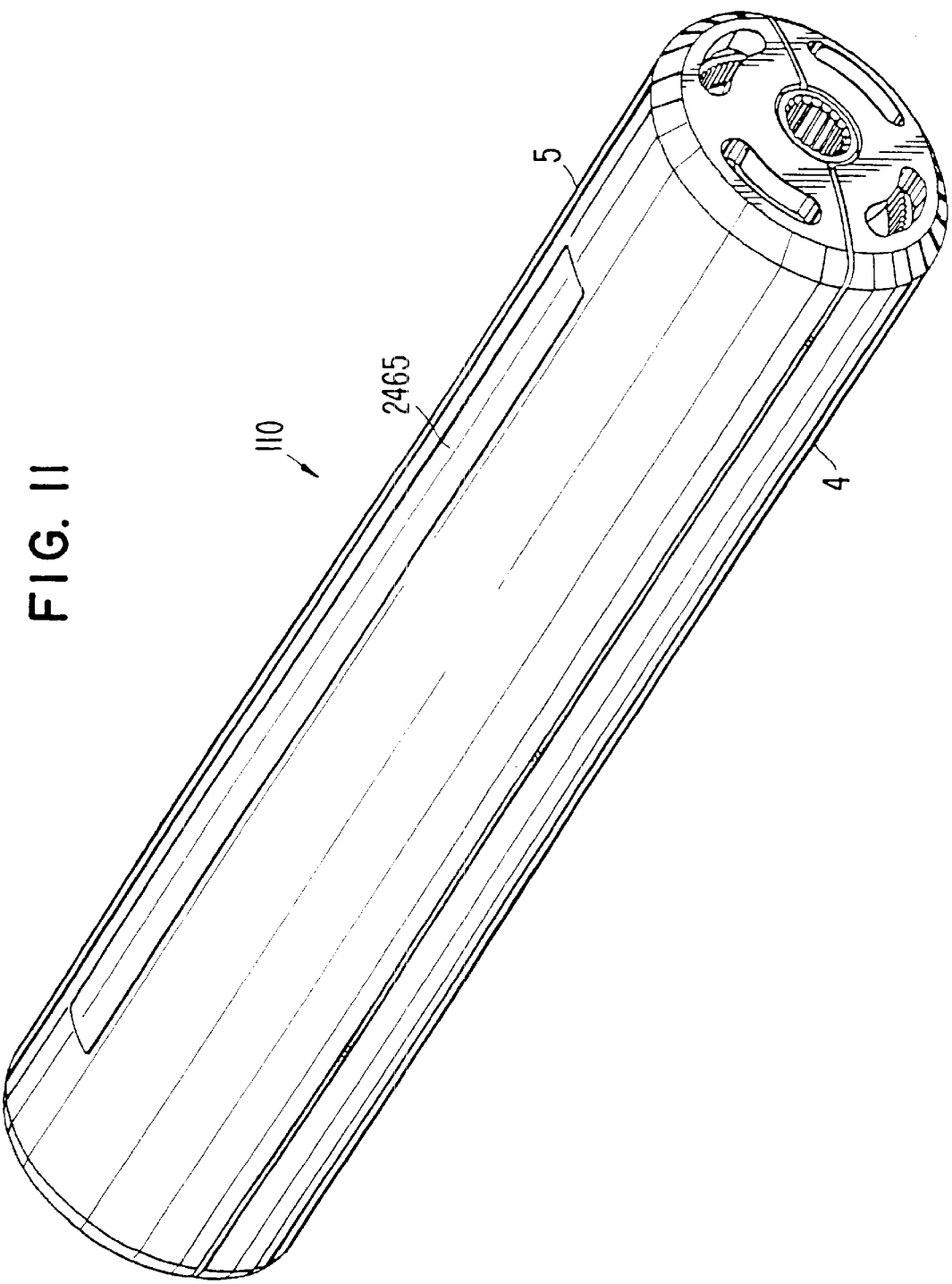
FIG. 11 shows a cartridge that can be inserted into the medical instrument, according to the present invention.

Referring now to FIGS. 1–10, which show views from different angles, the medical instrument 700 includes a handle 705 which has an actuator/trigger 180 by which a user can push inwards to eject a seed out of the medical instrument 700 and into a needle 770, and thereby into a patient. The medical instrument 700 is shown as having a cartridge accepting region for accepting a seed cartridge 110 that contains seeds. The cartridge accepting region is located at a distal portion of the medical instrument 700 adjacent to the location where the needle 770 is coupled to the medical instrument 700. The cartridge 110, which includes a seed capacity indicator (not shown) located underneath the lens 2465, is the subject of the CARTRIDGE-MOVEABLE SHIELD related patent application, referred to previously. The seed cartridge 110 is shown by itself in FIG. 11.

As a seed is fired from the medical instrument 700 and into a patient by way of the needle 770, the medical instrument 700 backs out from the sheath unit 780 in a direction away from the grid template 740. In more detail, as the trigger/actuator 180 on the handle 705 of the medical instrument 700 is engaged by a predetermined amount from its home position (e.g., approximately one-half the maximum allowable stroke of the trigger 180 on the handle 705), a seed is removed from the seed cartridge 110 by the medical instrument 700, and the seed is pushed into the needle 770 by way of a pusher, or stylet 2410, located within the housing of the medical instrument (not shown in FIGS. 1–10). As the user continues to engage the trigger mechanism 180 past the predetermined amount to its fully engaged position, the medical instrument 700 moves back away from the grid template 740, but remains coupled to the sheath unit 780.

In more detail, the medical instrument 700 moves backwards in a direction away from the grid template 740 (and thereby away from the patient), while still seated in the sheath unit 780. This occurs due to the nut box interface 145 moving from its initial location at its most proximal position, to a position that approaches the distal end (the end at which the needle is attached) of the medical instrument 700. In other words, as the trigger/actuator 180 is actuated to move the medical instrument 700 back away from the grid template 740, the nut box interface 145, which is grabbed by an element on the bottom surface of the sheath unit 780, is held in a fixed position with respect to the sheath unit 780, while the rest of the medical instrument 700 moves backwards with respect to the sheath unit 780. In FIGS. 1 and 2, the nut box interface 145 is shown at its most proximal position on the medical instrument 700.

The nut box interface 145 is capable of movement longitudinally within the slot 127 in which it is disposed on the top side of the medical instrument 700, as seen best in FIGS. 1 and 2. The slot distance is approximately the depth of a largest prostate gland (e.g., 3"). The maximum stroke of the medical instrument 700 is determined by this slot distance. Once the medical instrument 700 has moved the entire distance of the slot 127, the nut box interface 145 cannot move any further (since it abuts against the distal end of the slot 127), and the medical instrument 700 has to be reset back into its "zero" or "home" position within the sheath unit 780. The resetting is by way of a user pushing against the first and second side buttons 791, 792 in FIG. 10, which releases the nut box interface 145 from a drive screw (an internal component of the medical instrument to which the nut box interface 145 rides along and can be decoupled from) of the medical instrument 700 to which it is normally attached, thereby allowing a user to slide the medical instrument 700 within the sheath unit 780 back to a next seed implantation "zero retraction point" position with respect to the grid template 740. When the first and second side buttons 791, 792 are released, the nut box interface 145 re-engages with the drive screw 1210.

At the proximal end of the medical instrument 700 of FIG. 1 is a pitch adjustment knob 170, which can be set to a position to move the medical instrument 700 backwards by a desired amount between consecutive seed implant locations. The pitch adjustment knob 170 may be moved from position to position between seed firings, based on a particular plan that is adopted to treat a patient. A pitch indication window 165 is provided near the pitch adjustment knob 170, to provide a visual indication to the user of the currently-selected pitch amount.

Also shown in FIGS. 1 and 2 is a vernier feature 150A, 150B provided on each side of the medical instrument 700. The vernier feature 150A, 150B informs a user as to the exact z-position during a seed-implanting process. In more detail, the vernier feature 150A, 150B corresponds to a 0 to 3" (or 0 to 80 mm) scale provided on both sides of the medical instrument 700, whereby a window slides over a particular numeric indicator on that scale to inform the user as to the depth of the needle 770 with respect to the proximal and distal ends of the prostate gland. In other words, the vernier feature 150A, 150B informs that user as to how far in the z-direction the medical instrument 700 has moved with respect to the zero retraction point. FIG. 1 shows the vernier feature 150A in the home, or "0", position.

FIG. 1 also shows a seed counter indicator 190 provided at a top portion of the handle 705, and which counts the number of seeds that have been fired. A counter reset button 195 is provided near the seed counter indicator 190, and when pushed resets the count to "0". The count reset feature may also (or alternatively) be coupled to the motion of the needle release handle 160.

Also shown in FIG. 1 is a cosmetic flapper 175, which defines the handle position at the onset of the medical instrument indexing or movement. Thus, as the handle is moved from its unengaged position to the position corresponding to the location cosmetic flapper 175, the medical instrument 700 has not moved as yet. When the handle is moved further inwards, thereby causing the cosmetic flapper 175 to move with it, the medical instrument 700 moves (or indexes).

The nut box interface 145 is shown as having a nut box release trigger 137, which releases the nut box interface 145 from the drive screw when engaged. The nut box release trigger 137 is actuated when the first and second side buttons 791, 792 on the sheath unit 780 are engaged.

At the back portion of the medical instrument 700 there is disposed a needle release 160, which releases the needle 770 from the medical instrument 700. There may also be provided a second needle release on a front portion of the medical instrument 700. FIG. 1 also shows a seed transfer command button 185, which causes a seed to be transferred from the seed cartridge 110 to the medical instrument 700, by causing a seed within the seed cartridge to be placed within a shuttle and to cause the shuttle to extend from the cartridge, with the seed in place within a seed-accepting-hole of the shuttle.

As an optional feature, the medical instrument 700 may include a nut box "not home" warning indicator, which provides a warning indication when the nut box interface 145 is not in the "home" position.

Now, a description will be made with regards to a needle within a patient's body, and the effects of the needle movement on one or more seeds already implanted in the patient's body.

When the medical instrument is first inserted within the patient, the needle 770 is fixed in position, so that the needle 770 is pointed straight into and through the patient's skin, directly along an axis in which the medical instrument 700 is being moved. The coupling of the needle 770 to the medical instrument 700 is by way of a needle hub configuration at a distal end of the medical instrument 700. When the needle 770 is positioned at the proper depth within the patient (e.g., at the proper location for initially depositing seeds into the prostate), the operator activates a button 185 on the medical instrument 700, in order to provide a seed (obtained from the seed cartridge 110 housed within the medical instrument) to the patient's prostate, by way of the needle 770.

Once a first seed or first group of seeds are deposited at the initial, furthest-depth position within the patient's prostate gland, the medical instrument 700 is moved, so as to inject a next seed or group of seeds at a position in the prostate gland that is closer to the point at which the needle 770 initially entered the patient's skin. This movement of the medical instrument 700, while it is coupled to the sheath unit 780, is described above with reference to the nut box assembly 145 and its movement within the medical instrument 700.

During the seed implantation procedure, care must be taken that the needle 770 does not go directly back solely in a linear, non-rotated manner from a first seed implantation position to a second seed implantation position. This is the case since such movement tends to cause the seeds deposited in the first position to be sucked, or drawn, towards the second position, as recognized by the inventors. This sucking action is undesirable, and leads to seeds being moved to undesired locations within a patient's prostate. These undesired locations are locations different from where the seeds were initially deposited by way of the needle 770. The exact cause for this sucking action is not completely known, but it is probably due at least in part to the fluid within the patient's prostate gland causing the seeds to be drawn in a direction in which the needle 770 is being drawn, whereby the fluid moves with the needle 770 and creates a linear flow path within the patient's prostate for the seed to move along. In addition, compressed air as a result of seed insertion into tissue, or vacuum caused by needle retraction, may also cause undesired seed sucking action.

The present invention overcomes the problem of improperly disposed seeds, by having the needle 770 swivel, or spin, as the medical instrument 700 is moved directly back away from the patient and in a direction towards the needle insertion point on the patient's skin. By having the needle 770 spin between seed implantation points, the problem due to seeds being drawn towards the withdrawing needle 770 does not occur, at least to the extent that it occurs in conventional procedures that withdraw the needle straight back between seed implantation locations. The spinning action of the needle 770 in accordance with the present invention interrupts the vacuum that is caused when the needle 770 is moved directly back in a linear manner, where this vacuum tends to pull the seeds in a direction in which the needle 770 is being moved to a new seed-implanting location. With the vacuum interrupted, the pull effect on the seeds does not occur, at least to the extent that it would occur if the needle 770 is not spun/swiveled/or rotated between seed implant locations.

Preferably, the needle 770 is locked in place and does not spin or swivel, when the medical instrument 700 (and hence the needle 770 coupled to it) is moved inwards into the patient's body, to a furthest-depth position within inner cavity of the patient. As the medical instrument 700 (and hence the needle 770 coupled to it) is moved back away from the patient, whereby the seeds are implanted at various positions within the prostate gland (from the deepest position to the shallowest position), the needle 770 is caused to spin or swivel, as it is retracted to a new position. The needle 770 spins or rotates when the needle 770 is moved between seed implant locations, while the needle 770 does not spin or rotate at other times.

Also, it is important that the needle 770 be properly coupled to the medical instrument 700, in that the needle 770 does not move from its proper position for implanting seeds. A needle hub configuration, whereby the needle 770 is to be coupled to components at a distal end of the medical instrument 700, is needed to allow such coupling.

Figure 12:
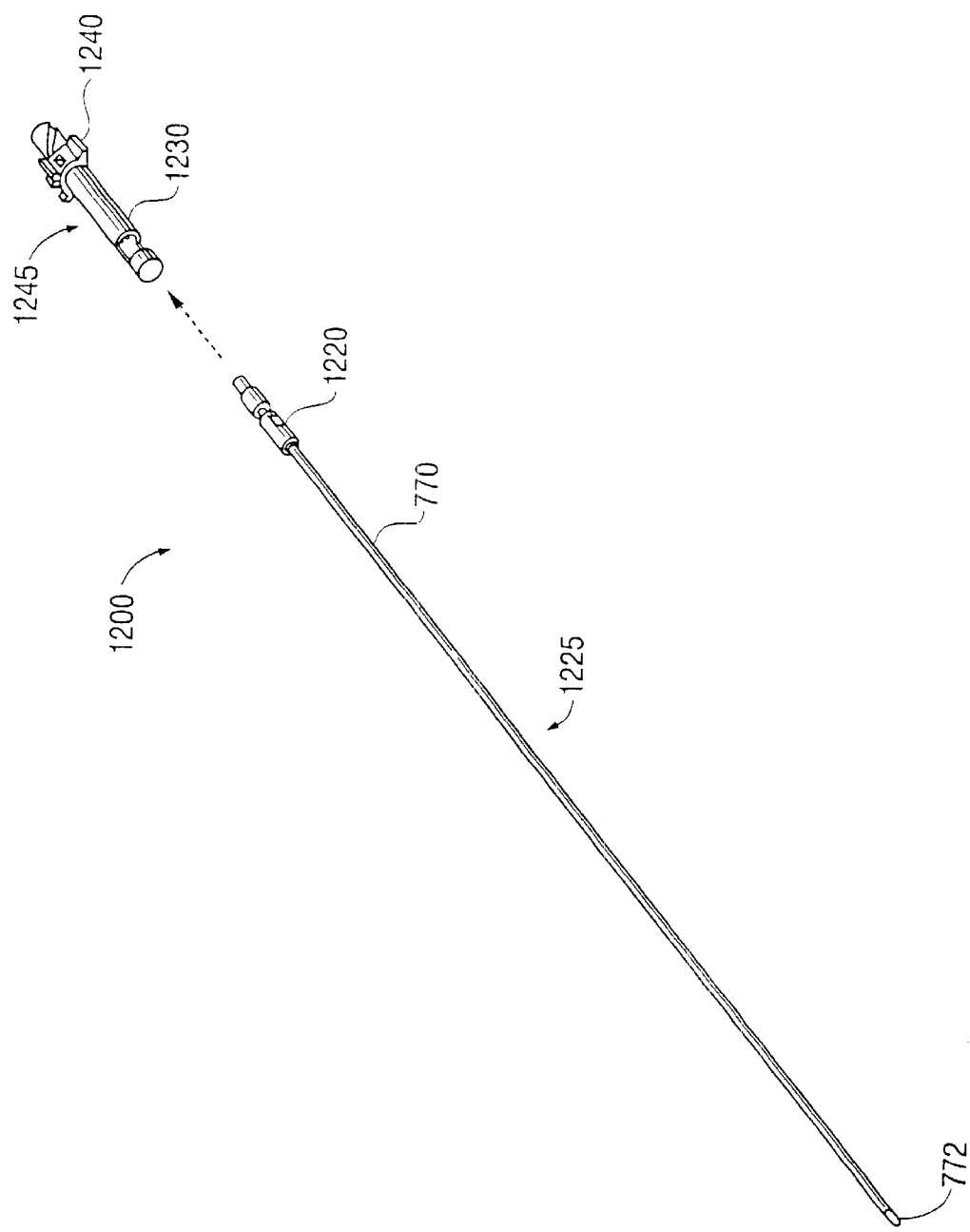
FIG. 12 shows a needle spin mechanism assembly, as well as a needle hub configuration for attaching a needle to a medical instrument, according to the present invention.

FIG. 12 shows a perspective view of various elements in a needle hub assembly 1200. These elements include a needle cannula 770 and a needle hub 1220, which make up a needle assembly 1225. Other elements include a needle cam 1230 and a collar 1240, which provide a needle spin mechanism 1245 for a needle coupled to the medical instrument. The needle hub 1220 and needle cam 1230 make up a needle/medical instrument coupling structure (along with other components, such as a needle retention arm, to be described later on).

The needle hub 1220 is fitted tightly onto the proximal end (that is, the non-beveled end) of the needle cannula 770, whereby the needle hub 1220 cannot be readily removed from the needle cannula 770 without damaging the needle assembly 1225. In essence, the needle assembly 1225 is an integral component, whereby the needle cannula 770 and the needle hub 1220 can be considered to be a one-piece item after a manufacturing process of coupling the needle hub 1220 to the needle cannula 770. The needle hub 1220 is preferably a plastic part, while the needle cannula 770 is preferably a metal part. The needle cam 1230 and the collar 1240 are preferably plastic parts.

Figure 13:
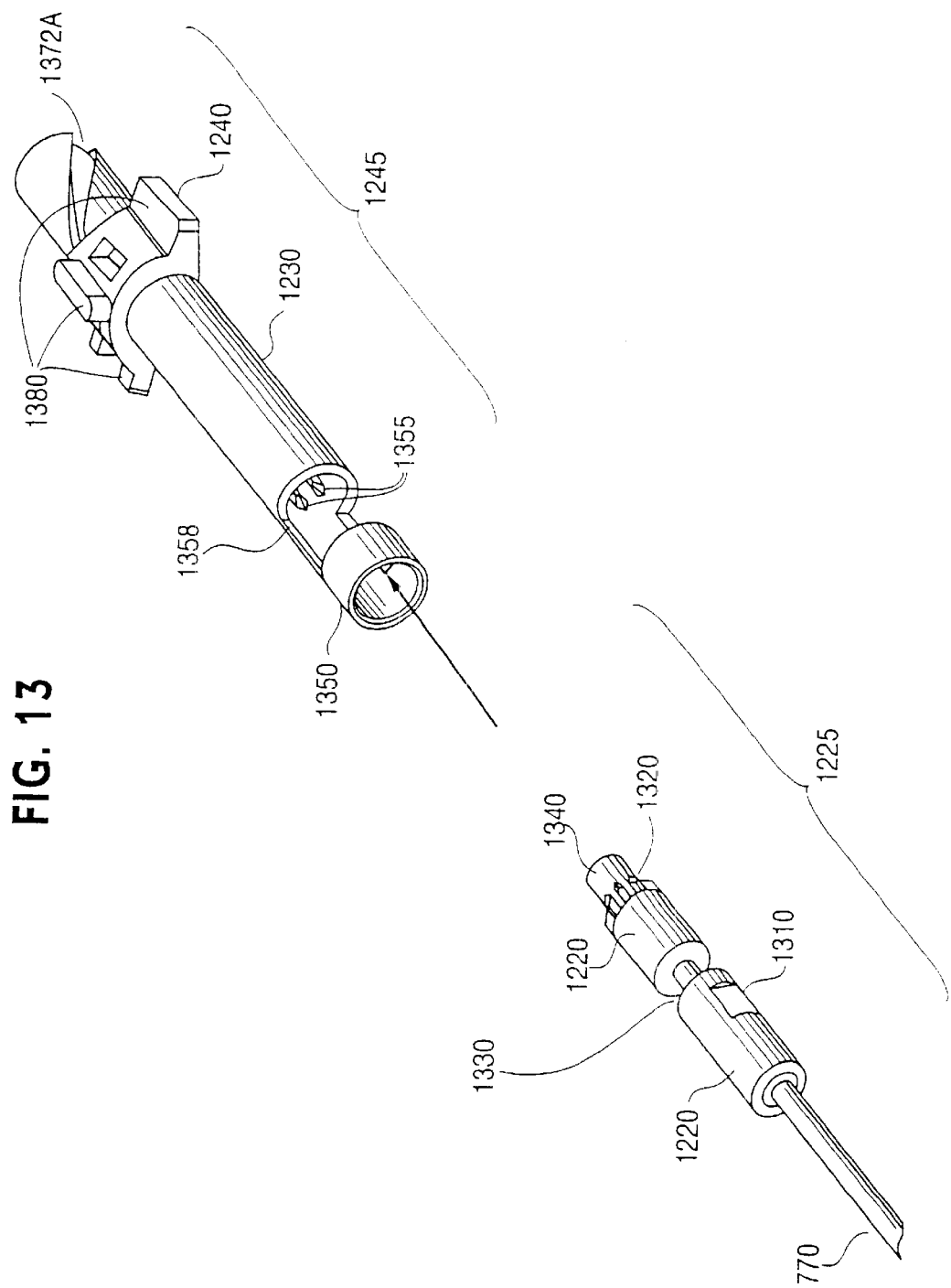
FIG. 13 shows a blow-up of the elements used to couple the needle assembly to the needle cam, so as to provide a coupling of the needle to the medical instrument, according to the present invention.

FIG. 13 is a blow-up view of the proximal end of the needle assembly 1225 and the needle spin mechanism 1245. The needle hub 1220 includes a needle bevel point orientation indicator 1310, a needle release arm retention slot 1330, and needle registration ribs 1340 with rib lead-in chamfers 1320.

The needle cam 1230 includes a needle stabilizer collar 1350, cam registration ribs 1355, and an opening 1358 for a needle release arm 1360. The collar 1240 is configured to move along two cam slots 1372A, 1372B (only one visible in FIG. 13) on the proximal end of the needle cam 1230. The collar 1240 includes anti-rotation ribs 1380, which will be explained in more detail in a later portion of this application.

For performing a medical procedure, the needle cannula 770 may have to be inserted in one of a multitude of angular positions, and the present invention allows for such different angular insertions of the needle cannula 770. The needle registration ribs 1340 on the needle hub 1220 are male protrusions that are received by female features, corresponding to areas between the cam registration ribs 1355, disposed on an inner surface of the needle cam 1230. That way, when the needle hub 1220 is inserted into the needle cam 1230, the needle registration ribs 1340 register with the cam registration ribs 1355.

Due to the chamfers 1320 on the needle registration ribs 1340, the needle hub 1220 can be properly inserted into the needle cam 1230, even if the needle registration ribs (male features) of the needle hub 1220 are not exactly coincident with the corresponding cam registration ribs (female features) of the needle cam 1230. The chamfers 1320 allow the needle assembly 1225 to find the correct orientation when the needle hub 1220 is inserted into the needle cam 1230, to thereby provide registration of the needle registration ribs 1340 with the cam registration ribs 1355 (or more precisely, between adjacent ones of the cam registration ribs 1355).

When bevel-ended needles are utilized, the needle bevel point orientation indicator 1310 provides for the distal end 772 of the needle to be properly oriented during manual insertion into the patient. It provides an orientation indicator for a surgeon who will insert needles into a patient. Alternatively, a trocar needle may be utilized for implanting seeds, whereby the trocar needle would be coupled to the needle hub 1220 to form a needle assembly. In that case, the needle bevel point orientation indicator 1310 is not needed, and the needle hub 1220 would not have such a feature.

Figure 18:
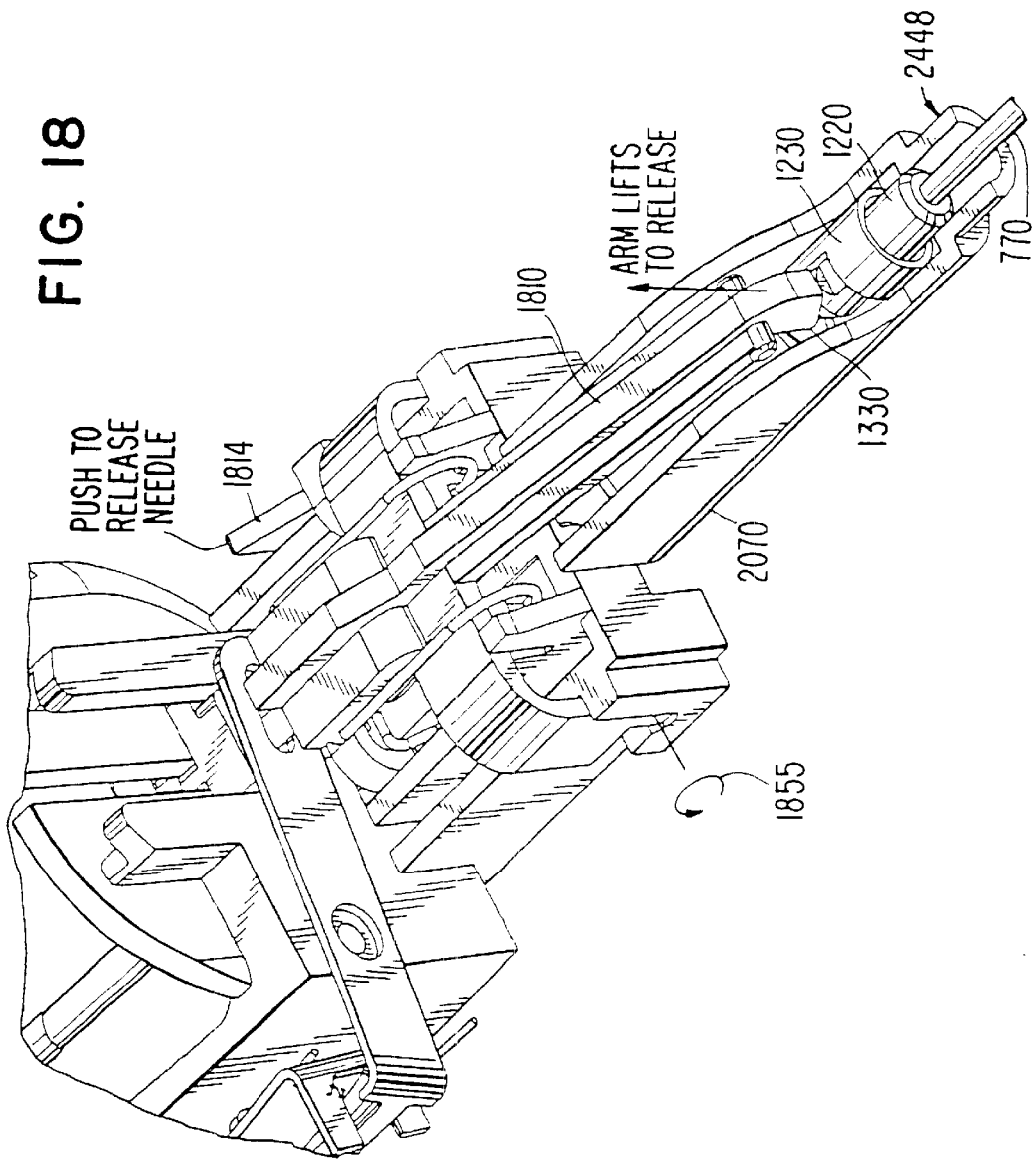
FIG. 18 shows a top perspective view of the needle assembly coupled to a medical instrument, according to the present invention.

The opening 1358 is a region whereby a needle release arm 1810 is disposed, when the needle release arm is in the down position to help hold the needle 770 in place within the distal frame portion of the medical instrument 700. FIG. 18 shows the needle release arm 1810 in the down position, whereby its distal end is disposed within the opening 1358.

When the needle hub 1220 is inserted into the needle cam 1230, the needle release arm 1810 lifts up momentarily (as the proximal portion of the needle hub 1220 is fitted into the needle cam 1230) by riding up over the needle hub 1220 that is being pushed into the needle cam 1230. When the needle assembly 1225 is in place within the needle cam 1230, the needle release arm 1810 drops down to rest within the needle release arm retention slot 1330.

The fitting of the needle registration ribs 1340 between the cam registration ribs 1355 is preferably a "close clearance" fit. By way of example and not by way of limitation, a two to ten thousandths of an inch clearance between the ribs can be provided to provide a proper fit of the needle hub 1220 with the needle cam 1230.

The opening 1358 for accepting the needle release arm 1810 is an opening of 180 degrees (e.g., half-circular region), to allow for a 180 degree rotation of the needle 770 while allowing the needle release arm 1810 to remain in place in the needle release arm retention slot 1330. The opening 1358 is provided so that the needle release arm 1810 will not make contact with the needle cam 1230 during the 180 degree rotation of the needle 770. While the present invention is described with reference to a 180 degree spin of the needle 770, other amounts of spin between seed implant locations may be envisioned, while remaining within the scope of the invention as described herein. For example, a needle spin anywhere from 45 degrees to 720 degrees (or more) may be performed to maintain implanted seeds in place within a patient's body when the needle 770 is moved to a next seed implantation point (or out of the body altogether).

The needle assembly 1225 is caused to spin by movement of the collar 1240, which itself is coupled to the needle cam 1230, whereby the needle cam 1230 is coupled to the needle assembly 1225 (due to the registration of the needle hub 1220 with the needle cam 1230). The collar 1240 has two pins 2310A, 2310B provided on opposite sides of the collar 1240, as seen best in FIGS. 23A, 23B, 23D and 23F. Those pins 2310A, 2310B are respectively engaged into two helical slots 1372A, 1372B that are provided on a proximal end of the needle cam 1230. The collar 1240 rides up and down the needle cam 1230, by way of the pins 2310A, 2310B of the collar 1240 riding along the slots 1372A, 1372B of the needle cam 1230. The slots 1372A, 1372B of the needle cam 1230 are preferably disposed 180 degrees apart from each other, on the proximal end of the needle cam 1230.

Figure 20:
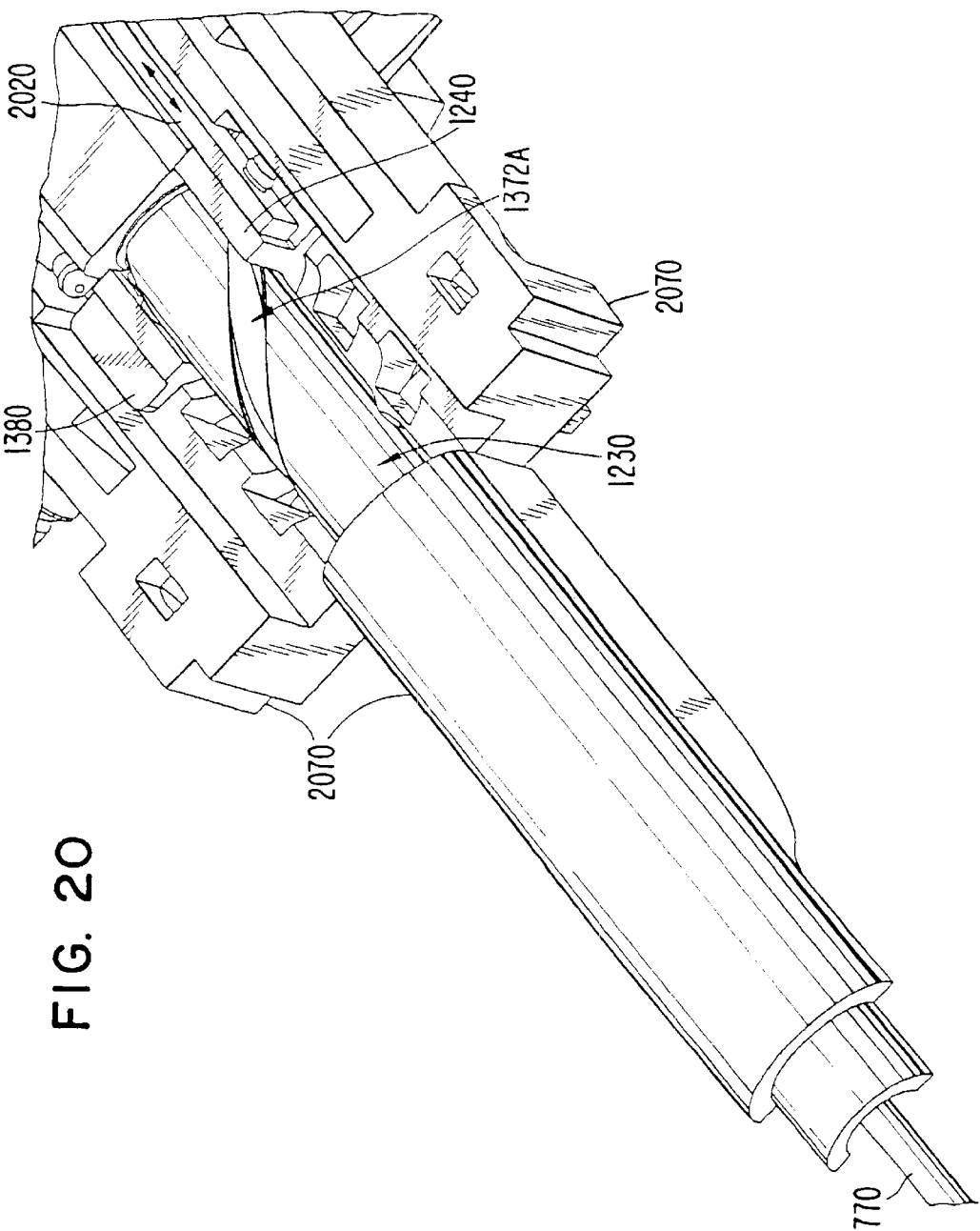
FIG. 20 shows a bottom view of a blow up of a region of the distal frame portion of the medical instrument in which the collar is disposed, whereby the coupling of the collar to a control link is shown, according to the present invention.

FIG. 20 shows a blow up of a portion of a distal frame portion 2070 of the medical instrument 700, which shows the collar 1240 placed into its proper position within the distal frame portion 2070 of the medical instrument 700. A control link 2020 moves in a linear direction as shown by the double-arrow line in FIG. 20, whereby an actuation of the trigger 180 on the medical instrument 700 causes the control link 2020 to move, to create a pulling action on the collar 1240. The collar 1240 is shown in FIG. 20 as being in an actuated position, whereby an action by the operator has caused the control link 2020 to be pulled in a direction towards the medical instrument 700, thereby causing the collar 1240 to be moved in that same direction. The control link 2020 includes a hole at a distal end thereof, whereby a control link attachment pin 2320 of the collar 1240 is fitted through that hole (see FIGS. 23A, 23B, 23D, 23E, 23F). That way, when the control link 2020 is pulled back in a direction towards the medical instrument 700, the collar 1240 is pulled back in that same direction as well.

FIG. 20 also shows the anti-rotation ribs 1380 of the collar 1240, which maintain the collar 1240 in its proper position, and do not allow the collar 1240 to rotate or move in a direction other than a direction in which the control link 2020 moves. FIGS. 23A through 23F show the anti-rotation ribs 1380 on the collar 1240. The collar 1240 is in its resting, or home position, when it is at its most distal position with respect to the medical instrument body. The collar 1240 is shown in its most proximal position in FIG. 20.

Figure 14:
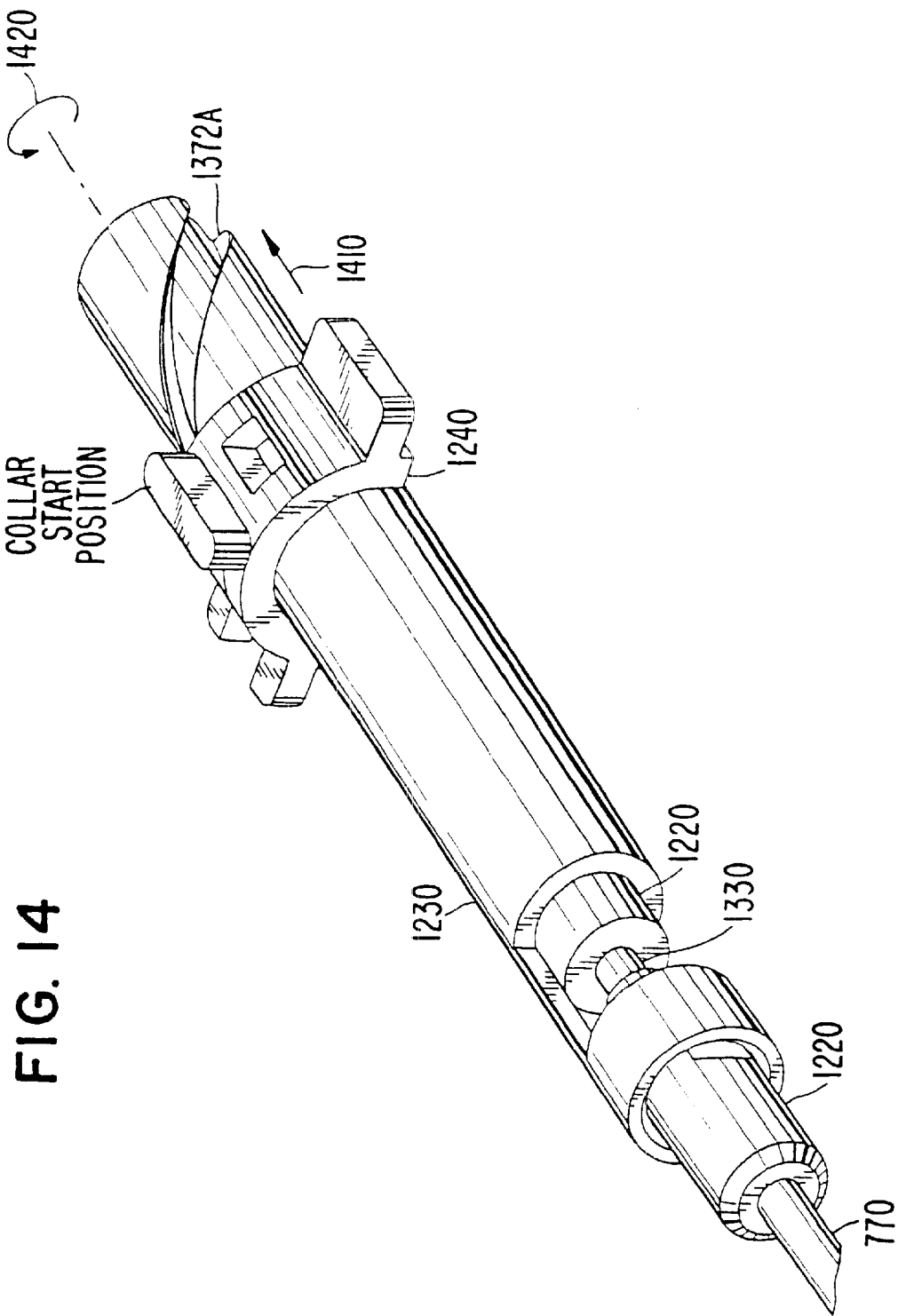
FIG. 14 shows a blow-up of the needle assembly coupled to the needle cam, as well as elements used to cause the needle assembly to spin while being coupled to the needle cam, according to the present invention.

FIG. 14 shows the direction of collar movement, by way of the "collar motion" arrow 1410 provided in that figure. Collar motion in the direction of the collar motion arrow 1410 results in rotation of the needle cam 1230 (as seen by the curved arrow 1420 in FIG. 14). This causes the needle 770 to spin in that same direction (a counter-clockwise direction as shown in FIG. 14, but the present invention is also applicable to a rotation of the needle 770 in a clockwise direction).

Figure 15:
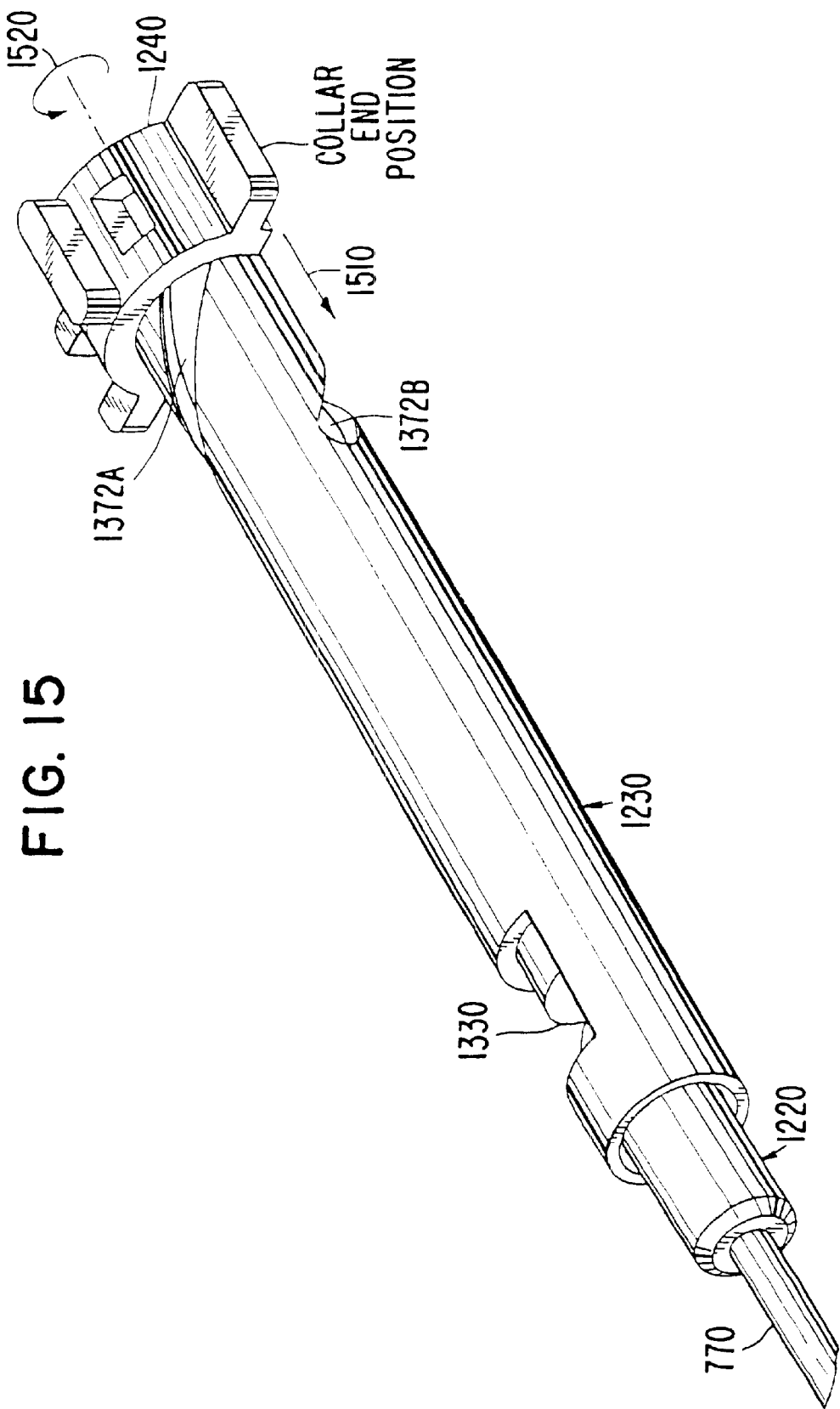
FIG. 15 shows a view similar to that shown in FIG. 14, but whereby the needle assembly and needle cam have each been rotated 180 degrees by movement of the collar attached to the needle cam, according to the present invention.

FIG. 15 shows the position of the needle hub 1220 and needle cam 1230 after the collar 1240 has been moved from its most distal position to its most proximal position with respect to the main body of the medical instrument 700. The collar 1240 will return to its home, or most distal position, for the next trigger cycle (that is, next seed implant cycle).

To return to its home position, the needle 770 will rotate or spin in a clockwise direction, to return back to the position as shown in FIG. 14.

In the preferred embodiment, the movement of the control link 2020 is caused by a gear assembly and other linkage components within the main body of the medical instrument 700, whereby the needle 770 is caused to spin by movement of the control link 2020 in a direction as shown in FIG. 20. The needle spin occurs after a seed has been implanted, at a time when the medical instrument 700 is being retracted to a next seed implantation position for implanting seeds within the patient's body. In the present invention, the needle spin will also occur after the medical instrument 700 has indexed to the next seed implantation position, whereby the needle 770 will spin in place back to its initial angular position with respect to the medical instrument 700.

As explained above, the control link 2020 is coupled, by way of various coupling elements (not shown), back to a drive rack assembly (see FIG. 34, for example) located within the medical instrument 700, whereby the stroke of the control link 2020 is controlled by movement of the drive rack assembly (which in turn is caused by movement of the trigger 180 on the handle 705 of the medical instrument 700). Details of the various coupling elements are not discussed herein, in order to provide a more clearer description of the present invention as it relates to a needle hub configuration and to a needle spin configuration.

In the present invention, regardless of the amount of index pitch, that is, regardless of the amount that the medical instrument 700 moves between consecutive seed implantation positions, the needle 770 spins the same amount (180 degrees in the preferred embodiment, but other amounts of spin may be envisioned) during that movement of the medical instrument.

In an embodiment of the present invention, there are five possible pitch settings for the medical instrument 700, whereby a particular pitch setting is effected by actuation of the pitch adjustment knob 170 at the proximal end of the medical instrument 700. In the preferred embodiment, the minimum pitch index is 5 mm, and the maximum pitch index is 15 mm. Other numbers of pitch settings are possible (e.g., two to twenty), and other minimum and maximum pitch sizes are possible, while remaining within the scope of the invention as described herein. Regardless of which pitch setting is being used, the needle 770 rotates 180 degrees during the movement of the medical instrument 700 to a next seed implantation position.

Figure 16A:
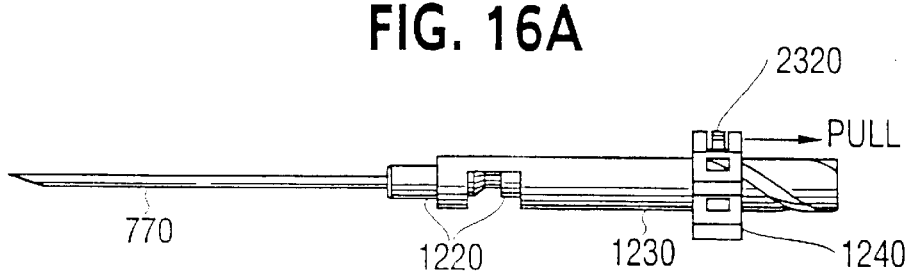
FIGS. 16A and 16B show top and side views, respectively, of the needle spin assembly and needle coupling assembly, when the needle assembly is in a start (unrotated) position, according to the present invention.
Figure 16B:
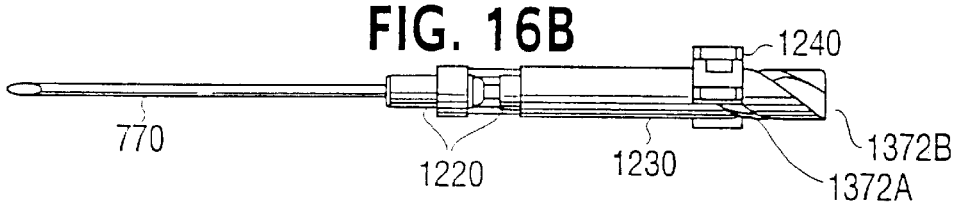
Figure 16C:
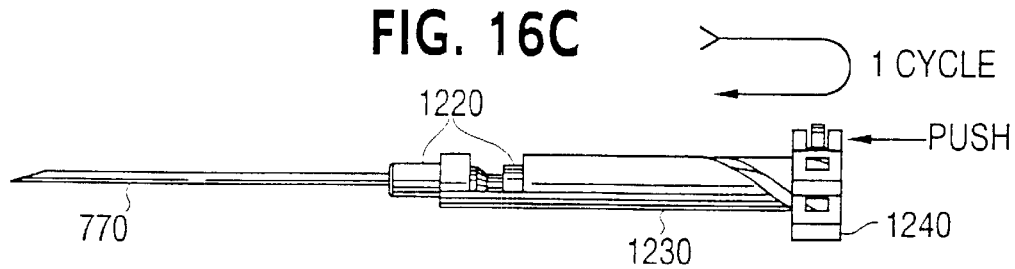
FIGS. 16C and 16D show top and side views, respectively, of the needle spin assembly and needle coupling assembly, when the needle assembly is in an end (fully rotated) position after one needle spin cycle, according to the present invention.
Figure 16D:
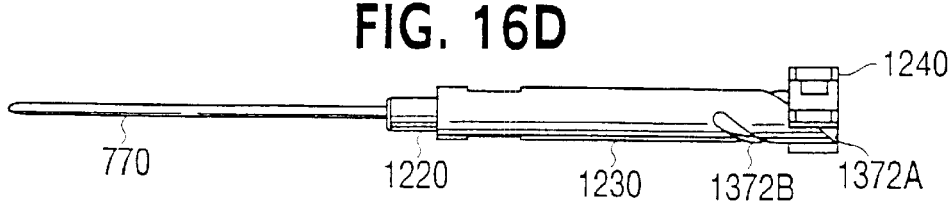

FIGS. 16A and 16B respectively show a top view and a side view of the needle hub assembly 1200 in the start position (collar 1240 at its most distal position on the needle cam). FIGS. 16C and 16D respectively show a top view and a side view of the needle hub assembly 1200 in an end position, which occurs after one seed implantation cycle. The collar 1240 has been pulled to its most proximal position on the needle cam 1230, whereby it will release back to its most distal position, to complete the cycle, and to set up for a next seed implantation cycle.

The two helical slots 1372A, 1372B of the needle cam 1230 can be seen in FIGS. 16B and 16D; and opposing pins of the collar 240 ride along these slots by operation of the control link 2020.

FIGS. 17A and 17B are similar to FIGS. 16A and 16B, whereby two cross sectional cuts are shown in FIG. 17B. Those cross sectional views are shown in FIGS. 17E and 17F. FIG. 17C shows a front view of the collar 1240 attached to the needle cam 1230, whereby a cross sectional cut in also shown in that figure. That cross sectional view is shown in FIG. 17D. FIG. 17G shows a bottom view of the collar 1240 and needle cam 1230 being coupled to each other.

FIG. 17F shows the registration of the cam registration ribs 1355 of the needle cam 1230, with the needle registration ribs 1340 of the needle hub 1220.

FIG. 17E shows the two opposing pins of the collar 1240 that are engaging the respective slots 1372A, 1372B of the needle cam 1230. The two opposing pins 1372A, 1372B of the collar 1240 are positioned 180 degrees apart. A conduit 1710 running along the longitudinal center axis of the needle cam 1230 is the region through which the seed and pusher wire (or stylet 2410) pass through, in order to place a seed at a distal end of the needle cannula 770.

In more detail, referring now to the cross-sectional view of FIG. 24, a stylet (also called a "pusher" hereinbelow) 2410 pushes a seed 2420 from a shuttle 2430 (shown in its extended position in FIG. 24) to the distal end 772 of the needle 770. When the medical instrument 700 is retracted to a next seed implantation position, the seed 2420 exits the needle cannula 770 and is left within a particular location within the patient's body (e.g., within some tissue), to thereby provide treatment for the patient.

The diameter of the conduit 1710 is preferably slightly larger (e.g., a few thousandths of an inch) than the diameter of the seed 2420 (typically a cylindrically-shaped object), so that the seed 2420 will be slid along the path of the conduit 1710 through the needle cam 1230, and thereby pass through most of the needle cannula 770 to be deposited at its distal end 772. FIG. 17D shows the longitudinal view of the path that the seed 2420 takes from the distal end of the main body of the medical instrument 700, through the needle cam 1230 and thereby into the needle cannula 770 that is coupled to the needle cam 1230 by way of the needle hub 1220.

Figure 24:
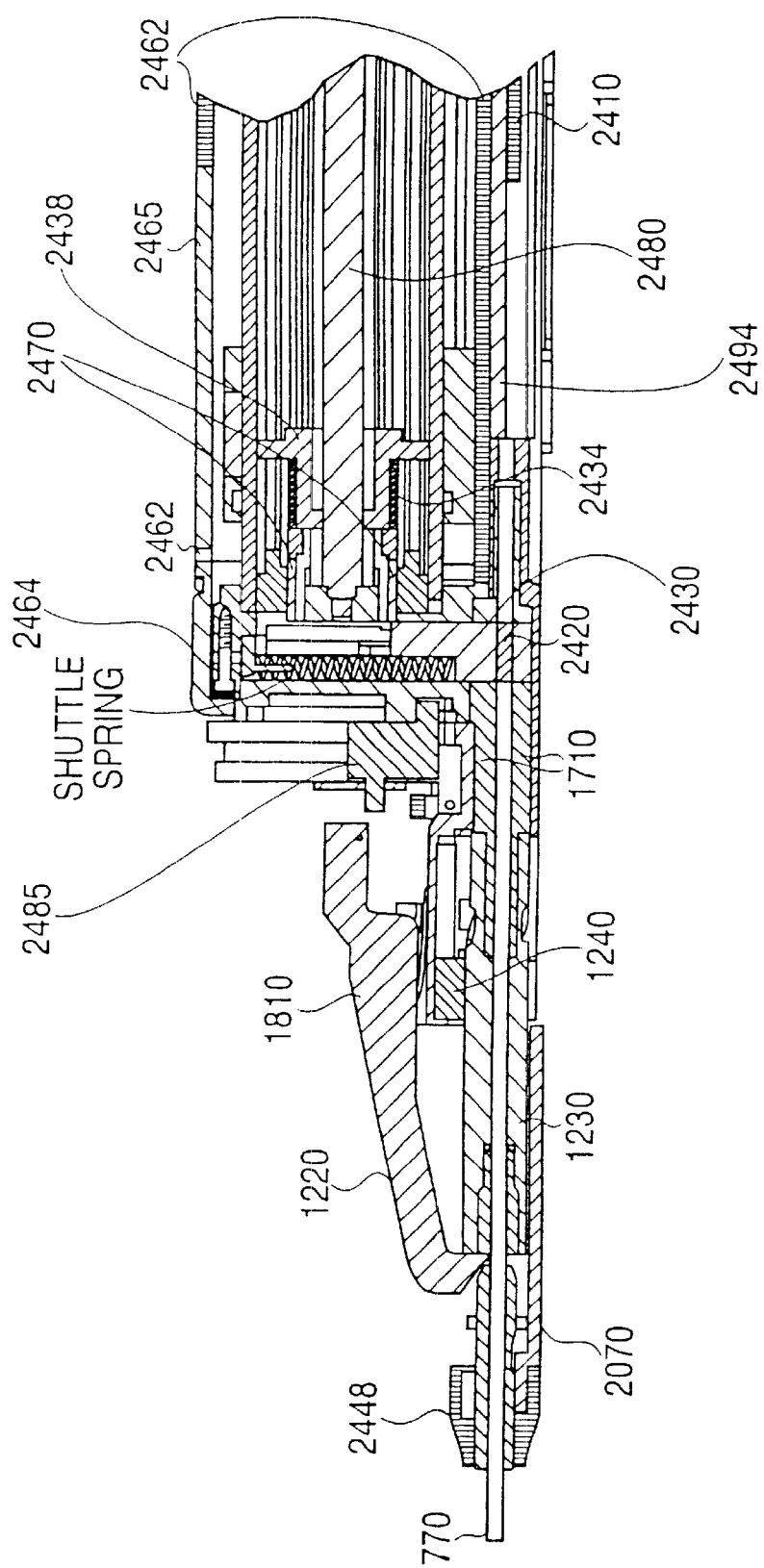
FIG. 24 shows a cross-sectional view of the distal portion of the medical instrument, with a cartridge disposed within the medical instrument and with a needle assembly being coupled to the medical instrument, according to the present invention.

FIG. 24 shows the path that the seed 2420 takes from the extended shuttle 2430, through a conduit-frame 1710, through the needle cam 1230, through the needle hub 1220, and then through the needle cannula 770 to be disposed at its distal end 772. The conduit-frame 1710 is preferably press fitted onto a plastic feature (not shown, but may be a plastic protrusion) at the distal end of the medical instrument 700.

FIG. 24 shows the distal frame 2070 of the medical instrument 700, which holds the needle cam 1230 and needle hub 1220 in place at the distal end of the medical instrument 700. There is also shown a nozzle cap 2448 that affixes to a distal end of the distal frame portion 2070. The distal end of the medical instrument 2070 is shared with the other body parts, and the nozzle cap 2448 helps hold those parts in place.

When inserted in the medical instrument 700, the cartridge 110 is disposed at the distal region within the medical instrument 700, as shown in FIG. 24. The cartridge 110 includes a lens portion 2465 at a top surface thereof, for displaying the current number of seeds remaining in the cartridge 110. A seed 2470 at a top conduit of the cartridge 110, and a seed 2470 at a bottom conduit of the cartridge 110, are also shown in FIG. 24. The seeds 2470 are urged to the distal end of the cartridge 110, by a pusher spring 2434 and a cartridge pusher 2438. Details of the operations of these elements is provided in the CARTRIDGE-MOVEABLE SHIELD application, mentioned previously.

A center rod 2480 is also shown in FIG. 24, which passes through the center axis of the cartridge 110 and which is part of a mechanism by which the cartridge 110 rotates to thereby provide a seed from a different conduit to a seed extraction position (to thereby be provided to a seed accepting hole in a shuttle that is in a retracted position within the cartridge). Details of how the cartridge 110 rotates are provided in the related CARTRIDGE-MOVEABLE SHIELD application, mentioned previously.

FIG. 24 also shows a reset shuttle link 2485 at the distal end of the medical instrument 700, which is provided so as to allow the operator to reset the shuttle 2430 back to its closed position within the main body of the cartridge 110. In FIG. 24, the cartridge 110 is shown having a proximally-located cup 2462 and a distally-located cap 2464, whereby the cup and cap are affixed to each other to provide an outer housing for the cartridge 110. This configuration of the cartridge 110 is slightly different from the configuration shown in FIG. 11, which has a top housing 5 and a bottom housing 4. In the cartridge configuration shown in FIG. 24, the cartridge outer housing is divided into proximal and distal portions, as opposed to top and bottom portions. As shown in FIG. 24, the lens 2465 of the cartridge 110 is provided on a top surface of the cup, when the cartridge 110 is properly positioned within the medical instrument 700. The lens provides for an operator to clearly discern the number of seeds remaining in the seed cartridge 110, by way of a seed count number that is visible to the operator through the lens 2465. See the CARTRIDGE-MOVEABLE SHIELD application for more details on this feature of the cartridge 110.

Referring now to FIG. 22A, the conduit-frame 1710 is preferably a metal part or protrusion located at the distal end of the main body of the medical instrument 700. The metal composition of the conduit-frame 1710 protects the user from any radiation emanating from the seed as it passes through from the extended shuttle 2430 to the needle cannula 770, with the stylet 2410 pushing the seed along that path. The needle cam 1230 is fitted onto the conduit-frame 1710, to thereby couple the needle cam 1230 to the main body of the medical instrument 700 (due to the conduit-frame 1710 being press fitted or insert molded to the frame of the medical instrument 700), with the needle cam 1230 resting on the distal frame portion 2070 of the medical instrument 700 (see FIG. 19, for example). Also shown in FIG. 24 is a pusher guide 2494, which is an element of the medical instrument frame that maintains the stylet 2410 in its proper position when it is extended. The stylet 2410 is shown in its non-extended position in FIG. 24.

A seed implantation process will now be described. By operation of a seed extraction button on the medical instrument 700, a seed is placed into the shuttle 2430 of the seed cartridge 110 provided within the medical instrument 700, and then the shuttle 2430 is extended out from the main body of the seed cartridge 110, via actuation of the seed transfer button 185. By operation of the trigger 180 on the handle 705 on the medical instrument 700 from a first (start) position to a second (intermediate) position, the stylet 2410 is made to extend through a hole in the shuttle 2430 in which the seed is positioned. The stylet 2410 pushes the seed 2420 through the conduit-frame 1710, through the conduit 1710 in the needle cam 1230, and then into the needle cannula 770, to thereby be placed at its proper position at the distal end 772 of the needle cannula 770. Alternatively, if a trocar needle is used, the stylet 2460 would position the seed 2420 at a distal end of the trocar needle.

With the seed 2420 at its proper position, the operator actuates the trigger 180 from its second position to a third position (maximally extended position), to move the medical instrument 700 to a next seed implantation position, whereby the needle 770 is spun during this movement of the medical instrument 700. With the stylet 2410 maintained directly behind the seed at the distal end of the needle cannula 770, and with the needle cannula 770 being spun during the movement of the medical instrument 700 to the next seed implantation position, the seed is caused to exit the needle cannula 770 into a proper location within the patient's body, and to stay in place even after the medical instrument 700 moves to a new position.

The inner diameter (ID) of the needle cannula 770 is preferably slightly larger than the size of the seeds that are to be implanted into a patient. The stylet 2410 is cylindrical in shape, and preferably has a diameter that is slightly larger than the seed diameter (which is also preferably cylindrical in shape). Of course, the stylet 2410 can be sized so that it's diameter is the same or substantially the same size as the seed's diameter, or even slightly smaller. Alternatively, the stylet 2410 may be a hollow cannula instead of a solid wire, to assist in venting trapped air.

FIG. 23A shows a perspective view of the collar 1230. FIG. 123B shows a top view, FIG. 23C shows a left side view, FIG. 23D shows a front view, FIG. 23E shows a right side view, and FIG. 23F shows a bottom view of the collar 1230. The collar 1230 includes anti-rotation ribs 1380 on the left side, the right side, and a top side of the collar 1240. The anti-rotation ribs 1380 maintain the collar 1240 in place within the distal frame portion 2070 of the medical instrument 700. FIG. 20 shows the collar 1240 in position within the distal frame portion 2070. A slot within the distal frame portion 2070, not shown due to the needle cam 1230 blocking it in FIG. 20, is provided to allow the top slot of the collar 1240 to ride therein.

Referring back to FIGS. 23A to 23F, the collar 1240 is shown having two openings 2355, or windows, at a top portion thereof. The openings 2355 are provided only to allow an easier molding of the collar 1240 during a manufacturing process for creating the collar 1240, and the openings 2355 do not serve any other purpose. Also, the two separate anti-rotation ribs 1380 on one side of the collar 1240 are also there solely for allowing an easier molding of the collar 1240 (to allow the control link attachment pin to be formed on the collar 1240 during a manufacturing process). As such, other types of anti-rotation ribs, as well as other configurations of the collar 1240, may be envisioned, while remaining within the scope of the invention as described herein.

As discussed above, the control link attachment pin causes the collar 1240 to move by it being fitted within a hole of the control link 2020. As such, linear movement of the control link 2020 results in linear movement of the collar 1240, which results in a turning, or rotational, movement of the needle cam 1230 and thereby results in a turning or rotational movement of the needle assembly 1225 coupled to the needle cam 1230.

Figure 19:
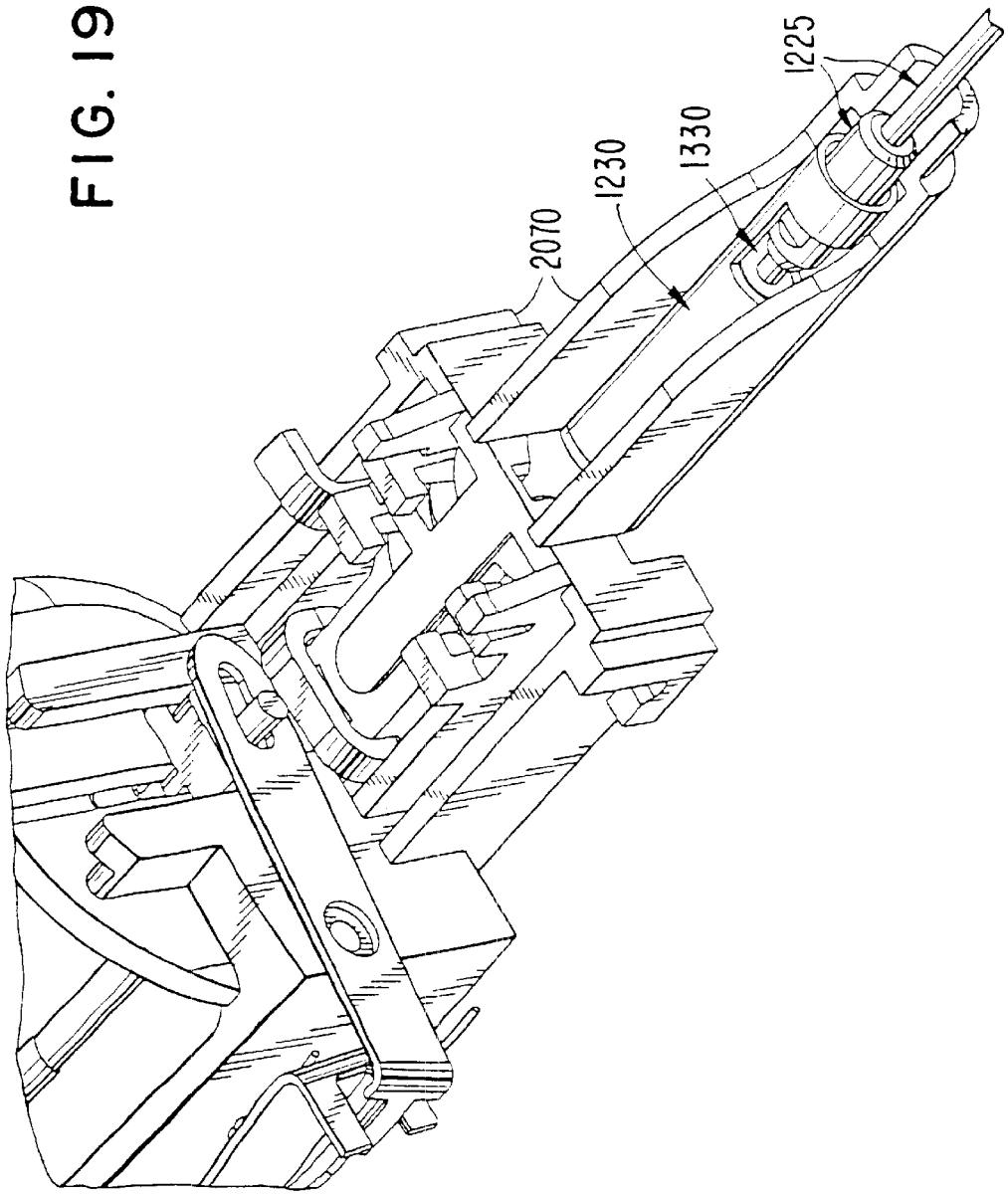
FIG. 19 shows the same view as FIG. 18, but with the needle release arm removed to show a more unobstructed view of the coupling of the needle assembly to the needle cam housed in a distal frame portion of a medical instrument, according to the present invention.

FIG. 19 shows the needle hub assembly in place within the distal frame portion 2070 of the medical instrument 700, and FIG. 18 shows the same needle hub assembly in place, with the needle release arm 1810 also being shown in a "down" position to thereby help hold the needle assembly 1225 in place in the distal frame portion 2070. The distal end of the needle release arm 1810 fits within the needle retention slot 1330 of the needle assembly 1225, when the needle release arm is in the down position. Upon actuation of the release link actuation cam 1814, the needle release arm 1810 pivots about a pivot point 1855 (see FIG. 18), and raises up a slight amount out of the needle retention slot 1330. That way, the needle hub 1220 and needle cannula 770 can be removed from the needle cam 1230, and thereby separated from the medical instrument 700.

The position of the needle cannula 770 (e.g., its depth and location within a patient's body) is typically carefully made in a pre-plan, so that it is undesirable to move the needle position during the coupling of the medical instrument 700 to the needle cannula 770. Typically, the needle cannula 770 is held in place by one hand of the operator, while the medical instrument 700 is held in place by the other hand, whereby the medical instrument 700 is coupled to the needle cannula 770 by way of the needle hub configuration described above.

If any misalignment exists during the coupling of the needle cannula 770 onto the medical instrument 700, that can be overcome (to thereby provide a proper coupling of the needle to the medical instrument) by any of the following configurations: 1) the needle hub 1220 can be configured to readily rotate (while the needle cam 1230 remains fixed in position) to allow slight rotation of the needle cannula 770 within the tissue of the patient to allow proper alignment and coupling of the needle cannula 770 to the medical instrument 700, 2) manual rotation of the needle hub 1220 (and thereby the needle cannula 770) can be performed in order to get a proper alignment of the ribs of the needle hub 1220 with the ribs of the needle cam 1230, 3) a sloppy fit between the ribs of the needle hub 1220 and the ribs of the needle cam 1230 may be provided to allow for coupling of these two elements to each other; or 4) a sloppy fit of the collar pins of the collar 1240 and the helical slots 1372A, 1372B of the needle cam 1230 may be provided to allow a proper coupling of the needle cannula 770 with the medical instrument 700.

In the first configuration described above, the lead-in chamfers 1320 of the needle registration ribs 1340 allow for coupling of the needle hub 1220 to the needle cam 1230, even if they are slightly misaligned with respect to each other. The lead-in chamfers 1320 cause the needle cannula 770 to rotate slightly within the patient's tissue, when the ribs of the needle hub 1220 are registered to the ribs of the needle cam 1230. In this configuration, the needle cam 1230 does not rotate during the alignment procedure.

In the second configuration described above, the needle cannula 770 is manually rotated to place it in proper alignment for coupling the needle hub 1220 to the needle cam 1230. For example, an operator holds the needle cannula 770 in one hand, and holds the medical instrument 700 in his/her other hand. Then, the operator rotates the needle cannula 770 to align the ribs of the needle hub 1220 (attached to the needle cannula 770) to the ribs of the needle cam 1230. In this configuration, the ribs of the needle cam 1230 and the ribs of the needle hub 1220 provide a relatively snug fit, when the needle hub 1220 is coupled to the needle cam 1230.

In the third configuration described above, the registration ribs of the needle cam 1230 and the needle hub 1220 are sized and positioned to allow a somewhat loose fit, so that the needle cam 1230 will rotate or the needle cannula 770 will rotate slightly, to obtain a proper alignment position. For example, if three ribs are provided on the needle cam 1230 and the needle hub 1220, and whereby there is much room between adjacent ribs, the needle hub 1220 can be loosely fit within the needle cam 1230, with space between the engaged ribs. This results in some lost motion during needle spin, e.g., 45 degrees lost motion. However, this lost motion is not a problem due to the large amount of needle spin provided, and whereby the needle coupling procedure is made easier as a result of the loose fitting ribs.

In the fourth configuration described above, the fit between the pins of the collar 1240 and the helical slots on the needle cam 1230 that they ride within, can be made such that the helical slots are slightly larger (e.g., 15 to 20 thousandths of an inch) in width than the size of the pins, to allow for a small amount of rotation (e.g., a few degrees of rotation) of the needle cam 1230. Thus, any slight misalignment of the needle cannula 770 with respect to the needle hub 1220 during a needle/medical instrument coupling procedure can be accommodated.

Any one or more of the above-described four configurations may be utilized with the present invention, to assure a proper alignment of the needle 770 onto the medical instrument 700.

Turning back to FIG. 18, when the release link actuation cam 1814 is actuated to allow the needle assembly 1225 to be removed from the needle cam 1230, the needle release arm 1810 raises up slightly above the needle cam 1230. For example, by way of example and not by way of limitation, the needle release arm 1810 raises 0.010" to 0.050" above the outer surface of the needle cam 1230. This allows the needle hub 1220 and the needle cannula 770 to be removed from the needle cam 1230, such as by pulling the needle cannula 770 in a direction away from the medical instrument 700.

FIG. 20 shows a bottom view of the needle applicator assembly, whereby the positioning of the collar 1240 within the distal frame 2070 of the medical instrument 700, as well as the coupling of the control link 2020 to the collar 1240, can readily be seen.

As seen in FIG. 1, the medical instrument 700 includes a handle 705, which has a trigger 180 which is actuated by an operator, in order to position seeds from the cartridge 110 (placed within the medical instrument 700) to a distal end of a needle coupled to the medical instrument 700. The trigger 180 is in an unengaged position in FIG. 1, which corresponds to a Position A ("home" position). The trigger 180 is moved to a middle Position B, and eventually to a Position C, which is the furthest allowable actuation of the trigger 180. Upon release of the trigger 180, it returns back to its "home" Position A, passing Position B along the way. Position B is preferably positioned approximately halfway between Position A and Position C. Movement of the collar 1240 on the needle cam 1230 happens between trigger Position B and Position C, and then on the return stroke from Position C to Position B.

Due to the actuation of the trigger 180 from Position A to Position B, the stylet 2410 within the medical instrument 700 pushes the seed 2020 from the shuttle 2430 that is in an extended position with respect to the cartridge 110 disposed within the medical instrument 700. The stylet 2410 pushes the seed 2420 through the conduit of the needle cam 1230, and all the way to the distal end 772 of the needle cannula 770. The medical instrument 700 does not move at all during this time.

Now, due to the actuation of the trigger 180 from Position B to Position C, the stylet stays in its most-forward position, and the medical instrument 700 indexes back to a next seed implantation position, while at the same time the needle 770 spins due to the movement of the collar from its most-distal position (relative to the main body of the medical instrument 700) to its most proximal position. This causes the seed located at the distal end of the needle to be released to a proper location within a patient's body (e.g., within a specific location of a prostate gland).

Next, upon release of the trigger 180 by the operator, the trigger 180 returns from Position C to Position B. This results in the collar 1240 moving from its most proximal position to its most distal position, thereby resulting in needle spin (in the opposite direction than what occurred during Position B to Position C movement of the trigger 180). The medical instrument 700 does not move at this time.

Finally, when the trigger 180 travels from Position B to its home Position A, the stylet 2410 returns back to its most proximal position within the main housing of the medical instrument 700, and the shuttle retracts back within the cartridge 110 (after the stylet passes back through it and thereby clears the shuttle). This sets up the medical instrument for a next seed implantation operation, at a next seed implant location within the patient's body.

As explained earlier, due to the surrounding tissue at a seed implantation position, and due to the spinning of the needle to a next seed implantation position, the surrounding tissue will effectively grab the seed so that the seed leaves the needle cannula, while at the same time the seed is not sucked in the direction of movement of the needle cannula due to the spinning motion of the needle cannula.

FIGS. 21A through 21E show different views of the needle hub assembly. FIG. 21A is a top view, FIG. 21B is a side view, FIG. 21C is a front view, FIG. 21D is a back view, and FIG. 21E is a perspective view. FIG. 21E shows the needle hub 1220 without the needle cannula 770 coupled to it. A lead-in chamfer 2178 is provided at the proximal end of the needle hub 1220, so that the stylet 2410 will not get caught against the inner surface of the needle hub 1220, but rather will ride up on the lead-in chamfers 2178 to a proper position, when its makes it way to the distal end 772 of the needle cannula 770.

FIGS. 22A through 22G show various views of the needle cam 1230, in which the helical cam slots can be readily seen in FIGS. 22A, 22B, 22C and 22D. Also, the registration ribs 1355 within the inner surface of the needle cam 1230 can be readily seen in FIGS. 22F and 22G. FIG. 22F also shows a chamfer lead-in 2262 to the conduit-frame 1710, to ensure that the stylet 2410 and the seed 2420 being pushed by the stylet 2410 do not get caught up on the distal end of the needle stabilizer collar 1350 (see also FIG. 13) when the seed 2420 is pushed all the way to the distal end 772 of the needle cannula 770.

The drive mechanism for the medical instrument will now be described in detail, with respect to a preferred embodiment of the invention.

Figure 25:
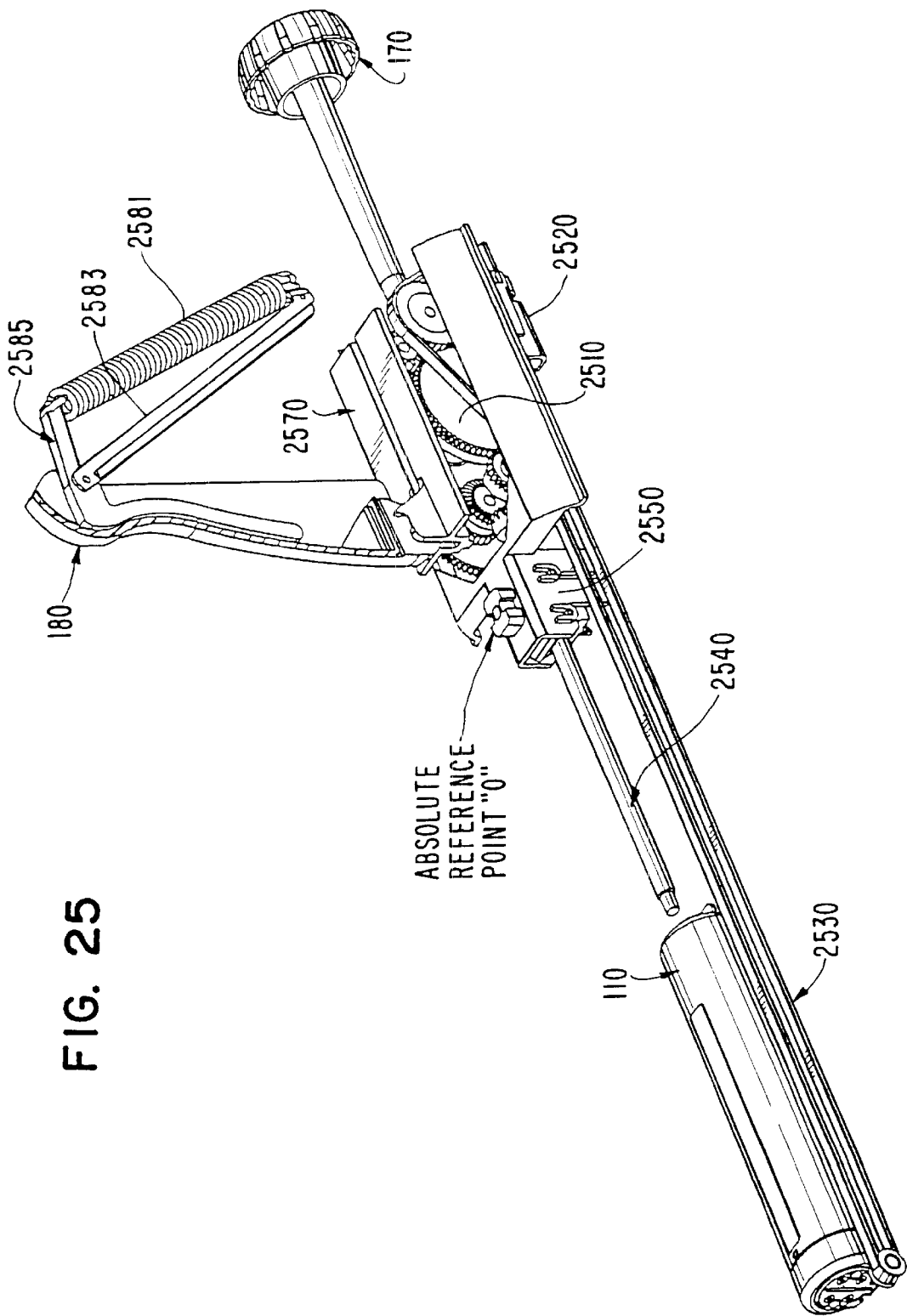
FIG. 25 shows a top perspective view of some of the internal components within the medical instrument (with the outer housing removed), which provide stylet movement and indexing of the medical instrument.

FIG. 25 shows the core elements of a drive mechanism for the medical instrument 700 according to a preferred embodiment of the invention. Not shown in FIG. 25 is the outer housing of the medical instrument 700, and also not shown is the frame which supports the drive mechanism elements (though parts of the frame are shown in some of the figures). The outer housing of the medical instrument 700 is shown in FIGS. 1–9.

The drive mechanism according to the preferred embodiment includes a drive train assembly 2510 for actuating the stylet 2410. The stylet 2410 is coupled to a stylet carriage assembly 2520, which itself is coupled to a drive belt (or drive band) 2530. The drive train assembly 2510 also causes indexing of the medical instrument 700, in order to move the medical instrument 700 between seed implant locations within a patient's body.

The indexing of the medical instrument 700 is accomplished by the drive train assembly 2510 causing the index lead screw 2540 to rotate, thereby causing the nut box assembly 2550 to move relative to the index lead screw 2540. The movement of the nut box assembly 2550, which is coupled to a sheath unit 780 of a targeting fixture 720, as seen in FIG. 10, for example, causes the medical instrument 700 to move relative to the targeting fixture 720, and thus to move relative to the patient's body.

The movement of the stylet 2410 is accomplished by the drive train assembly 2510 causing the stylet carriage assembly 2520 to move, by causing movement of the drive belt 2530 on which the stylet carriage assembly 2520 is coupled thereto. The times at which the stylet 2410 is moved, as well as the time at which the medical instrument 700 is indexed, are controlled based on movement of the trigger 180.

The drive train assembly 2510 also controls the amount of index movement of the medical instrument 700.

Also shown in FIG. 25 is a pitch control knob (or pitch adjustment knob) 170, which is a rotatable knob located at a proximal end of the medical instrument 700, and which can be set by an operator to control an amount of index movement of the medical instrument 700 between seed implant positions. The index movement of the medical instrument 700 is made relative to a fixed origin or fixed point in space, with that fixed point in space corresponding to the sheath unit 780 to which the medical instrument 700 is attached by way of the nut box assembly 2550.

In the preferred embodiment, the mechanism that causes the stylet carriage assembly 2520 to move within the medical instrument 700 is the drive belt 2530, which operates as a timing belt. Alternatively, the mechanism that causes the stylet carriage assembly 2520 to move may be a band with cutout slots and where those cutout slots are engaged by chains on which the band is fitted around, to provide movement of the stylet carriage assembly 2520 by way of a sprocket—chain coupling. The band may be metal, plastic or rubber, for example.

In the present invention, the drive belt 2530 is registered with pulleys on which it is provided around, to provide for precise movement of the stylet 2410 at precise moments in time (corresponding to movement of the trigger 180 of the medical instrument 700).

A drive belt is provided in the preferred embodiment because the stylet 2410 has to move practically the full length of the medical instrument 700 when the stylet 2410 is moved to thereby push a seed 2420 disposed in an extended shuttle of a seed cartridge 110, to a distal end of the needle cannula 770 that is coupled to a distal end of the medical instrument 700. Such needles may be, for example, nine inches in length, but other sizes of needles may be contemplated while remaining within the scope of the invention. The stylet 2410 needs to travel a large distance, which could be as much as eleven or twelve inches in total. This large movement of the stylet 2410 is accomplished as a result of movement of the trigger 180 from Position A to Position B. The movement of the trigger 180 is much smaller than eleven or twelve inches, and thus the drive train assembly 2510 has to cause large amount of movement of the stylet carriage assembly 2520 (as an output of the drive train assembly 2510) based on small amount of movement of the trigger 180 (as input to the drive train assembly 2510).

The provision of the drive belt 2530 that operates as a recirculating band allows for the entire movement mechanism for the stylet carriage assembly 2520 to be fully contained within the medical instrument housing, which is preferably about 8 to 12 inches in length.

Also shown in FIG. 25 is the index lead screw 2540. In the preferred embodiment, the index lead screw 2540 is a multi-start screw, and is shown in FIG. 25 without the threads for simplicity (but see FIG. 47).

In the preferred embodiment, the index lead screw 2540 is a four-start screw, with four separate threads that are provided along the outer circumference of the index lead screw 2540 in a helical manner. The provision of a multi-start index lead screw allows for more movement of the index lead screw 2540 per each revolution, as compared to a single-start index lead screw. Alternatively, the index lead screw 2540 may have less or more than four starts, such as having one start or having six starts.

Figure 51:
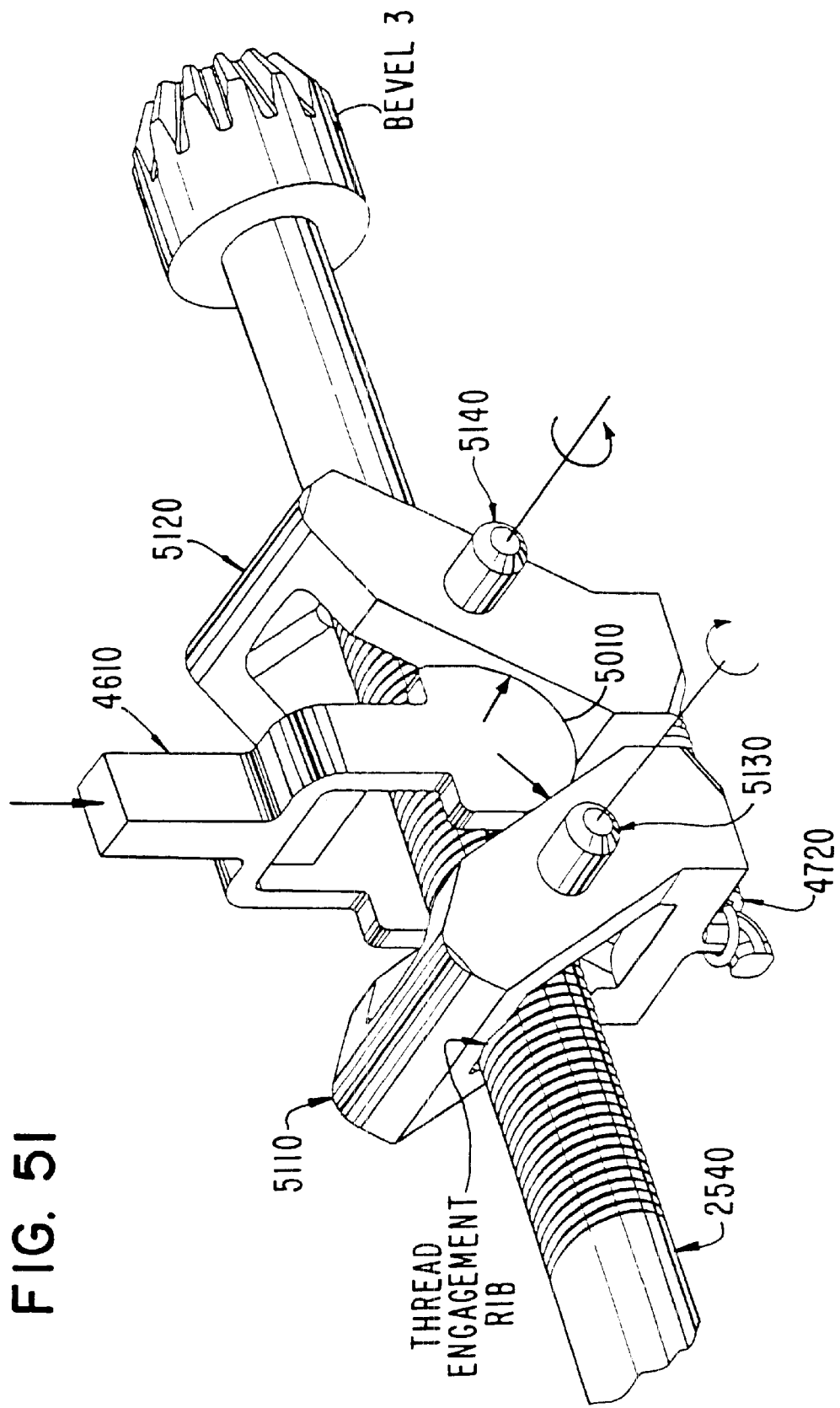
FIG. 51 is a top perspective view of components of the nut box assembly that are coupled to the index lead screw, with the outer housing of the nut box assembly removed for clarity, according to the preferred embodiment of the invention.

Also shown in FIG. 25 is the nut box assembly 2550, which contains two nuts 5110, 5120. Each of the two nuts 5110, 5120 of the nut box assembly 2550 individually rotates about their own center line 5130, 5140. FIG. 51 shows the two nuts 5110, 5120 and the axes (or center lines) 5130, 5140 which they respectively rotate around.

Figure 46:
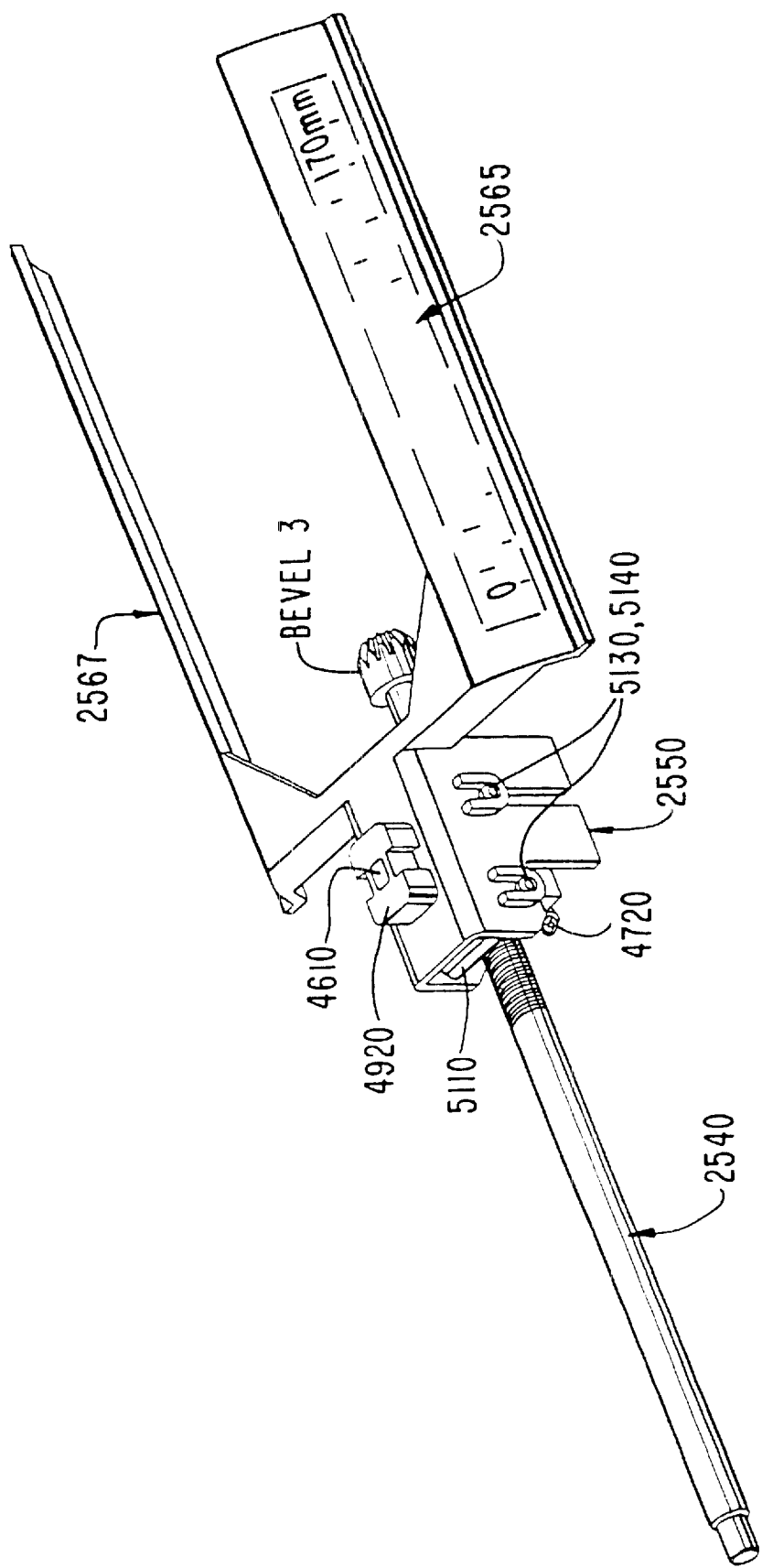
FIG. 46 a blow-up of the indexing mechanism according to the preferred embodiment of the invention, which includes a nut box and an index lead screw 2540.
Figure 47:
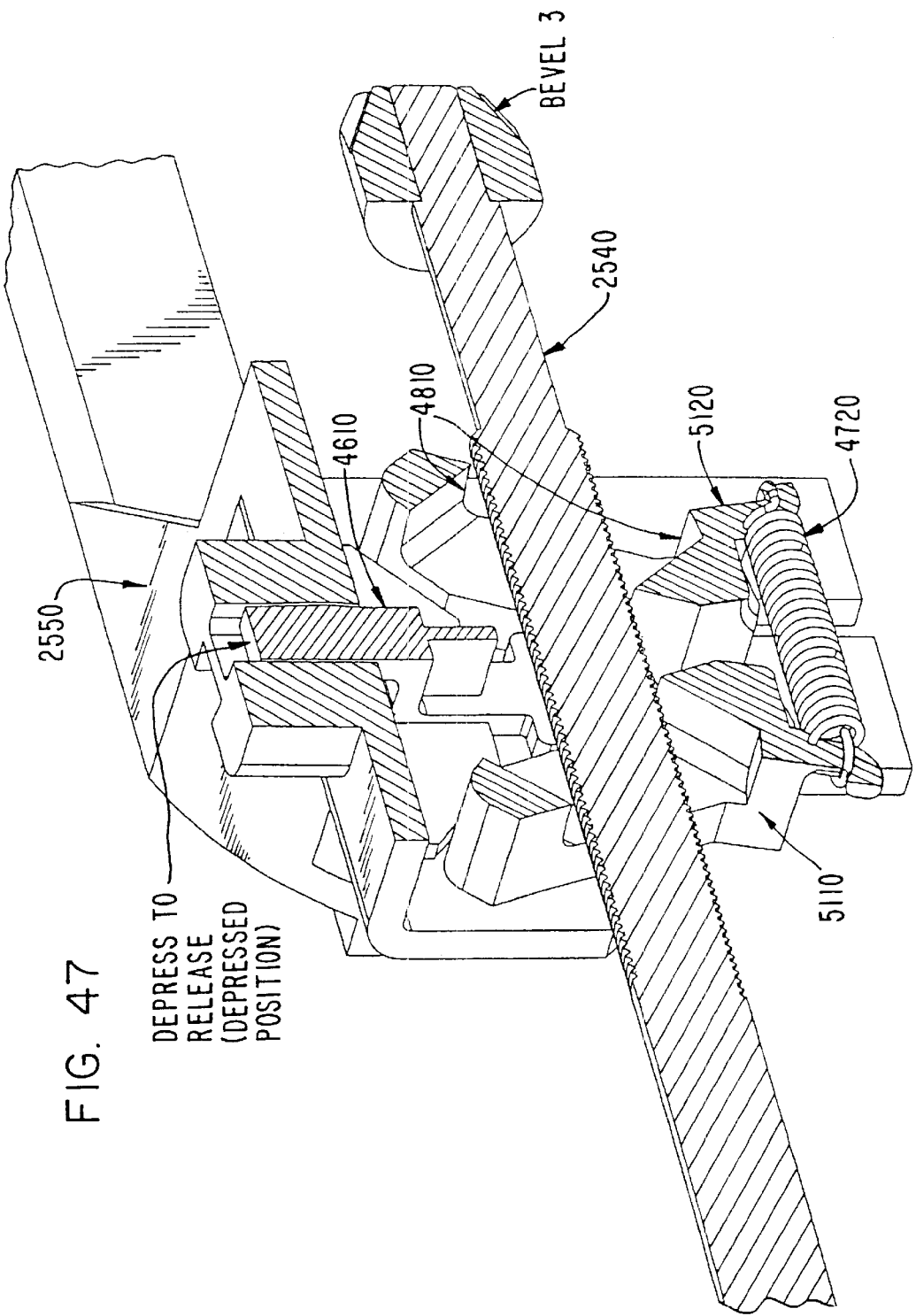
FIG. 47 shows an ISO section view of the indexing mechanism in the release position, according to the preferred embodiment of the invention.
Figure 49:
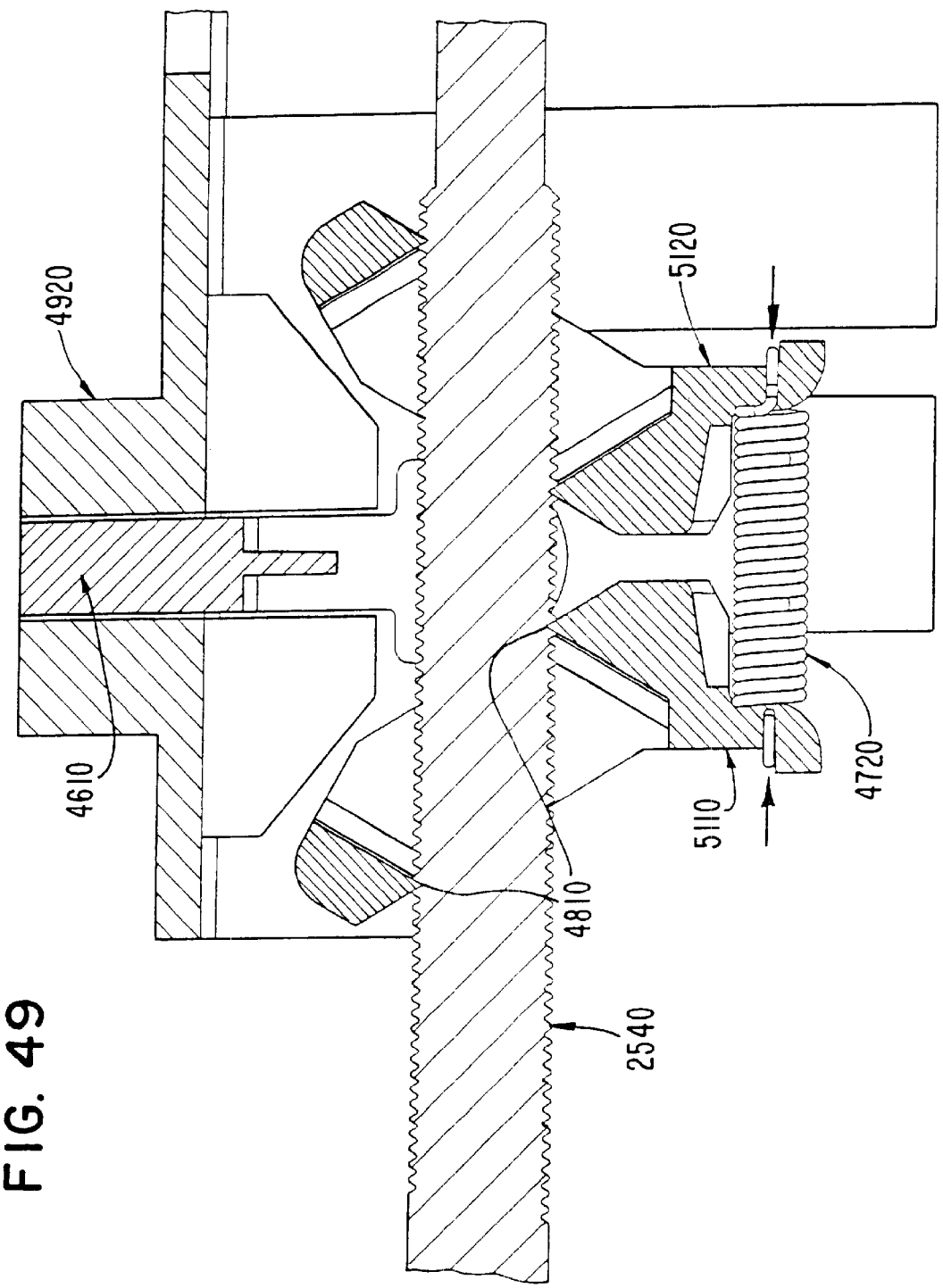
FIG. 49 shows a section view of the indexing mechanism in the lock position, according to the preferred embodiment of the invention.
Figure 50:
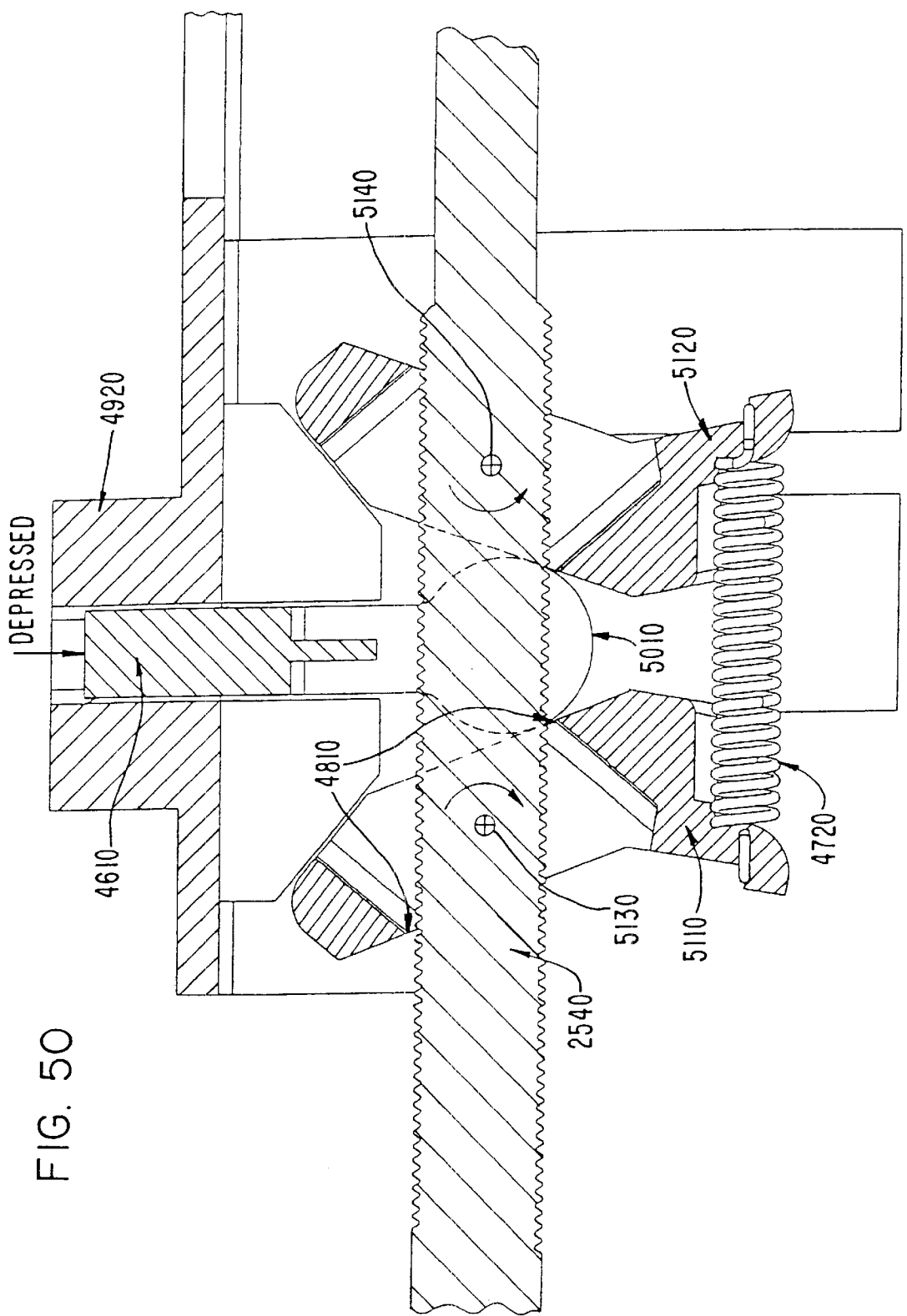
FIG. 50 shows a section view of the indexing mechanism in release position, according to the preferred embodiment of the invention.

At the top of the nut box assembly 2550 there is provided a rectangular feature, called a nut release cam 4610, which is seen best in FIGS. 46 and 47. The nut release cam 4610 is surrounded by the nut box housing 4920 at the top portion of the nut box assembly 2550, as seen in FIG. 49. When the nut release cam 4610 is pushed downwards, due to actuation of button 793 on the sheath unit 780 (see FIG. 10), the two nuts 5110, 5120 of the nut box assembly 2550 rotate (around their respective pivot points 5130, 5140) so as to be separated from the index lead screw 2540, thereby allowing the nut box assembly 2550 to be moved without engaging the index lead screw 2540. As seen in FIG. 46, the housing at the top of the nut box assembly 2550 that surrounds the nut release cam 4610 is coupled to a sheath unit 780 of a targeting fixture 720 (see FIG. 10), whereby actuation of the button 793 on the sheath unit 780 causes the nut release cam 4610 to be pushed downwards, so that the nut box assembly 2550, and thus the medical instrument 700, can be moved manually relative to the sheath unit 780.

The present invention is also applicable to other types of units for coupling the medical instrument to a targeting fixture, such as the one described in GRID SHEATH FOR MEDICAL INSTRUMENT, which is incorporated in its entirety herein by reference.

In particular, the nut box housing 4920 at the top of the nut box assembly 2550 fits into a similarly-shaped female member (not shown) on the sheath unit 780 of the targeting fixture 720. When the nut release cam 4610 is engaged, the nut box assembly 2550 is separated from the index lead screw 2540 of the medical instrument 700.

In the process of moving the trigger 180 from Position B to Position C, the drive train assembly 2510 causes the index lead screw 2540 to rotate, which causes the medical instrument 700 to move relative to the sheath unit 780 when the nut box assembly 2550 is engaged with the threads of the index lead screw 2540, since the nut box assembly 2550 and thereby travels along the threads of the index lead screw 2540 as the index lead screw 2540 rotates. During this time, the nut box assembly 2550 is still attached to the sheath unit 780 and has not moved relative to the sheath unit 780, but the medical instrument 700 has indexed due to the distal movement of the nut box assembly 2550 within the medical instrument 700.

Also shown in FIG. 25 are wing elements on the nut box assembly 2550. These features can be seen best as wing elements 2565, 2567 in FIG. 46. Referring to FIG. 46, the wing elements 2565, 2567 have distance markings printed thereon, to provide a visual indicator to an operator of how far the nut box assembly 2550 (and thus the needle cannula 770 and the medical instrument 700) has moved with respect to a "zero" or reference position. The markings can be either metric (mm) or non-metric (inch). The markings on the wing elements 2565, 2567 are positioned beneath windows 150A and 150B on the right and left sides of the medical instrument 700, respectively, as shown in FIGS. 1 and 2, for example. This allows an operator to clearly view the current position of the medical instrument 700 with respect to a reference position.

As shown in FIG. 1, the handle 705 of the medical instrument 700 includes a trigger 180, which, when engaged, provides an input force to be used by the drive train assembly 2510 to cause a particular action, such as index movement of the medical instrument 700 or movement of the stylet 2410. The handle 705 is preferably a plastic part, like the rest of the outer housing of the medical instrument 700 (see FIGS. 1–9). The trigger 180 is preferably a plastic part with a metal trigger insert 2585, so as to withstand the load due to the trigger return spring 2581, as seen in FIG. 25.

Figure 26:
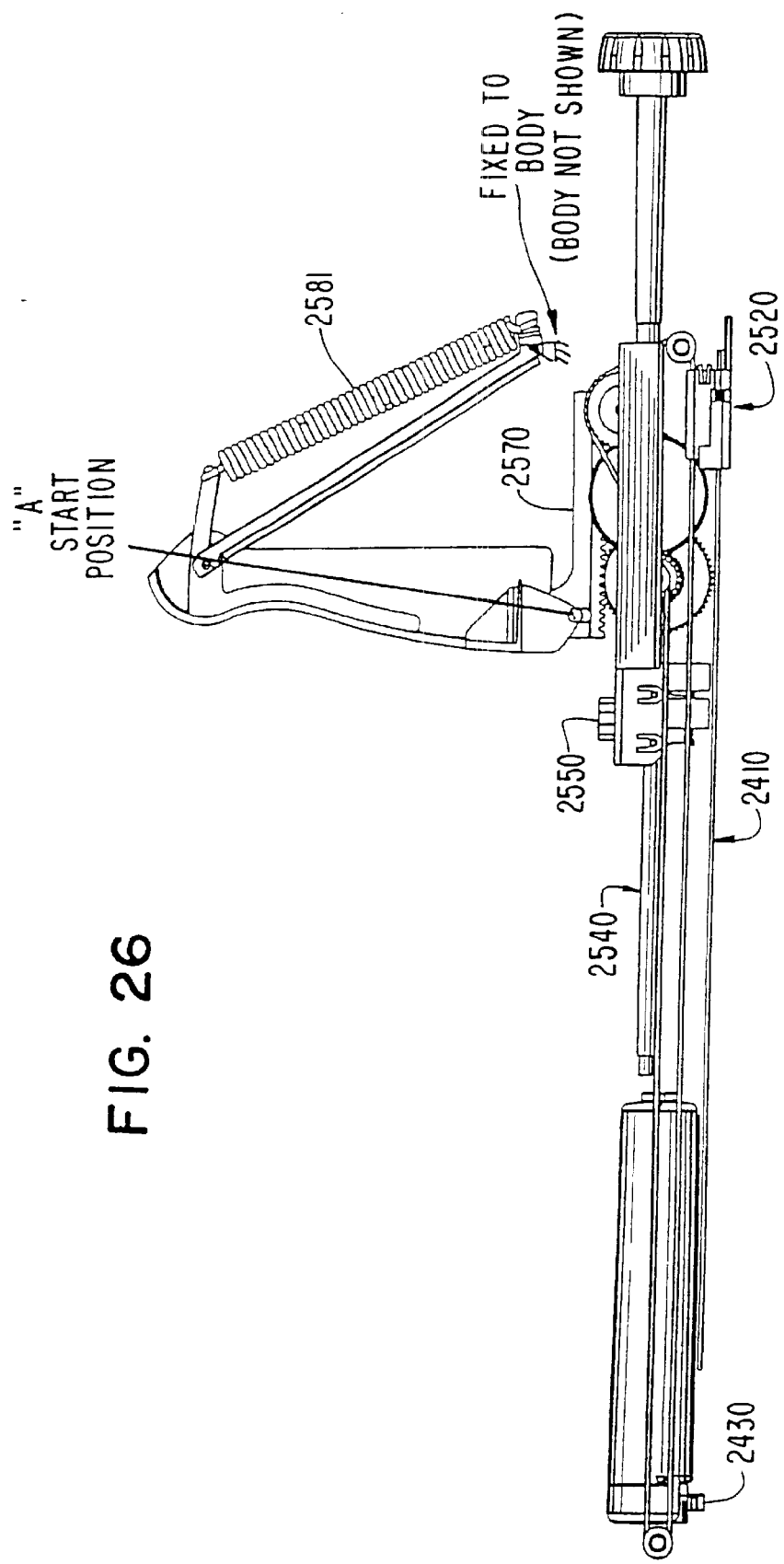
FIG. 26 is a side view of the medical instrument (with the outer housing removed) with the trigger in start position A.

The bottom end of the trigger strut 2583 is fixed to the housing of the medical instrument 700 inside the handle 705, and that fixing provides a fixed reference point for the trigger return spring 2581. FIG. 26 also shows the fixing of one end of a trigger strut 2583 to the body of the medical instrument 700. Also coupled to the trigger 180 is a trigger insert 2585. The trigger strut 2583 is provided so that all of the high force loads of the trigger return spring 2581 are mostly contained within a triangle formed by the trigger insert 2585, the trigger strut 2583, and the trigger return spring 2581. The trigger insert 2585 operates as a linkage, with its center pivot point coupled to the trigger strut 2583.

Also shown in FIG. 25 is a drive rack 2570, which moves linearly in accordance with movement of the trigger 180. The drive rack 2570 engages with the drive train assembly 2510, and provides an input force to the drive train assembly 2510. FIG. 25 shows the trigger 180 in its home position A.

As the trigger 180 is moved from position A to position C, the drive rack 2570 moves linearly in a proximal direction with respect to the drive train assembly 2510. FIG. 26 shows the teeth on the bottom surface of the drive rack 2570, which engage a gear of the drive train assembly 2510, as seen best in FIG. 34.

Referring now to FIG. 26, the drive rack 2570 is shown in its home position that corresponds to the trigger 180 being at position A. In this position, the stylet carriage assembly 2520 is also in its rest position, which corresponds to its most proximal position within the housing of the medical instrument 700.

To be explained in more detail later, in the rest position the stylet 2410 is separated from the shuttle 2430 of the cartridge 110 by a small distance, or spacing, which is referred to as "lost motion distance" or "stylet offset start dimension". The shuttle 2430 is shown in its extended position in FIG. 26. This spacing is provided in order to allow for resetting of the shuttle 2430 for obtaining a seed from the cartridge 110 for a next seed implant.

The shuttle 2430 is caused to extend from the cartridge 110 by actuation of a seed loading button 185 (see FIG. 1) on the medical instrument 700. When the seed loading button 185 is actuated, the shuttle 2430 extends downwards, so that a seed being held within the shuttle 2430 is placed directly in the path of the stylet 2410 when the stylet 2410 is moved distally. That allows for the seed to be pushed all the way to a distal end of a needle cannula 770 that is also coupled to the medical instrument 700 (see FIG. 24, for example).

Figure 27:
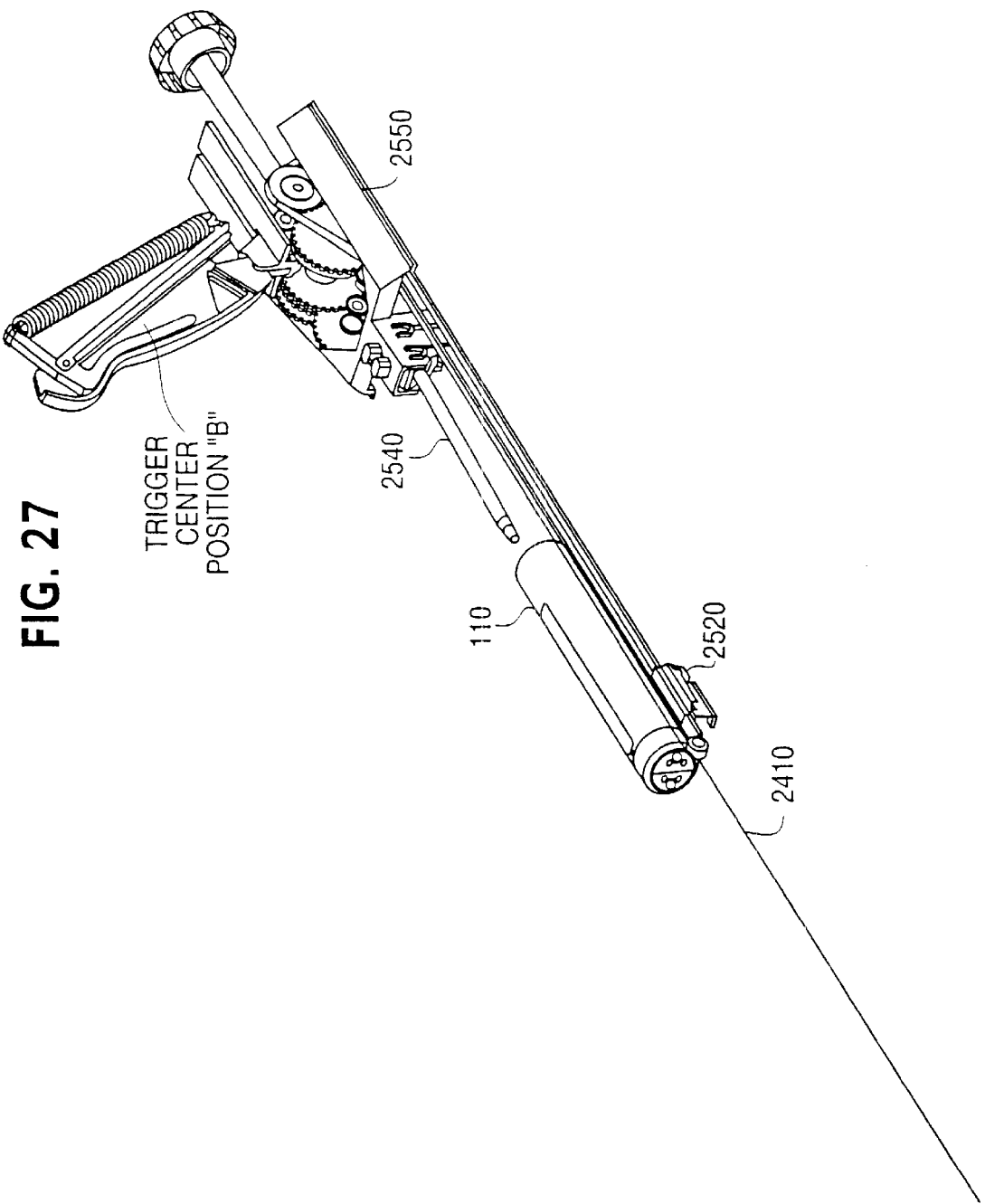
FIG. 27 is a top perspective view of the medical instrument (with the outer housing removed) with the trigger in center position B and with the stylet 2410 shown in its fully extended position.

FIG. 27 shows the trigger 180 in position B, which corresponds approximately to a central position of the trigger 180 between its home position A and its fully extended position C. Movement of the trigger 180 from position A to position B causes the stylet carriage assembly 2520, and thus the stylet 2410, to move from its most proximal position to its most distal, fully-extended position within the housing of the medical instrument 700.

Figure 28:
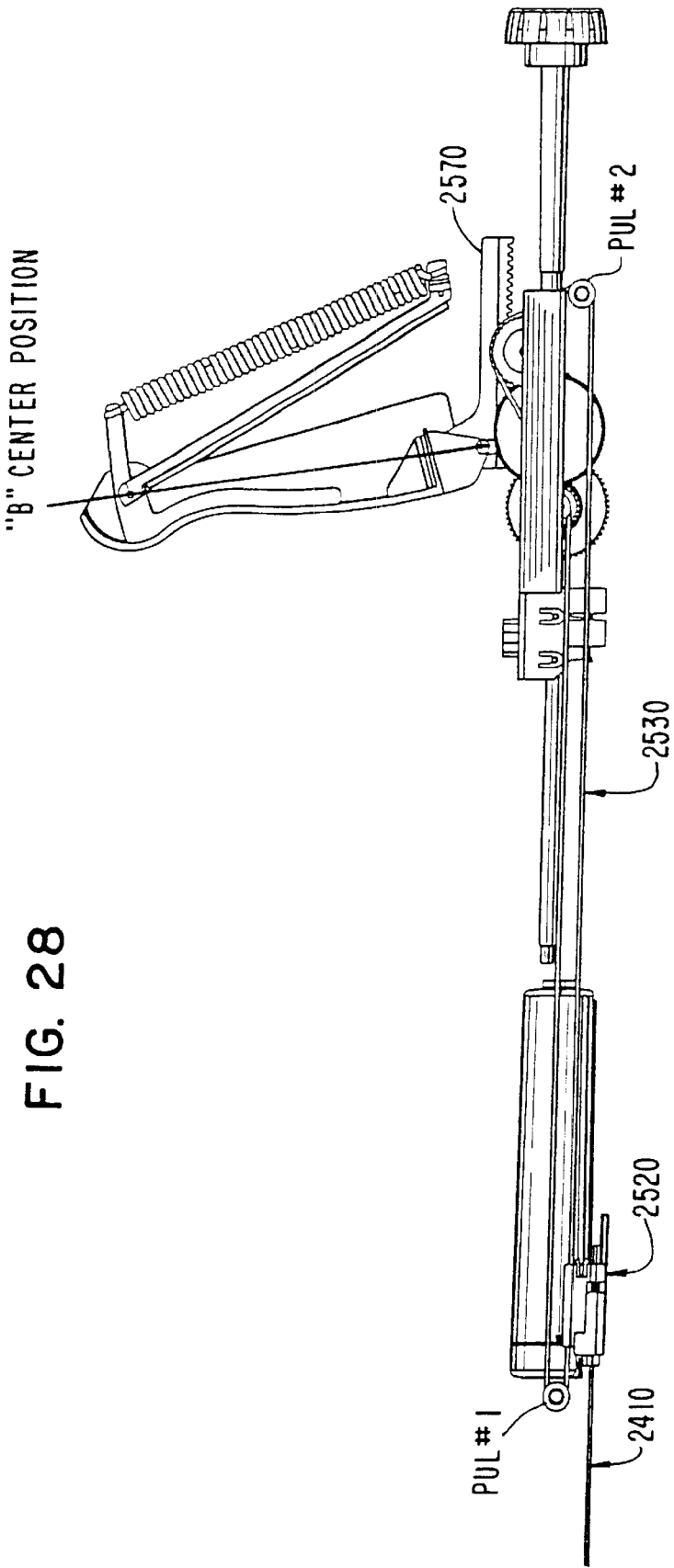
FIG. 28 is a side view of the medical instrument (with the outer housing removed) with the trigger in center position B.

FIG. 28 is a side view of the medical instrument 700, with the outer housing removed for clarity, in which the trigger 180 is shown in position B. Comparing FIG. 28 to FIG. 26, the linear movement in a proximal direction of the drive rack 2570 can be seen, due to the trigger 180 being moved from position A to position B.

FIG. 28 also shows the drive belt 2530, which is fitted around a distal pulley (PUL#1) and a proximal pulley (PUL#2). The stylet carriage assembly 2520 is shown at its most distal position, which is a result of the moving of the trigger 180 from position A to position B.

Figure 29:
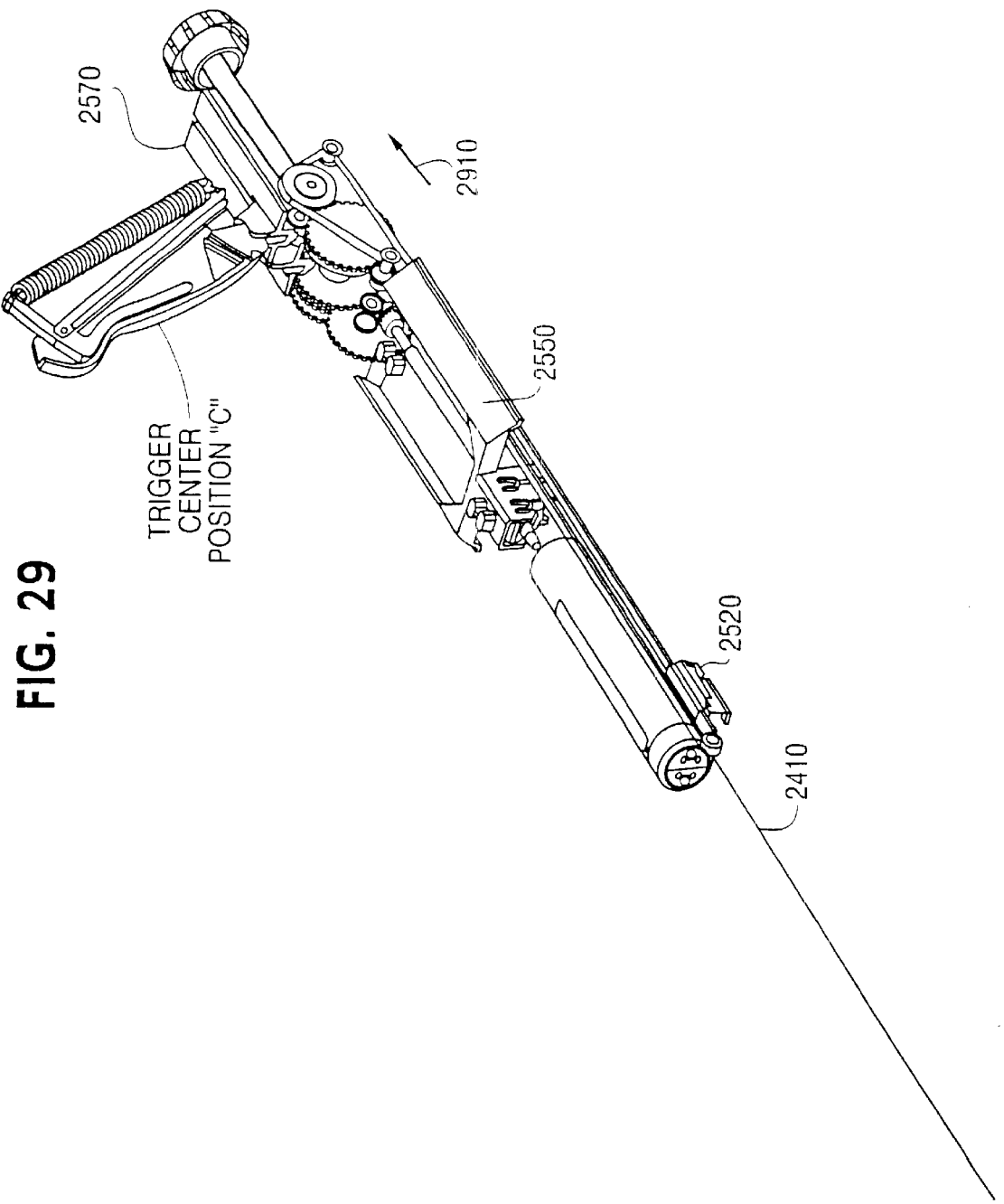
FIG. 29 is a top perspective view of the medical instrument (with the outer housing removed) with the trigger in end position C.

FIG. 29 shows the trigger 180 at position C, which is the fully extended position. Due to the movement of the trigger 180 from position B to position C, the stylet carriage assembly 2520 has not moved from its most distal position within the housing of the medical instrument 700, and the medical instrument 700 has indexed a preset amount due to the nut box assembly 2550 moving forward along the index lead screw 2540 due to the rotation of the index lead screw 2540. The arrow 2910 in FIG. 29 shows the direction of movement of the medical instrument 700, due to the movement of the nut box assembly 2550. Since the nut box assembly 2550 is affixed to the sheath unit 780 of a targeting fixture 720 (see FIG. 10) during a seed implanting procedure, the nut box assembly 2550 remains fixed in position with respect to the sheath unit 780. However, since the nut box assembly 2550 has moved forward along the slot 127 (see FIG. 1) on the medical instrument 700, the medical instrument 700 indexes away from the patient. As the trigger is moved from position B to position C, while the nut box assembly 2550 moves forward, the stylet 2410 remains stationary in the fully extended position.

In FIG. 29, the nut box assembly 2550 is shown at its most extended, or most distal position, with respect to the medical instrument 700. Referring now to FIG. 1, the nut box assembly 2550 is shown at its most proximal position within the slot 127 on top of the medical instrument 700. The position of the nut box assembly 2550 shown in FIG. 29 is achieved after multiple trigger cycles, since the slot 127 is sized to handle a large-sized prostate length, and thus several seed implants may be performed within the prostate over that length.

Figure 30:
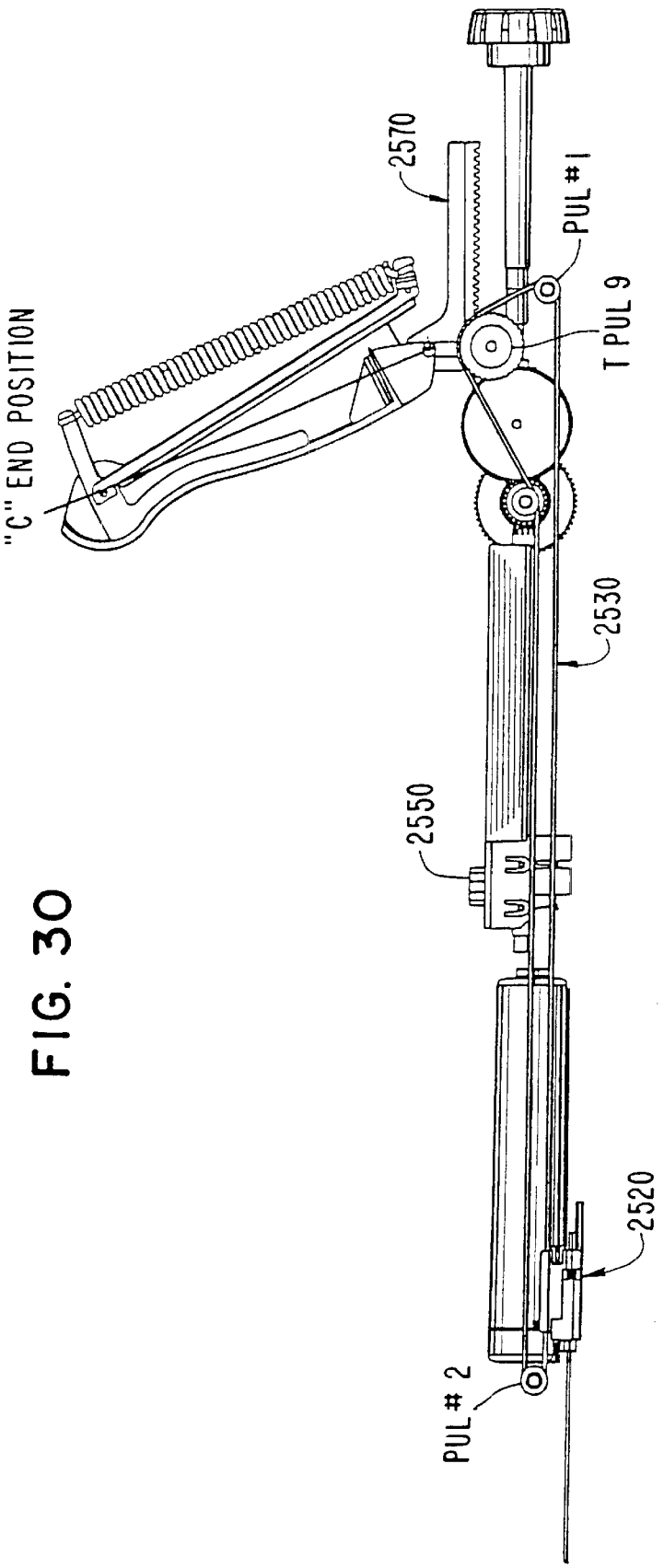
FIG. 30 is a side view of the medical instrument (with the outer housing removed) with the trigger in center position C.

FIG. 30 shows a side view of the trigger 180 at position C. FIG. 30 also shows that the drive belt 2530 is fitted around a distal pulley PUL#1, a proximal pulley PUL#2, and a drive gear pulley TPUL9. The drive train assembly 2510 causes rotation of gear TPUL9 when the trigger 180 is moved from position A to position B, which causes the stylet carriage assembly 2520 to move in a distal direction within the medical instrument 700. This will be explained later in more detail.

Figure 31:
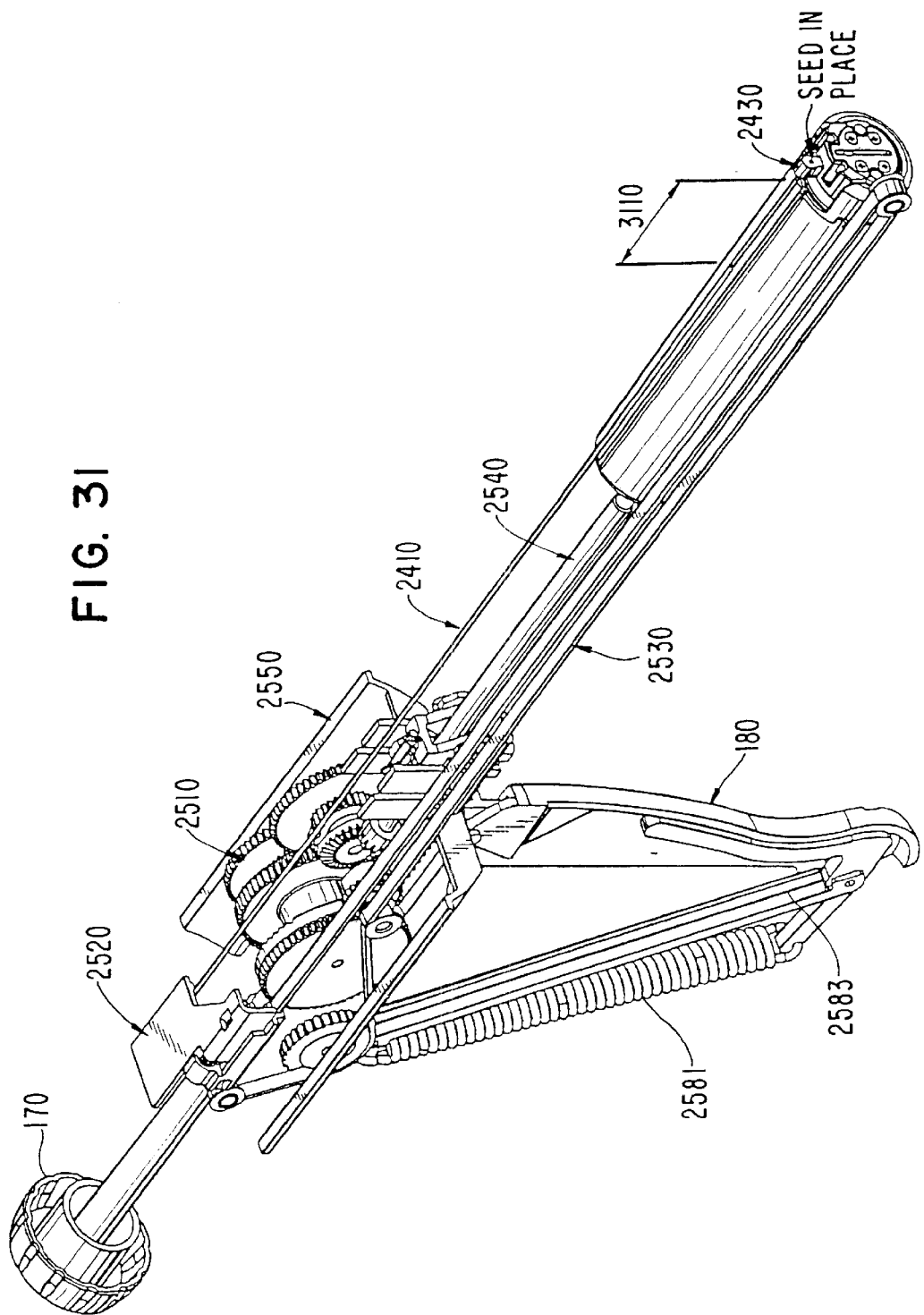
FIG. 31 is a bottom perspective view of the medical instrument (with the outer housing removed) with the trigger at start position A.

FIG. 31 shows a bottom view of the medical instrument 700, with the outer housing and frame removed to more clearly show some of the elements within the medical instrument 700. The trigger 180 is in position A in FIG. 31. The stylet offset start dimension, or lost motion distance 3110, is shown in FIG. 31. A seed is in place within the extended shuttle 2430 of the seed cartridge 110, waiting for the stylet 2410 to push it in a direction towards the needle cannula 770 (not shown in FIG. 31, but see FIG. 32).

Figure 32:
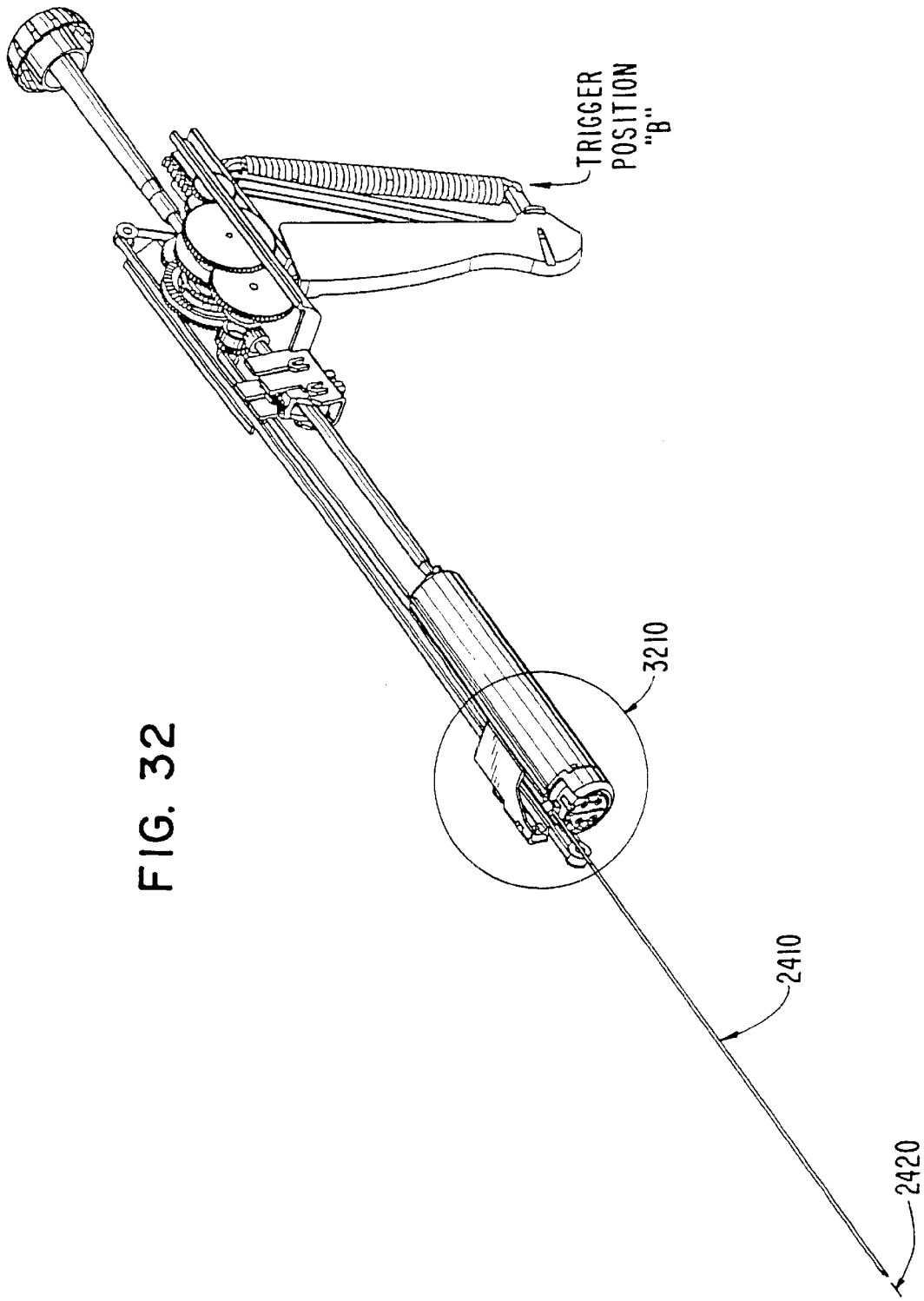
FIG. 32 is a bottom perspective view of the medical instrument (with the outer housing removed) with the trigger at center position B.

FIG. 32 shows a bottom view of the medical instrument 700, similar to FIG. 31, but with the trigger 180 at position B. The stylet 2410 has moved to its most distal position due to movement of the trigger 180, and a seed 2420 that is being pushed distally by the stylet 2410 is also shown in FIG. 32. Note that the stylet 2410 extends through the extended shuttle 2430, which can be seen more clearly in FIG. 33.

Figure 33:
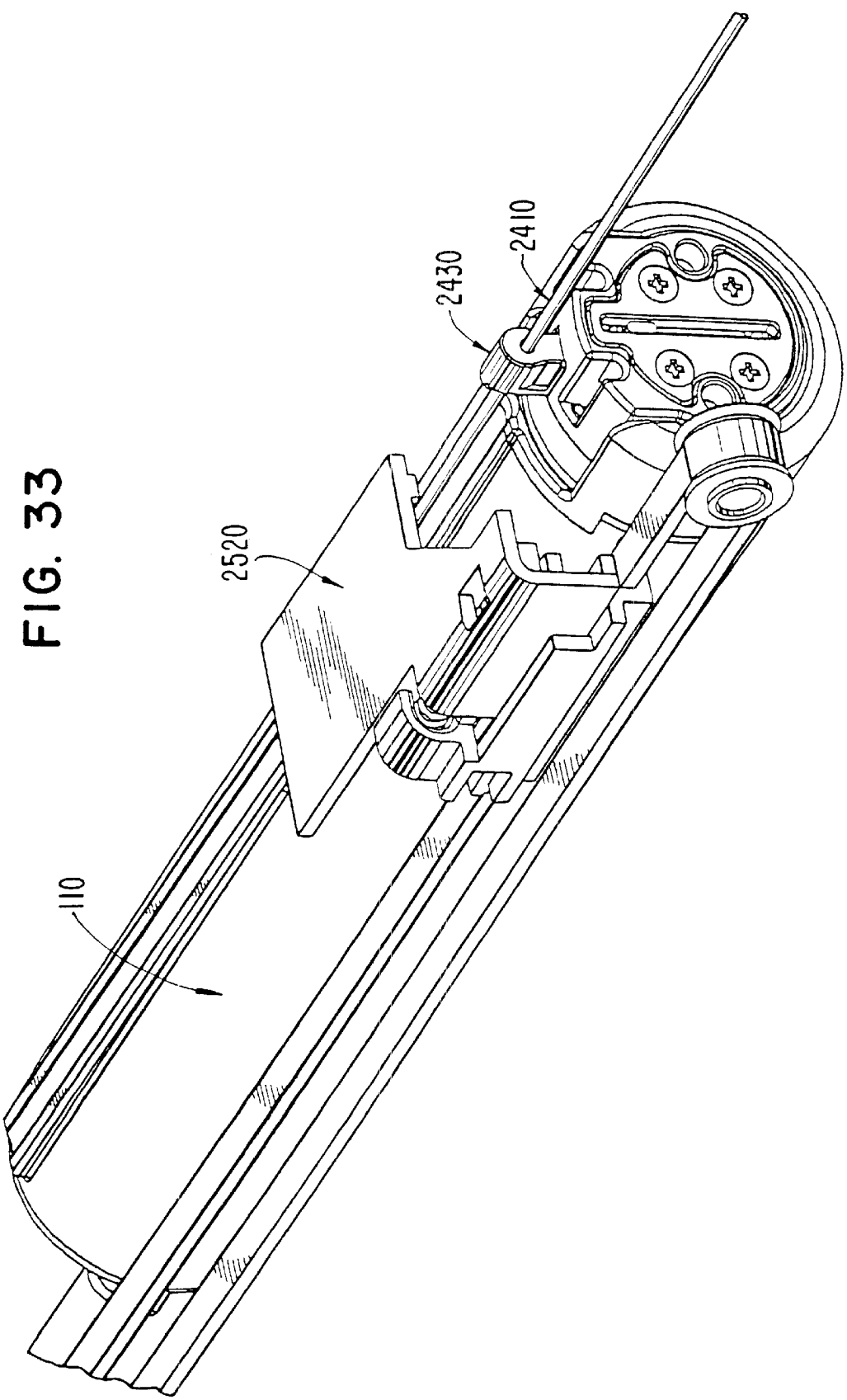
FIG. 33 is a blow-up of the circled portion of the view shown in FIG. 32.

FIG. 33 shows a blow-up view of the encircled region 3210 of FIG. 32. The stylet 2410 is shown passing through a seed accepting hole of the shuttle 2430, whereby the stylet 2410 picks up a seed in the seed accepting hole of the shuttle 2430 and pushes it to a distal end of the needle cannula 770.

Figure 45:
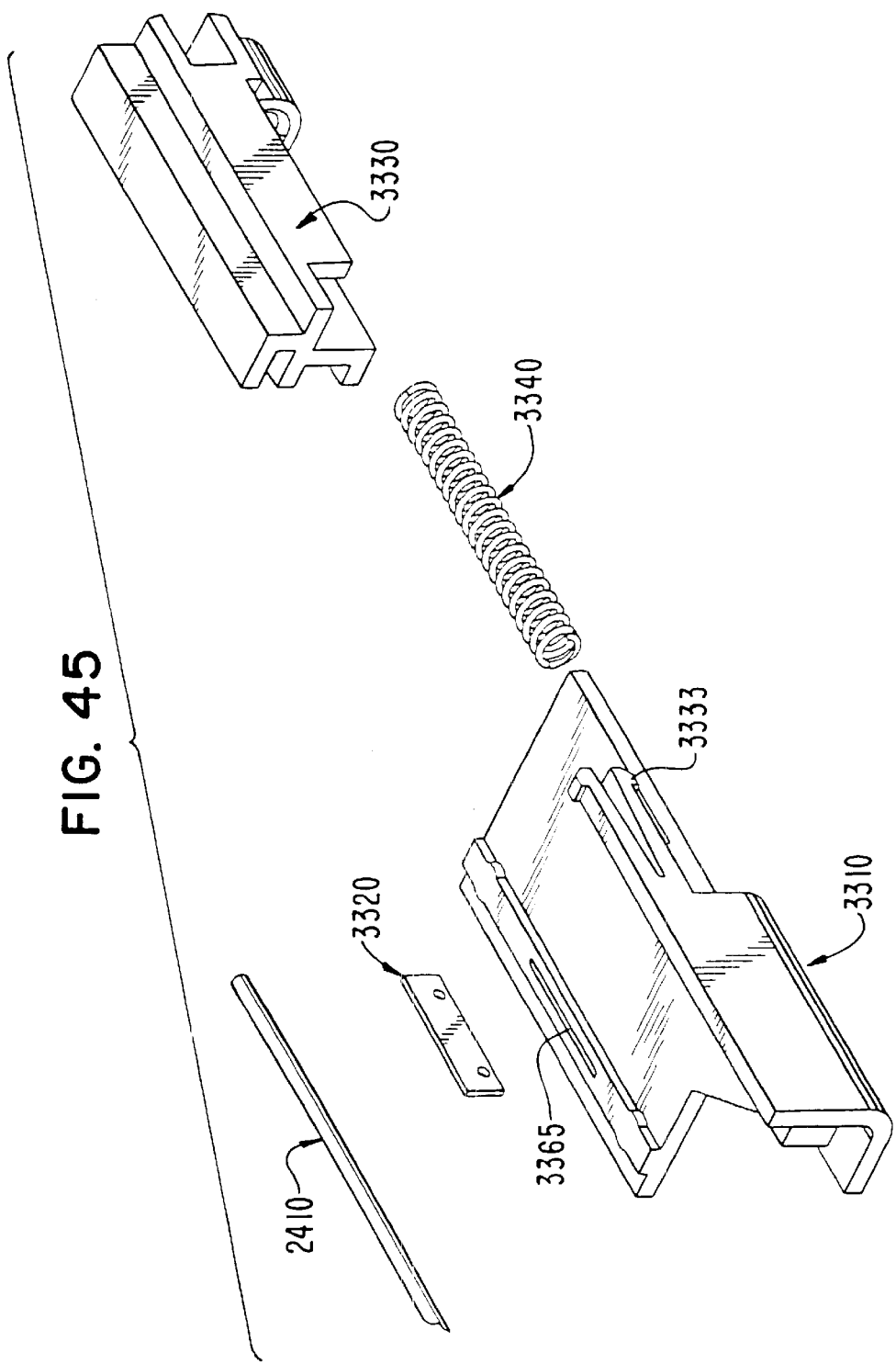
FIG. 45 shows an exploded view of the stylet carriage assembly, according to the preferred embodiment of the invention.

Also shown in more detail in FIG. 33 is the stylet carriage assembly 2520, which is made up of four main components, shown in detail in FIG. 45. The four main components include a carriage portion 3310 (having a flat lower surface) that slides along an inner frame portion (not shown) of the medical instrument 700, a tab 3320 for attachment to the stylet 2410, a belt clamp 3330 that attaches to the drive belt 2530, and a spring 3340. FIG. 45 shows these elements separated from each other, to clearly show each element and how it is coupled to the other elements of the stylet carriage assembly 2520. The carriage portion 3310 includes a snap retainer 3333 for coupling to the belt clamp 3330.

When the stylet carriage assembly 2520 is moved to its most distal position due to movement of the trigger 180 from position A to position B, the flat lower surface of the carriage portion 3310 comes into contact with a stop (not shown) on the frame within the medical instrument 700, so as to place the stylet carriage assembly 2520 (and thus the stylet 2410) at a precise position when it is moved to its most distal position. That way, a seed is placed at a precise location at the distal end of the needle cannula 770. The spring 3340 accounts for any inaccuracies or backlash in the driving of the stylet carriage assembly 2520 to its most distal position.

In more detail, the belt clamp 3330 is driven slightly past (e.g., about 0.030" to 0.25" past, wherein the overdriving amount is not limited to this range in the present invention) a fixed position corresponding to its most distal position. Due to the stop on the inner frame of the medical instrument 700, the carriage portion 3310 only goes to the fixed position, with the spring 3340 taking up the slack due to the slight overdriving of the belt clamp 3330. This assures that the stylet 2410 is always brought to the fixed, most distal position, each time the trigger 180 is moved from position A to position B. As the carriage portion 3310 hits the stop on the inner frame of the medical instrument 700, that contact the spring 3340 of the stylet carriage assembly 2520. The compression of the spring 3340 takes up the extra distance caused by overdriving the belt clamp 3330.

The stylet 2410 is attached to the tab 3320, preferably by welding them together. The tab 3320 is inserted onto a slot 3365 on the carriage portion 3310, to thereby hold the stylet 2410 onto the carriage portion 3310 (see FIG. 45). The carriage portion 3310 is then snapped onto the belt clamp 3320 by way of the snap retainer 3333, with the spring 3340 provided therebetween for overdrive protection.

Figure 34:
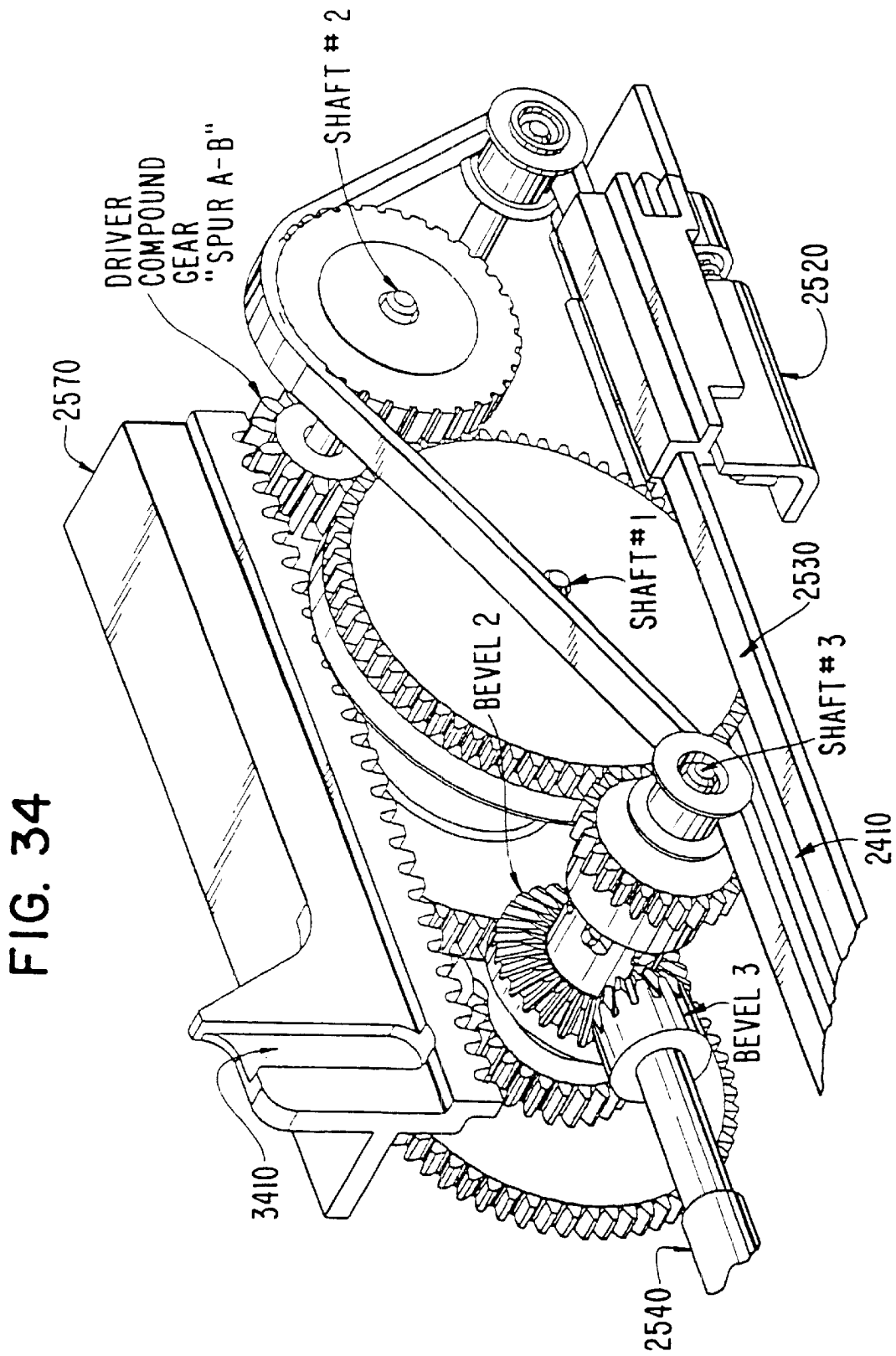
FIG. 34 is a blow-up of the drive rack and drive gear interface within the medical instrument.

Now, description of the drive train assembly 2510 of the medical instrument 700 will be made in detail. FIG. 34 shows a cutaway section of the drive train assembly 2510, with the drive rack 2570 seated above it.

The drive train assembly 2510 is operable so as to take a small amount of movement of the trigger 180, say one to two inches, and use that movement to cause various actions to occur, such as stylet movement and indexing of the medical instrument 700. In other words, the drive train assembly 2510 is operative to take a small input and provide a large output. This is possible since the output force requirement is relatively low, since a low-weight seed has to be pushed by the stylet 2410 as the trigger 180 moves from position A to position B. Also, the drive train assembly 2510 has to dwell the stylet 2410 at its most distal position as the trigger 180 moves from position B to position C, while at the same time causing indexing (movement) of the medical instrument 700 relative to the patient. Also, the drive train assembly 2510 has another input, a variable pitch adjustment value, which allows the medical instrument 700 to be indexed by an operator-chosen amount, when the trigger 180 is moved from position B to position C. All of these features are accomplished by the drive train assembly 2510, making it a very important part of the medical instrument 700.

In the preferred embodiment, five different pitch values are available to choose from by way of the pitch adjustment knob 170 being moved to a desired position. Of course, other numbers of pitch values may be contemplated while remaining within the scope of the invention.

FIG. 34 also shows the drive rack 2570 and how it interfaces with the drive train assembly 2510. Movement of the trigger 180 causes linear movement of the drive rack 2570. The drive rack 2570 includes a slot 3410 on which the trigger 180 fits, so that the drive rack 2570 moves with movement of the trigger 180. In particular, the slot 3410 of the drive rack 2570 receives a pin (not shown) that protrudes out from the trigger 180. That way, when the trigger 180 is swung through an arc, it translates vertically relative to drive rack 2570. The drive rack 2570 only moves in a linear fashion as a result of the movement of the trigger 180. As the trigger 180 is stroking through its arc, the pin of the trigger 180 is moving vertically up and down in the slot 3410.

As the drive rack 2570 moves linearly in a proximal direction with respect to the medical instrument housing, the drive compound gear Spur A-B moves in a clockwise direction as shown in FIG. 34. This movement is a result of the trigger 180 moving from position A to position B.

Figure 35:
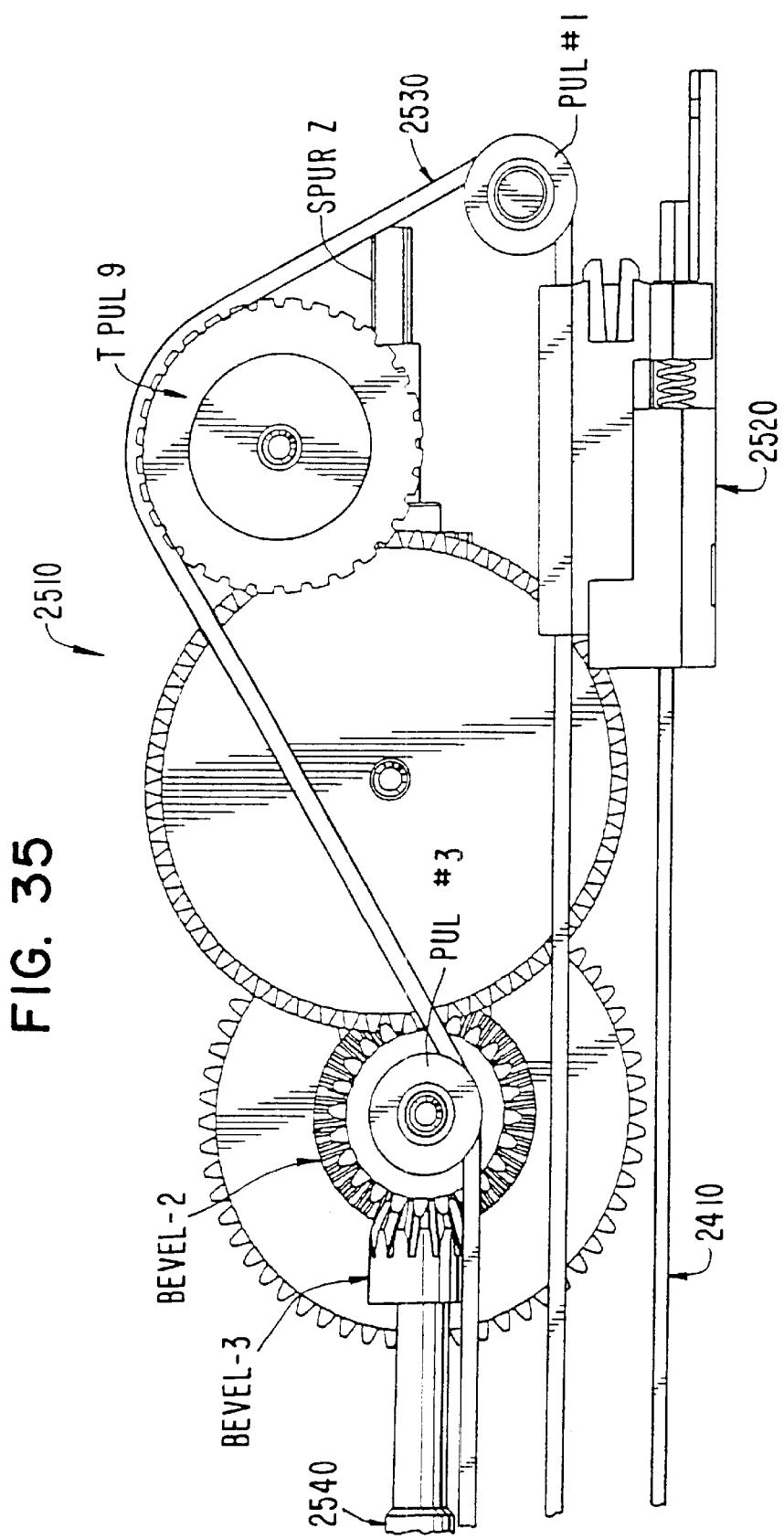
FIG. 35 is a left-side view of the drive rack and drive gear interface.

Also shown in FIG. 34 as well as FIG. 35 is the drive belt 2530, which is fitted beneath an idler pulley #3 (PUL#3), above a gear TPUL9, and around an idler pulley #1 (PUL#1). Idler pulleys PUL#1, PUL#2 and PUL#3 (see also FIG. 41) are provided so as to provide the proper amount of tension on the drive belt 2530.

Gear Spur A-B is free to rotate along the shaft #2 (see also FIG. 37) that it is coupled to, so that rotation of gear Spur A-B does not result in rotation of shaft #2. In other words, gear Spur A-B is not registered or keyed with the shaft #2.

FIG. 34 also shows a bevel gear Bevel-3 coupled to the index lead screw 2540, whereby the gear Bevel-3 is coupled to a gear Bevel-2 of the drive train assembly 2510. Alternatively, a face gear can be coupled to the index lead screw 2540 instead of the bevel gear. The linear movement of the drive rack 2570, caused by the trigger 180 being moved from position A to position B, results in rotation of gear Spur A-B, which results in rotation of gear TPUL9. The rotation of gear TPUL9 results in the drive belt 2530 to move clockwise, thereby causing the stylet carriage assembly 2520 to move distally.

The drive train assembly 2510 maintains proper sequencing and timing during movement of the trigger 180 from position A to position B to position C, and back to position A (via position B). The precise way this is done is described in detail below.

FIG. 35 shows a left side view of the drive train assembly 2510, whereby the pitch adjustment gear Spur-Z can be seen at the proximal end of the medical instrument 700. By rotating gear Spur-Z, which is caused by rotation of the pitch adjustment knob 170 on the medical instrument 700, an operator can select an index amount for the medical instrument 700 between seed implant locations.

Figure 36:
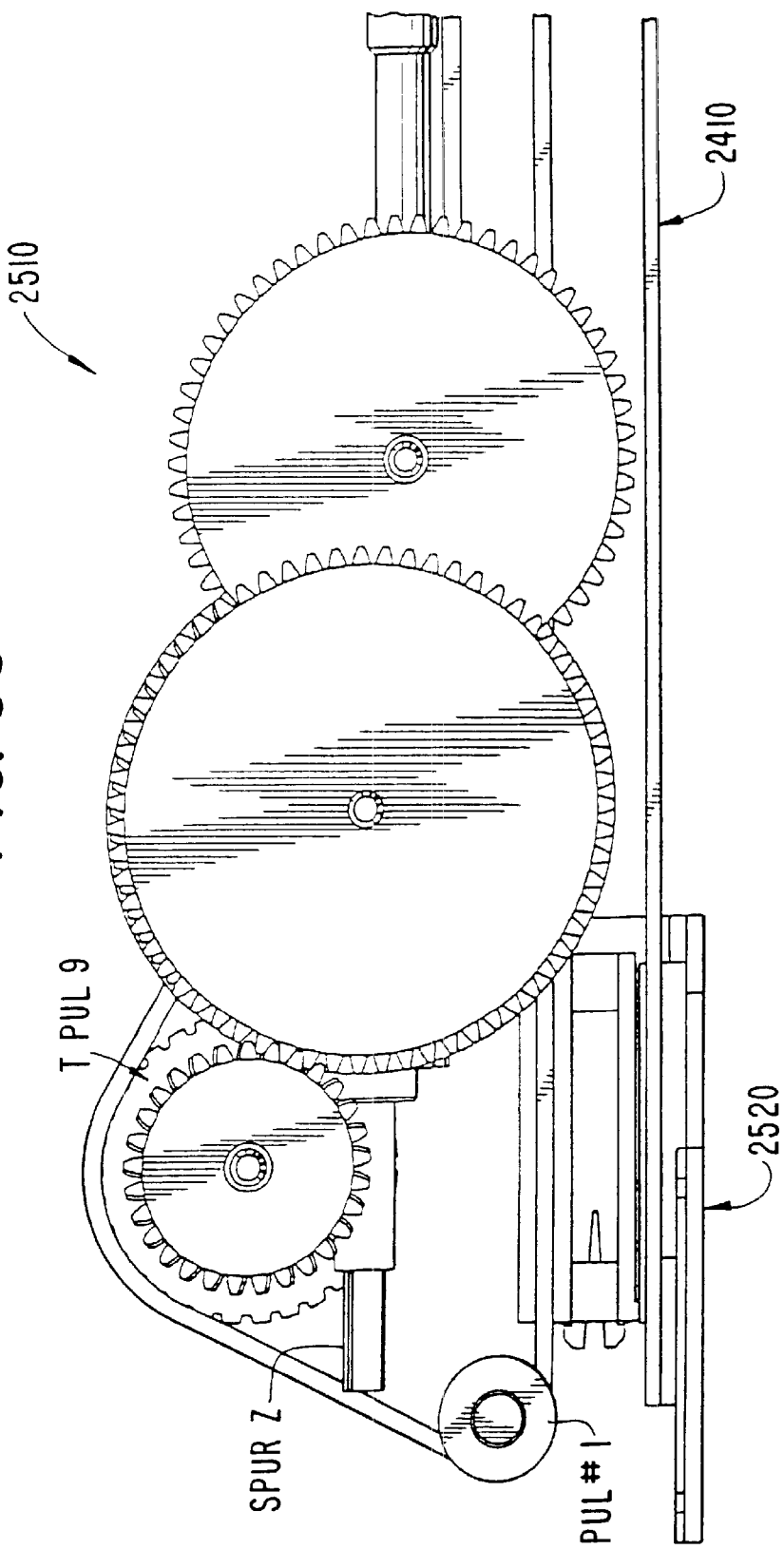
FIG. 36 is a right-side view of the drive rack and drive gear interface.

FIG. 36 shows a right side view of the drive train assembly 2510, whereby a right side view of the stylet carriage assembly 2520 is also shown in that figure. The drive rack 2570 is not shown in FIGS. 35 and 36 in order to better show the features of the drive train assembly 2510.

Figure 37:
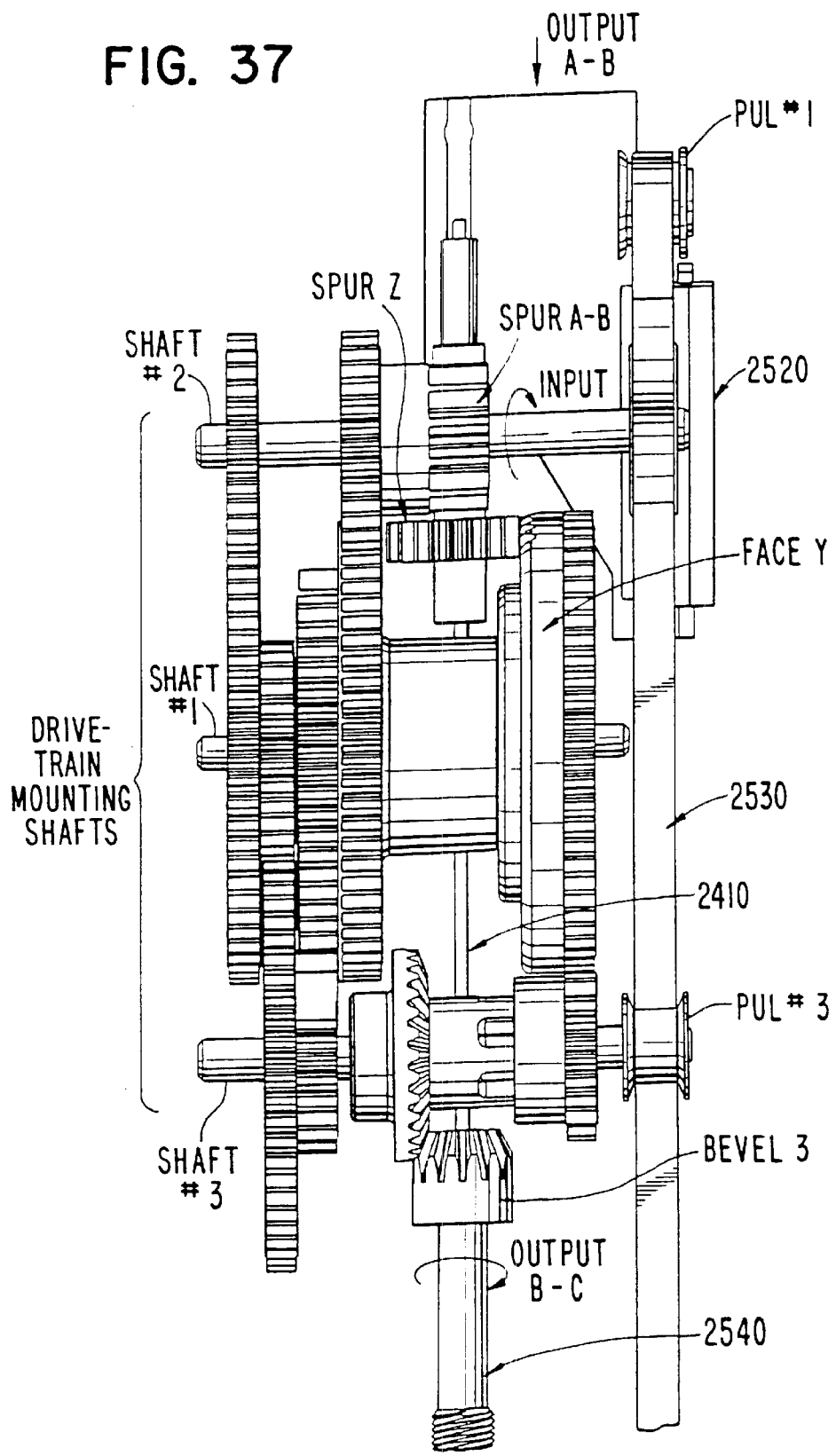
FIG. 37 is a top view of the drive train assembly, according to a preferred embodiment of the invention.

FIG. 37 is a top view of the drive train assembly 2510. The drive train assembly 2510 includes three shafts, shaft #2 (most proximal shaft on the medical instrument 700), shaft #1 (middle shaft), and shaft #3 (most distal shaft on the medical instrument 700). As shown in FIG. 37, rotation of the pitch adjustment gear Spur-Z results in rotation of the gear Face-Y. Not shown in FIG. 37 is a stop on the gear Face-Y, and the amount of rotation of gear Face-Y results in an amount of index motion of the medical instrument 700.

Also shown in FIG. 37 are two outputs of the drive train assembly 2510. The A-B output (due to the trigger 180 moving from position A to position B) results in rotation of the drive belt 2530, thereby causing the stylet 2410 to move distally. The B-C output (due to the trigger 180 moving from position B to position C) results in rotation of the index lead screw 2540, thereby causing the medical instrument 700 to index a fixed amount.

Figure 38:
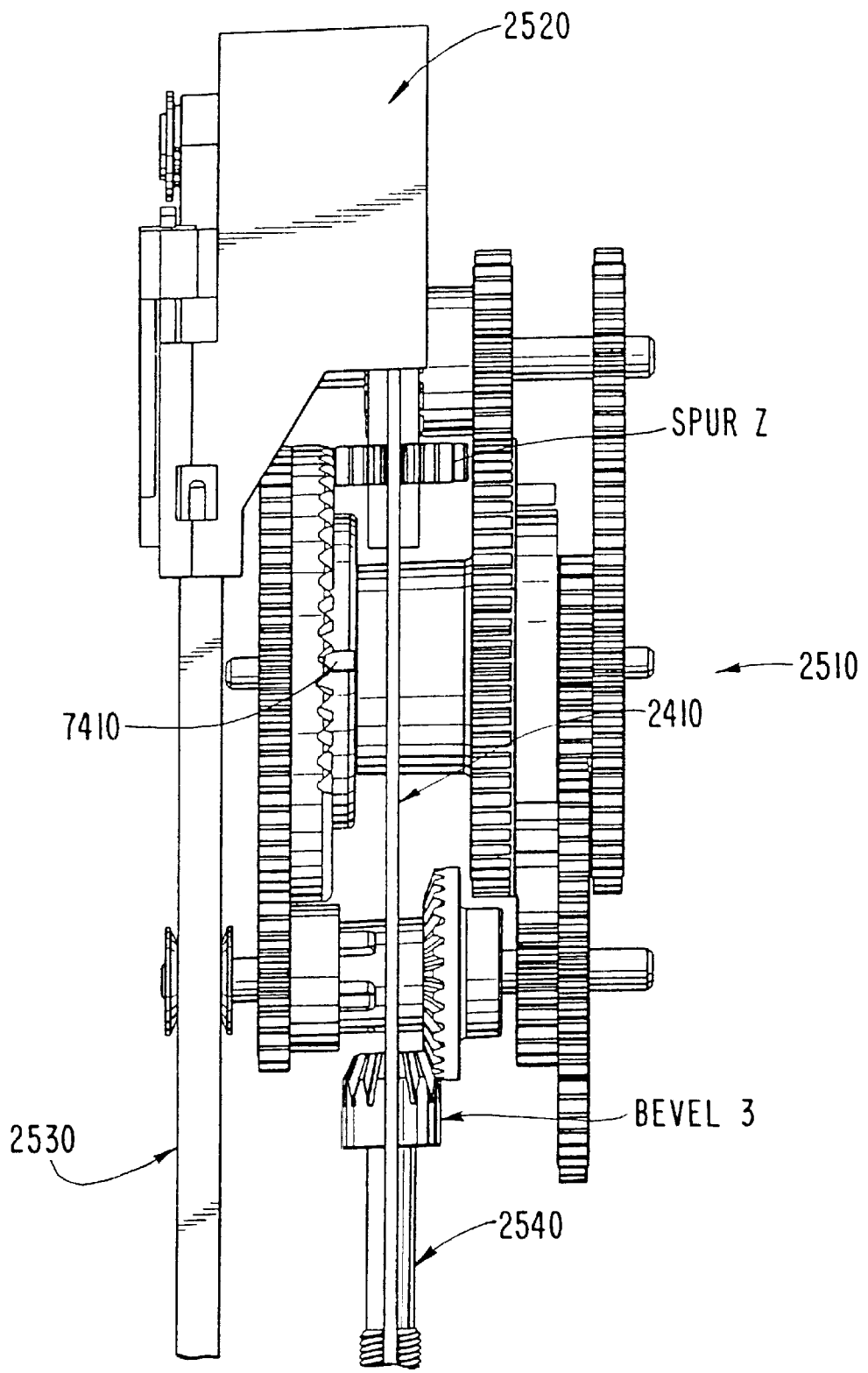
FIG. 38 is a bottom view of the drive train assembly, according to a preferred embodiment of the invention.

FIG. 38 is a bottom view of the drive train assembly 2510, whereby the pitch adjustment stop boss 7410 on the gear internal-1, comes into contact with a pitch adjustment stop boss on gear Face-Y. This feature will be explained in detail later on. Also, the flat bottom surface of the carriage portion 3310 of the stylet carriage assembly 2520 is also shown in FIG. 38.

Figure 39:
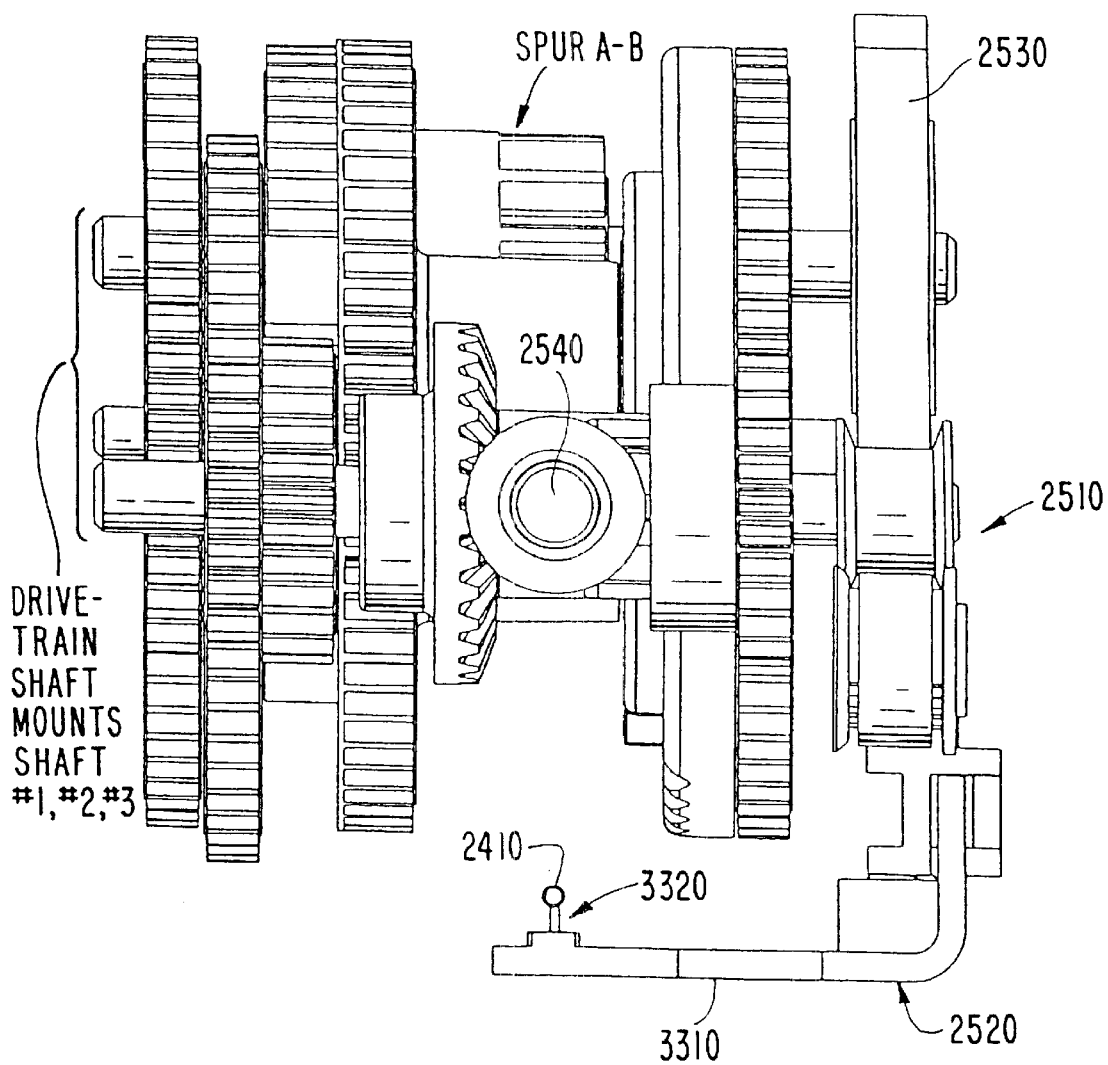
FIG. 39 is a front view of the drive train assembly, according to a preferred embodiment of the invention.

FIG. 39 is a front view of the drive train assembly 2510. FIG. 39 shows that the index lead screw 2540 is aligned with the center axis of the medical instrument, and that the stylet 2410 is also aligned directly below the index lead screw 2540. The alignment in this manner is preferable, but not mandatory. Also, the attachment of the stylet 2410 to the carriage portion 3310, by way of the tab 3320, can be seen in FIG. 39. Note also that the index lead screw 2540 is aligned with shaft #3 of the drive train assembly 2510. The alignment in this manner is preferable, but not mandatory.

Figure 40:
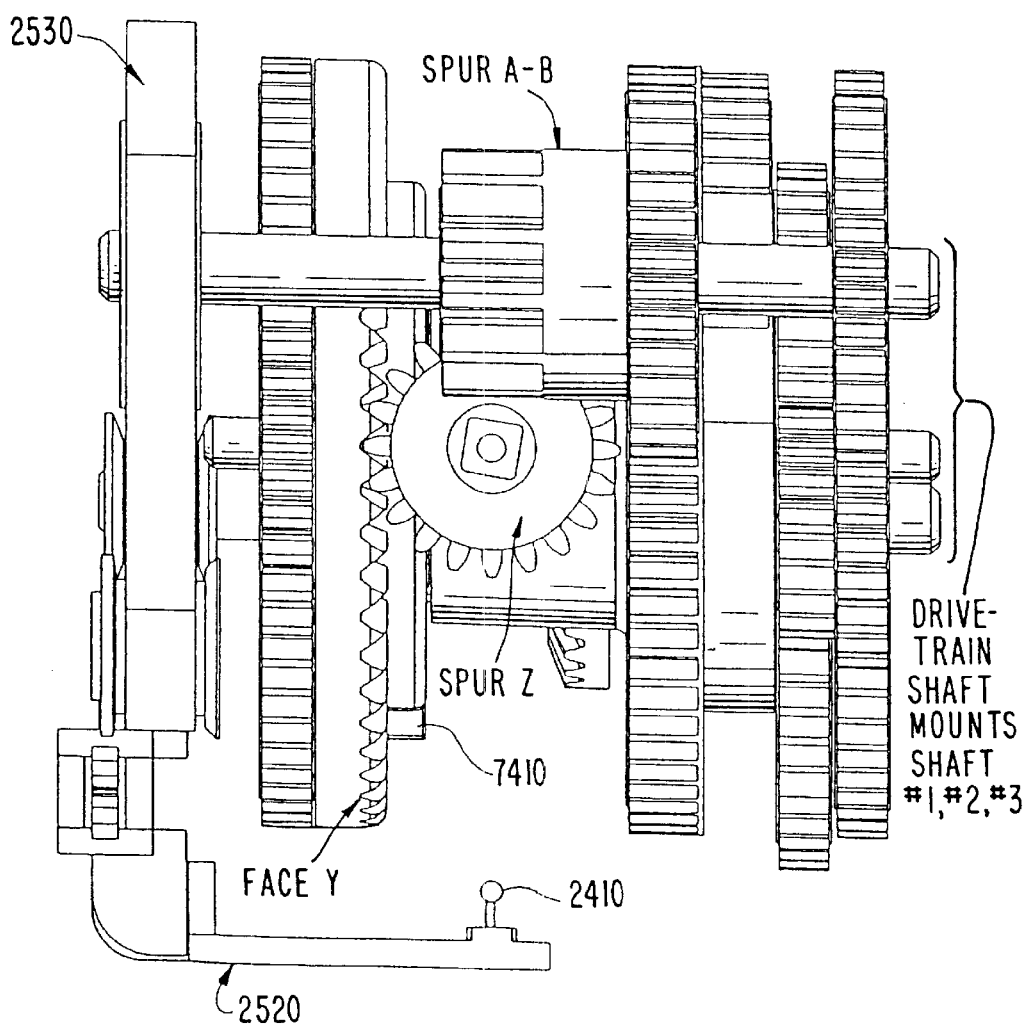
FIG. 40 is a back view of the drive train assembly, according to a preferred embodiment of the invention.

FIG. 40 is a back view of the drive train assembly 2510 within the medical instrument 700. The pitch adjustment gear Spur-Z can be seen, which is coupled to the pitch adjustment knob (not shown in this figure, but see element 170 in FIG. 1) at the proximal end of the medical instrument 700). The engagement of the pitch adjustment gear Spur-Z with the pitch adjustment stop gear Face-Y can be seen in FIG. 40.

Figure 41:
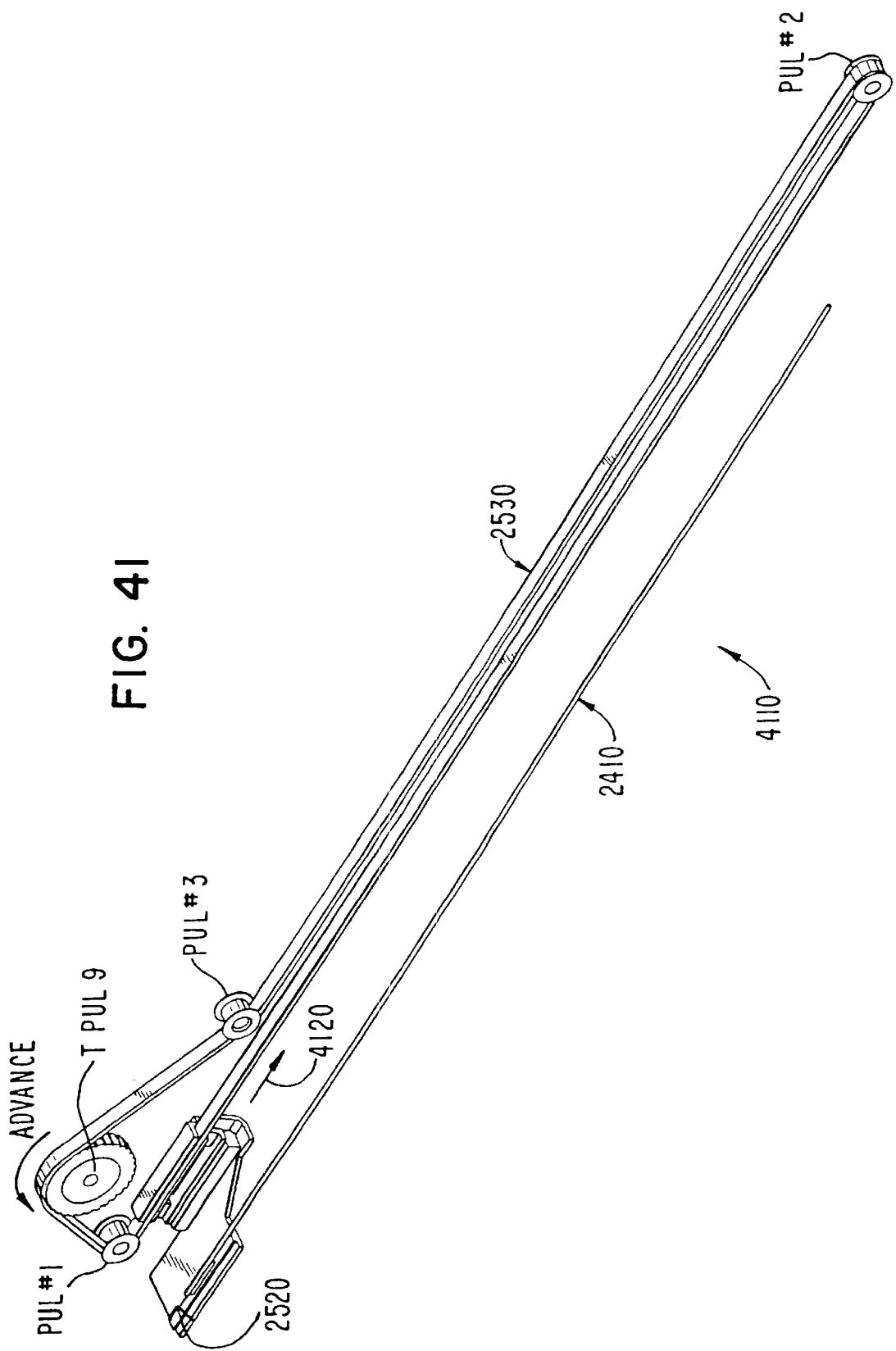
FIG. 41 is a top perspective view of the stylet carriage drive mechanism, according to the preferred embodiment of the invention.

Turning now to FIG. 41, this figure shows an isolation of the drive carriage assembly 2510 and the drive belt 2530, together operating as a stylet carriage drive mechanism 4110. This mechanism provides the basis for moving the stylet 2410 from a proximal, rest position, to a distal, extended position (see direction of arrow 4120 in FIG. 41). Movement of the stylet carriage assembly 2520 from the proximal position to the distal position results in pushing of a seed disposed in an extended shuttle 2430 (of a seed cartridge 110) to a distal end of a needle cannula 770. With the seed pushed to the distal end of the needle cannula 770, the seed can readily be deposited at a precise location within a patient's body, by having the medical instrument 700 index back away from the patient (due to trigger movement from position B to position C), and where the seed remains within tissue of the patient's body as the needle cannula 770 spins as it indexes.

While the medical instrument 700 according to the present invention supports needle spin as it indexes, due to trigger 180 movement from position B to position C, in an alternative embodiment the medical instrument 700 would only index with no needle spin occurring. Depending upon the location in a patient's body in which seeds are to be implanted, needle spin may or may not be warranted.

The spinning action also helps keep the seed in place within a desired location within a patient's body (i.e., a specific location within a patient's prostate gland). The three idler pulleys #1, #2, and #3, as well as the band drive timing pulley gear TPUL9, which provide tensioning of the drive belt 2530, and where gear TPUL9 also provides movement of the drive belt 2530 due to rotation of gear TPUL9, are shown in FIG. 41.

Figure 42:
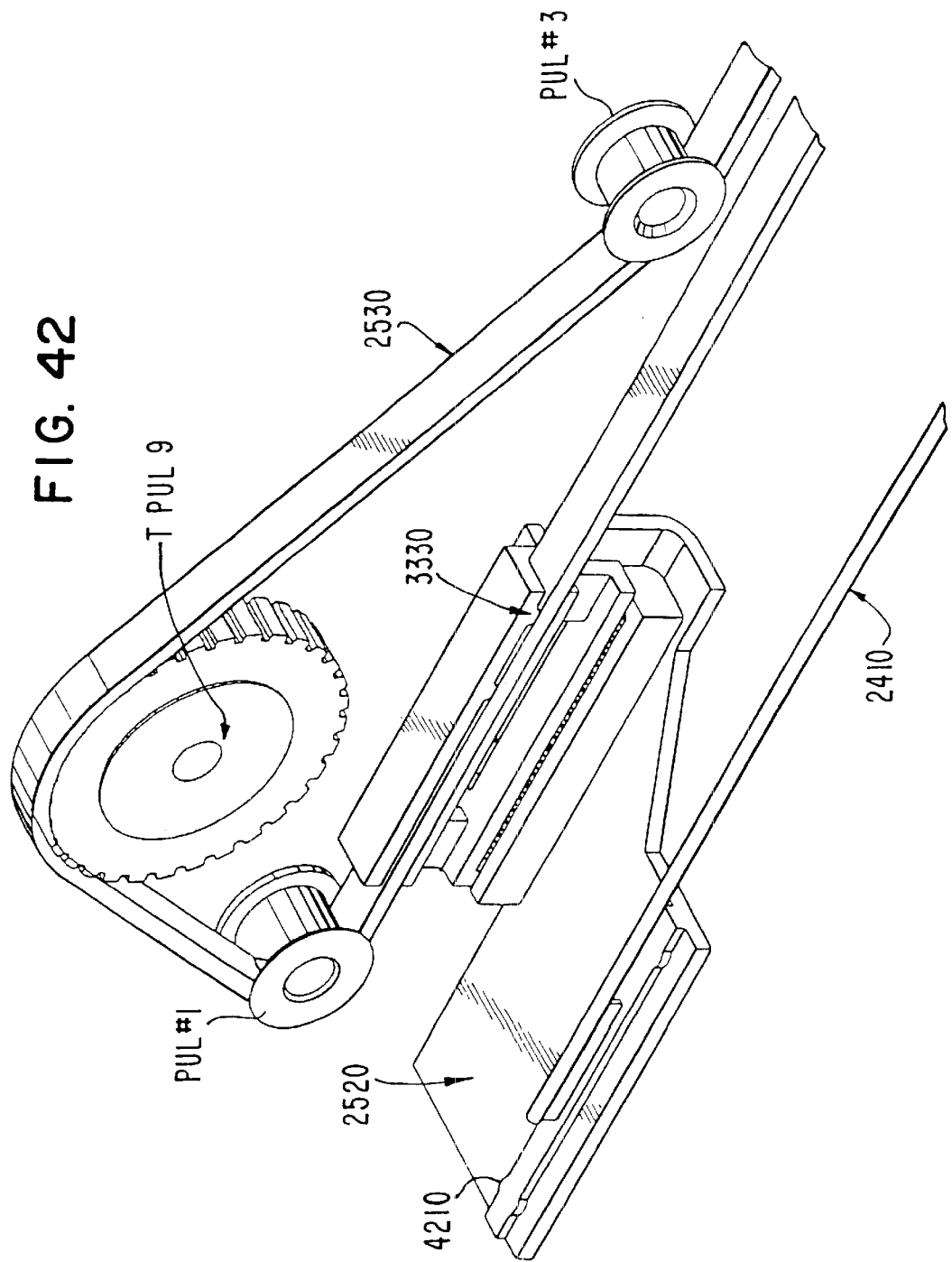
FIG. 42 is a blow-up of a portion of the view shown in FIG. 41.

Referring now to FIG. 42, which is a perspective view of the stylet carriage assembly 2520 as well as idler pulley PUL#1, idler pulley PUL#3, and gear TPUL9, the carriage portion 3310 has a guidance protrusion 4210 on a top surface thereof. The guidance protrusion 4210 is a feature that registers with a part of the inner frame (not shown) of the medical instrument 700, whereby the stylet carriage assembly 2520 is maintained in a precise path as it moves from its most proximal position to its most distal position, and back again.

Figure 43:
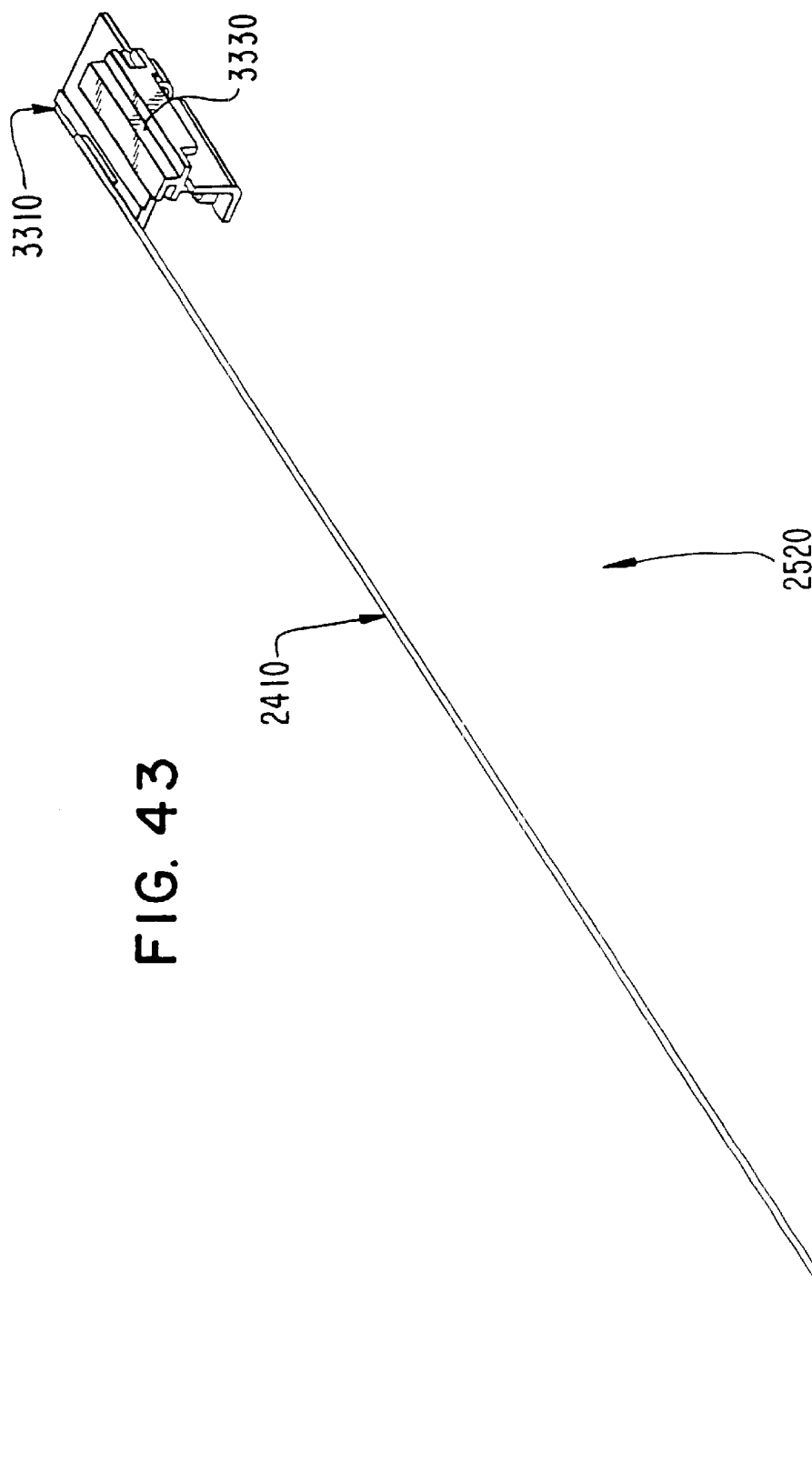
FIG. 43 shows the stylet carriage assembly, according to the preferred embodiment of the invention.
Figure 44:
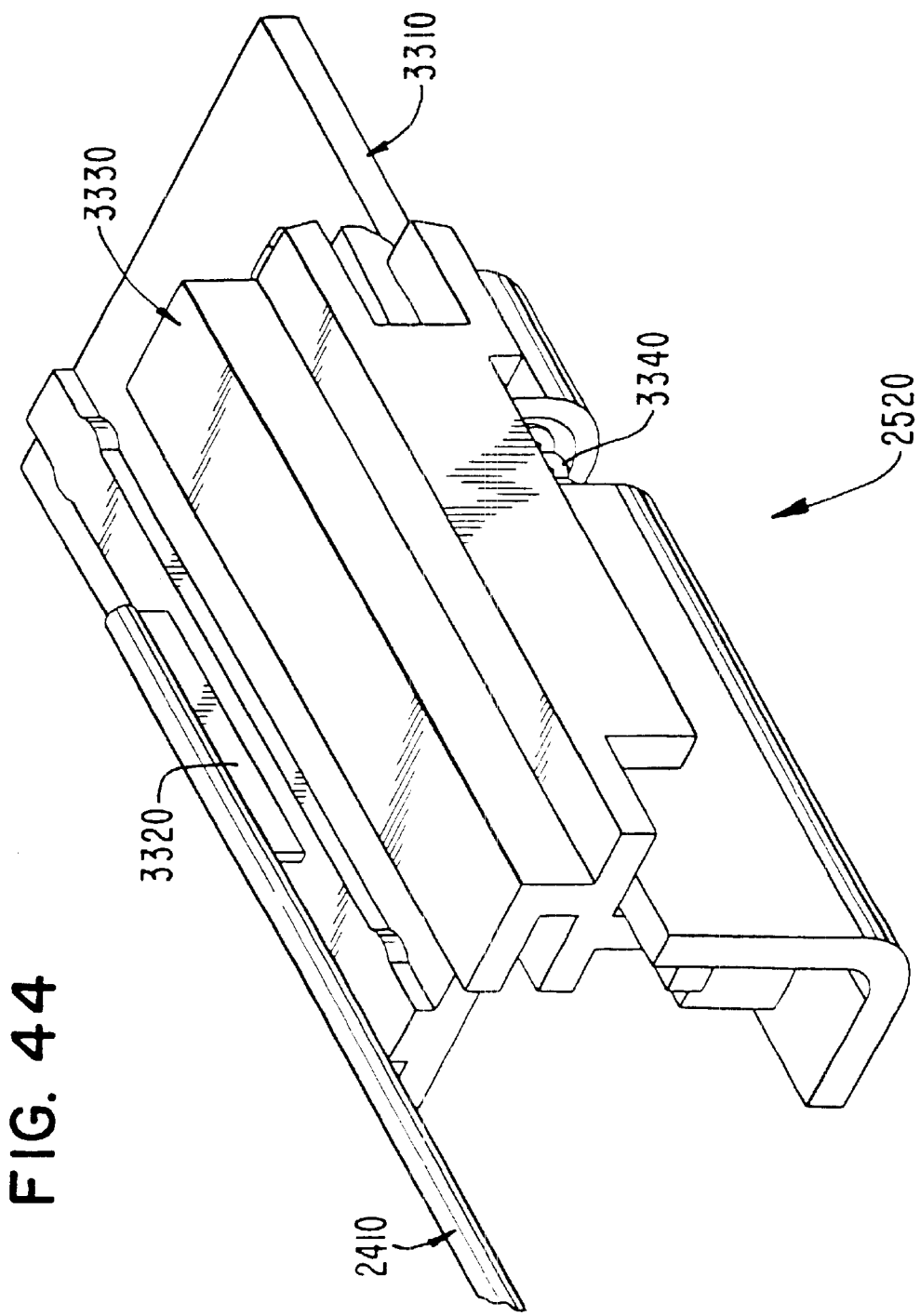
FIG. 44 shows a blow-up of the stylet carriage assembly, according to the preferred embodiment of the invention.

FIG. 43 shows the stylet 2410 coupled to the stylet carriage assembly 2520. Thought the stylet 2410 is shown as a solid wire in FIG. 43, it may alternatively be a hollow cannula, to provide venting to the seed as the seed is pushed to the distal end of the needle cannula 770 that is attached to the distal portion of the medical instrument 700. That is, with a hollow cannula used as the stylet 2410, when the seed is pushed to the distal end of the needle cannula 770, to a seed implant position, when the medical instrument 700 is indexed back away from the patient to allow the seed to be deposited in the patient's tissue, the stylet 2410 remains at its most distal position at the distal end of the needle cannula 770.

A hollow stylet allows for venting of air and the like (due to suction or pressure generated in the pushing of the seed to the distal end of the needle cannula 770) during this process, to thereby allow the seed to remain in place at the seed implant location. If a hollow stylet is used, then the front tip of the stylet 2410 should be sized so that the seed does not go into the hollow potion of the stylet 2410, but rather is pushed all the way by the front tip of the stylet 2410 to the distal end of the needle cannula 770 (see FIG. 79 showing the front tip of a stylet wire that is pushing a seed 2420 to the distal end of the needle cannula 770).

In more detail, as the seed is being pushed to the distal end of the needle cannula 770, a pressure wave within the needle cannula 770 is created, and without any venting of that pressure wave, this would result in some air being pushed into the patient's seed implant region. To stop this from happening, a hollow stylet may be utilized to provide the necessary venting of the pressure wave. Alternatively or in addition, the needle spin action between seed implant locations may be provided to lessen the pressure wave effect as well.

Figure 79:
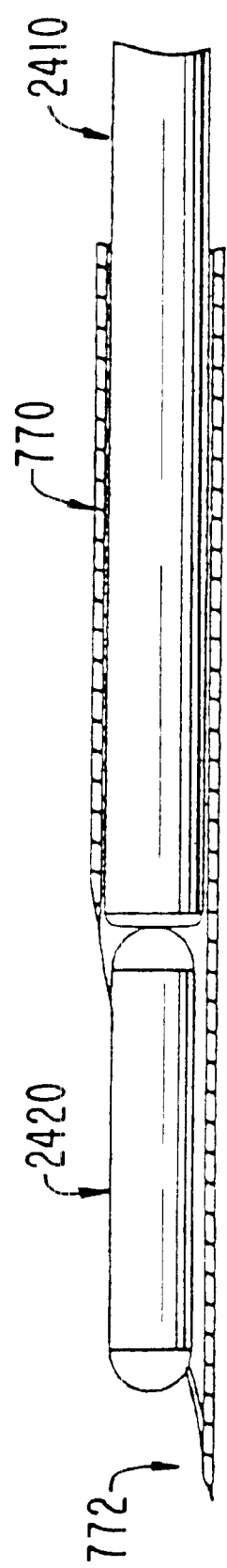
FIG. 79 shows the stylet 2410 having pushed a seed to a distal end of a bevel needle, due to movement of the trigger from position A to position B, according to the preferred embodiment of the invention.

FIG. 79 shows the stylet 2410 (shown as a non-hollow, solid wire in FIG. 79) disposed behind a seed 2420 that has been pushed to a distal end 772 of a needle cannula 770 (shown as a bevel needle in FIG. 79, but a trocar needle or other type of needle may be alternatively be used). The stylet 2410 is shown having a diameter slightly greater than the diameter of the seed 2420, but the stylet 2410 may alternatively have a diameter equal to or slightly less than the diameter of the seed 2420 that it is pushing.

Figure 48:
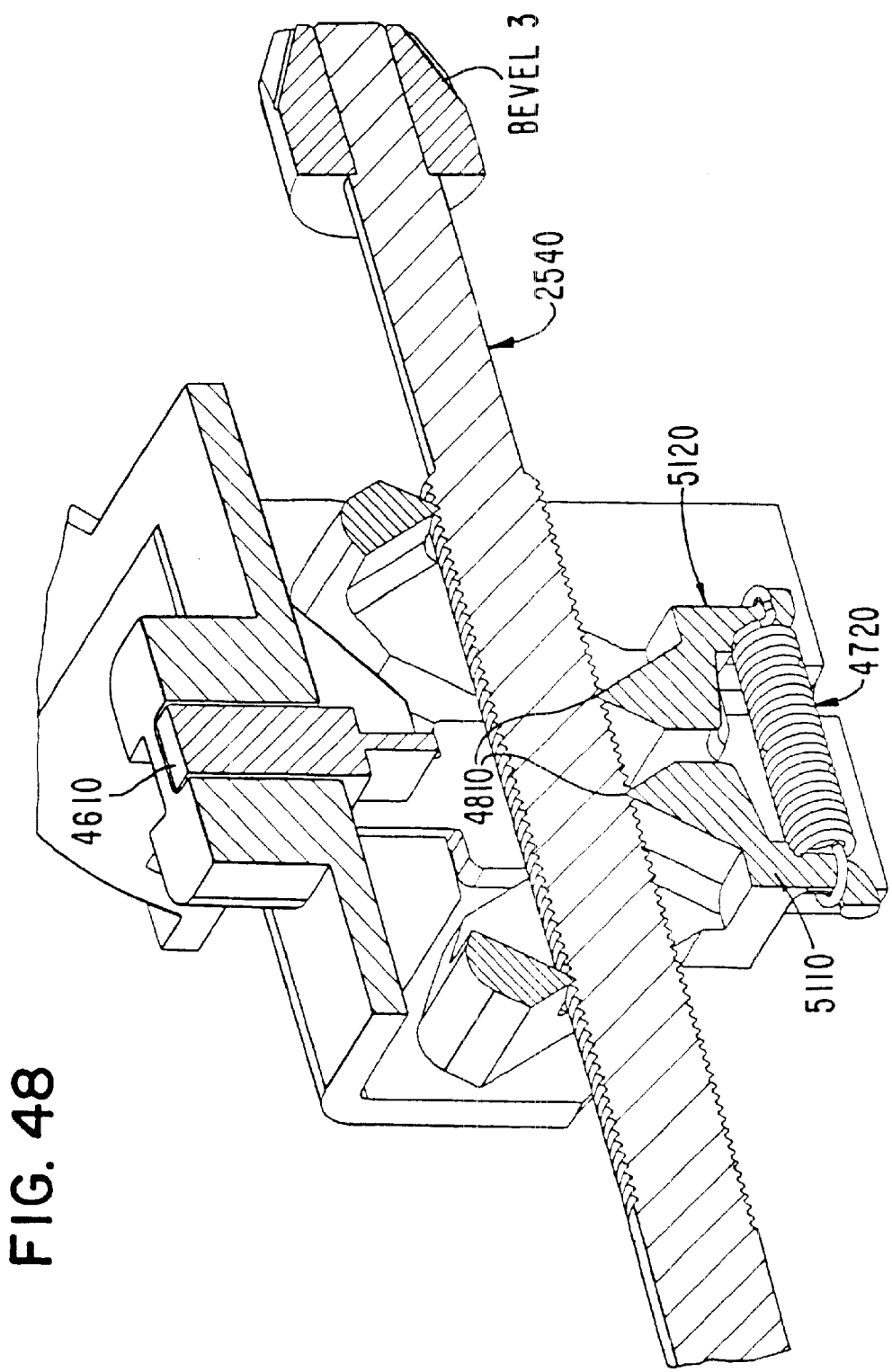
FIG. 48 shows an ISO section view of the indexing mechanism in the lock position, according to the preferred embodiment of the invention.

Turning now to FIG. 47 as well as several other figures, details of the nut box assembly 2550 will be described in detail. The nut box assembly 2550 clamps onto the index lead screw 2540 in an engaged position, as shown in FIG. 48, and can also be separated from the index lead screw 2540 in an unengaged position, as shown in FIG. 47. The depressing of a nut cam 4610 causes the nut box assembly 2550 to be disengaged from the index lead screw 2540, whereby the nut box assembly 2550 is engaged with the index lead screw 2540 in its normal state.

Due to rotation of the index lead screw 2540, which rotation occurs as a result of movement of the trigger 180 from position B to position C, the nut box assembly 2550 moves relative to the index lead screw 2540, since it travels along the multi-start threads of the index lead screw 2540. This movement of the nut box assembly 2550 results in indexing of the medical instrument 700, since the nut box assembly 2550 is affixed to a sheath unit 780 of a targeting fixture 720 (see FIG. 10). The nut box assembly 2550 moves along the slot 127 on the top surface of the medical instrument 700 (see FIG. 1) to a more distal position, thereby resulting in the medical instrument 700 moving back from the patient. This indexing or movement provides the movement necessary to move a needle cannula 770 (attached to the medical instrument 700) from a deeper seed implant location within the patient's body, to a next seed implant location that is less deeper within the patient's body.

FIG. 47 shows the index lead screw 2540 as a cross section, to clearly show the threads on the index lead screw 2540. Referring now to FIGS. 47, 48, 49 and 50, a cam surface 5010 at the bottom of the nut cam 4610 rests against the left and right nuts of the nut box assembly 2550, but does not apply any pressure to them, in the engaged position of the nut box assembly 2550. The left and right nuts 5110, 5120 are urged together by way of the nut extension spring 4720, which supplies sufficient tension on the left and right nuts 5110, 5120 to maintain the thread engagement blades of the left and right nuts 5110, 5120 onto respective threads of the index lead screw 2540.

When the nut cam 4610 is pushed downwards (due to operator actuation of a button 793 on a sheath unit 780 of a targeting fixture 720 on which the medical instrument 700 is coupled to), the cam surface 5010 of the nut cam 4610 pushes against the left and right nuts 5110, 5120 (see FIG. 50 in particular), causing them to rotate, thereby overcoming the tension force of the nut extension spring 4720. This results in the thread engagement blades separating from the threads of the index lead screw 2540, to a position as shown in FIG. 47. FIG. 48 shows the thread engagement blades 4810 of the nuts 5110, 5120 engaging the threads of the index lead screw 2540, which occurs when the nut cam 4610 is not pushed downwards. FIG. 49 shows a side view of the nuts 5110, 5120 engaged with the index lead screw 2540.

In the preferred embodiment, the thread engagement blades 4810 are plastic formed by injection molding, and alternatively they may be metal parts. The provision of a multi-start thread instead of blades may be incorporated into the nuts 5110, 5120 to distribute the force of the engagement of the nut box assembly 2550 to the index lead screw 2540. This lessens the possibility of wear and stripping of the thread engagement blades and the threads of the index lead screw 2540 due to many index movements of the medical instrument 700.

FIG. 51 shows the nut cam 4610 without the outer housing of the nut box assembly 2550, to provide a more clear drawing showing how it functions to push the left and right nuts 5110, 5120 off the index lead screw 2540, when the nut cam 4610 is pushed downwards.

Figure 52:
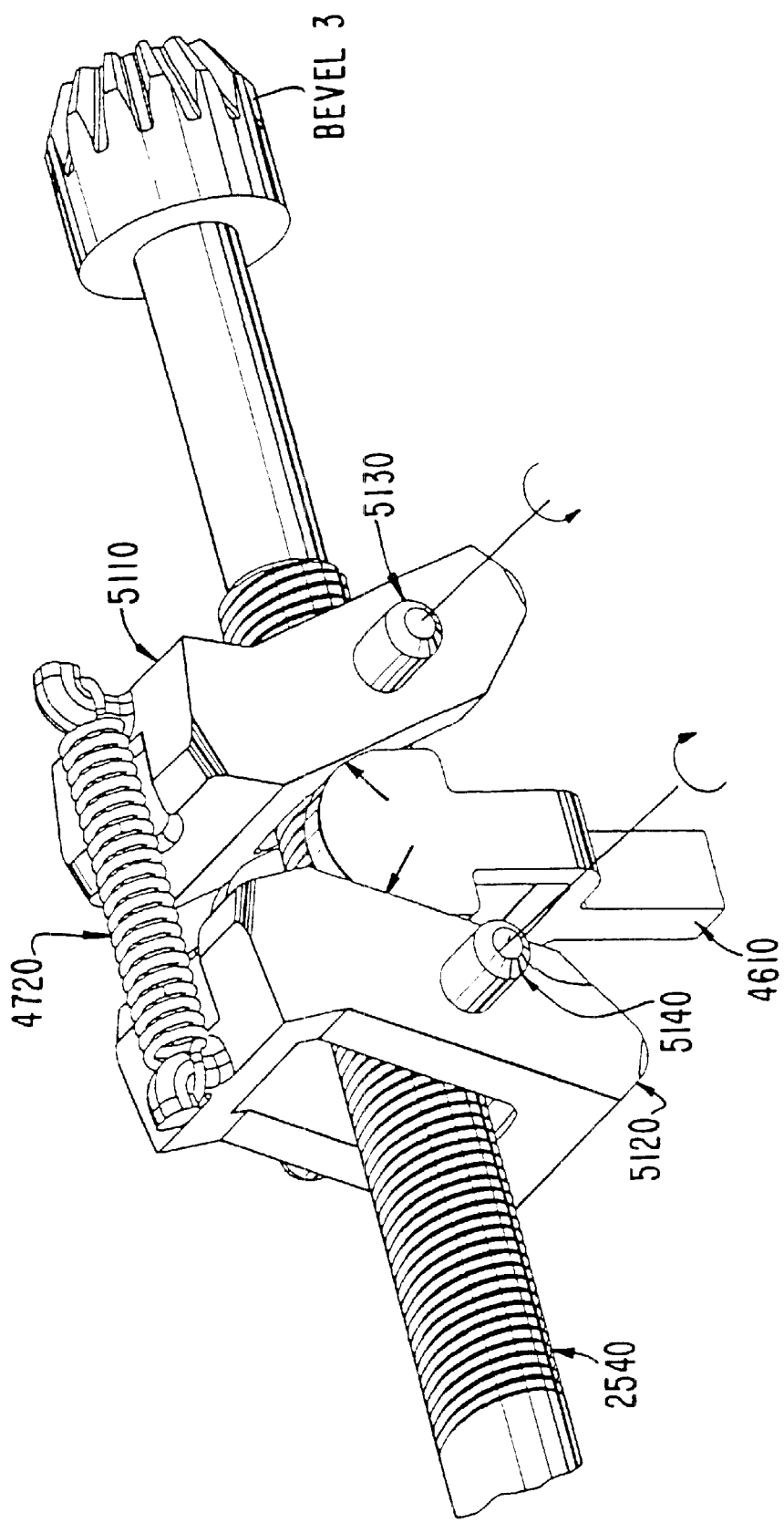
FIG. 52 is a bottom perspective view of components of the nut box assembly that are coupled to the index lead screw, with the outer housing of the nut box assembly removed for clarity, according to the preferred embodiment of the invention.

FIG. 52 is similar to FIG. 51, but shows a bottom view of the left and right nuts 5110, 5120, the index lead screw 2540, and the nut cam 4610. Note the pivot centers 5130, 5140 of the left and right nuts 5110, 5120, by which they rotate when pushed by the cam surface 5010 of the nut cam 4610, are shown in FIGS. 51 and 52.

Now, description will be made of the drive train assembly 2510, and how it operates to cause movement of the stylet 2410, as well as indexing of the medical instrument 700 (by rotating the index lead screw 2540).

Figure 53:
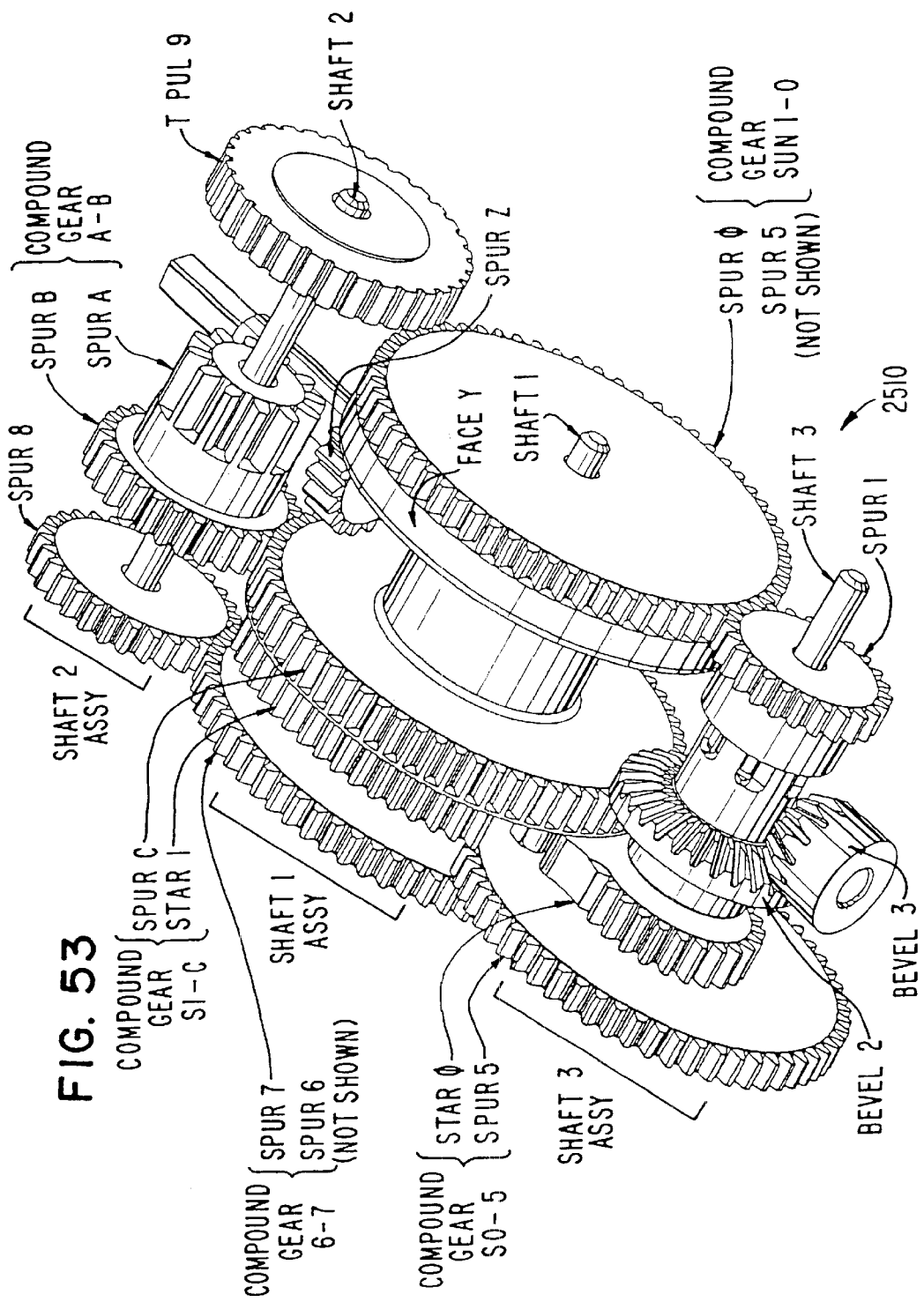
FIG. 53 is a top perspective view of the gears and shafts making up the drive train assembly, according to the preferred embodiment of the invention.

FIG. 53 shows a perspective view of the drive train assembly 2510, which includes compound gear S1-C (gear Spur-C and gear Star-1 as an integral component), compound gear 6-7 (gear Spur-7 and gear Spur-6 as an integral component), compound gear A-B (gear Spur-A and gear Spur-B as an integral component), gear Spur-8, gear TPUL-9, compound gear Sun1-0 (gear Spur-0 and gear Spur-S as an integral component), pitch adjustment gear Spur-Z, compound gear S0-5 (gear Star-0 and gear Spur-5 as an integral component), gear bevel-2, gear bevel-3 (coupled to the index lead screw 2540, not shown), gear Spur-1, gear Face-Y, and shafts#1, #2, and #3.

Except for gear Spur-8 and gear TPUL-9, all of the other gears rotate around the respective shafts#1, #2 and #3, and are not indexed to the shafts. Gear Spur-8 and gear TPUL-9 are registered or keyed to shaft #2, whereby rotation of gear Spur-8 results in rotation of shaft #2, which causes rotation of gear TPUL-9.

When the drive rack 2570 moves linearly as a result of the trigger 180 moving from position A to position B, this causes rotation of gear Spur A-B, since gear Spur-B is directly engaged with the drive rack 2570. Gear Spur-B is engaged with gear Spur-C of compound gear S1-C. Thus, gear Spur-C rotates as a result of the trigger 180 moving from position A to position B. Since gear Star-1 is integral with gear Spur-C, it also rotates.

Gear Star-1 is engaged with gear Star-0 of compound gear S0-5, in a modified geneva wheel arrangement, to be described in detail below. This engagement has a dwell period and a rotation period, whereby gear Star-0 dwells during some times when gear Star-1 rotates, and rotates at other times when gear Star-1 rotates. This rotating/dwelling is provided to cause the stylet 2410 to move to the most-distal position due to movement of the trigger 180 from position A to position B, and to stay at the most distal position during movement of the trigger 180 from position B to position C. The dwell aspect of the gear coupling is provided to maintain the stylet 2410 at its most distal position when the trigger 180 moves from position B to position C.

When gear Star-0 rotates, gear Spur-5 also rotates since they form a compound gear. Gear Star-5 is engaged with gear Spur-6 of compound gear 6-7, causing gear Spur-6 to rotate when gear Star-5 rotates. Since gear Spur-7 is integral with gear Spur-6 (they form a compound gear), gear Spur-7 also rotates. Gear Spur-7 is engaged with gear Spur-8, thereby causing gear Spur-8 to rotate when gear Spur-7 rotates. Rotation of gear Spur-8 causes rotation of shaft#2, since gear Spur-8 is keyed, or registered, with shaft#2. The rotation of shaft #2 causes rotation of gear TPUL9 which is also keyed, or registered, to shaft#2. Rotation of gear TPUL9 causes the drive belt 2530 to rotate, as seen in FIG. 35, for example, which in turn causes the stylet carriage assembly 2520 to move distally, since it is coupled to the drive belt 2530.

The engagement of gear Star-0 and gear Star-1 will be described in detail. Referring now to FIGS. 74A through 74-G, a modified geneva wheel mechanism, also referred herein as a star-wheel mechanism, provides precise movement of gears Star-0 and Star-1 as the trigger 180 moves from position A to position C is shown. As the trigger 180 is moved from position A to position B, the input gear Star-1 (see arrow in figures) moves 180 degrees counterclockwise, and the output gear Star-0 (see arrow in figures) moves 360 degrees clockwise. As the trigger 180 is moved from position B to position C, the input gear Star-1 moves 120 degrees (see arrow in figures), and the output gear Star-0 does not move (moves 0 degrees), thereby resulting in a dwell period (keeping the stylet 2410 at its most distal position).

Gear Star-1 is a star wheel (and is not a fully-segmented gear), and has two pins 7410A, 7410B protruding from the side face thereof. Gear Star-1 also has a cam surface 7420, and a teeth surface 7430. Gear Star-0 also has a cam surface 6130 and a teeth surface 6140 (see also FIGS. 61 and 62). When gear Star-0 engages the cam surface 7420 of gear Star-1, gear Star-0 dwells, and does not rotate. When gear Star-0 engages the pins 7410A, 7410B and the teeth portion 7420 of gear Star-1, gear Star-0 rotates.

FIG. 74A shows the engagement of gear Star-1 with gear Star-0 in the rest position, corresponding to trigger position A. In the rest position, gear Star-0 is coupled to the cam surface 7420 of gear Star-1, with the pin 7410A of gear Star-1 engaged within a pin slot of gear Star-0.

FIG. 74B shows the initial movement of these two gears as the trigger 180 is started to move from position A to position B. Gear Star-0 rotates as the pin 7410A of gear Star-1 moves within the slot of gear Star-0, causing some rotation of gear Star-1. Pin 7410A causes the rotation of gear Star-0 at this time.

FIG. 74C shows the next movement of these two gears as the trigger 180 is moved more from position A to position B. The teeth of gear Star-0 start to engage the teeth on the teeth portion 7420 of gear Star-1, thereby causing gear Star-0 to rotate.

Rotation of gear Star-0 results in rotation of gear TPUL9, as described above, which causes the stylet 2410 to move to its most-distal position within the medical instrument 700. FIG. 74D shows gear Star-0 at the end of the teeth portion 7420 of gear Star-1, whereby it is starting to engage with the other pin 7410B on the face of gear Star-1, which is starting to enter the other slot of gear Star-0. In FIG. 74D, the gear segments of gears Star-0 and Star-1 start to disengage from each other.

FIG. 74E shows the other pin 7410B on the face of gear Star-1 further entering the other slot of gear Star-0, which occurs as the trigger 180 is moved to position B from position A. Pin 7410A controls rotation of gear Star-0 in the position shown in FIG. 74E.

FIG. 74F shows the gear Star-0 initially engaged with the cam surface 7420 on the face of gear Star-1, which occurs when the trigger 180 reaches position B. As long as gear Star-0 is engaged with the cam surface 7420 on the face of gear Star-1, gear Star-0 will not rotate, thereby causing it to dwell. This also causes the stylet 2410 to dwell at its most distal position.

FIG. 74G shows the coupling of the gears Star-0 and Star-1 as the trigger 180 is moved from position B to position C. During this trigger movement, the stylet 2410 remains at its most distal position, since gear Star-0 is dwelling at this time, and thus the drive belt 2530 (that is coupled to the stylet 2410 by way of the stylet carriage assembly 2520) is not moving at all.

As the trigger 180 is moved back from position C to position A, the gears Star-1 and Star-0 move in the opposite direction, starting at the engagement as shown in FIG. 74G and ending at the engagement as shown in FIG. 74A. This effectively moves the stylet 2410 back to the most-proximal position within the medical instrument 700.

As described above, the coupling of gear Star-1 to gear Star-0 is via a modified geneva wheel coupling, which allows a constant input motion (rotation) of gear Star-1 and allows gear Star-0 to initially move and then dwell during the constant input motion of gear Star-1. This moves the stylet 2410 forward (to its most distal position), and keep it in place while still having a constant trigger input and allowing an index motion of the medical instrument 700 (due to trigger movement from position B to position C).

Figure 54:
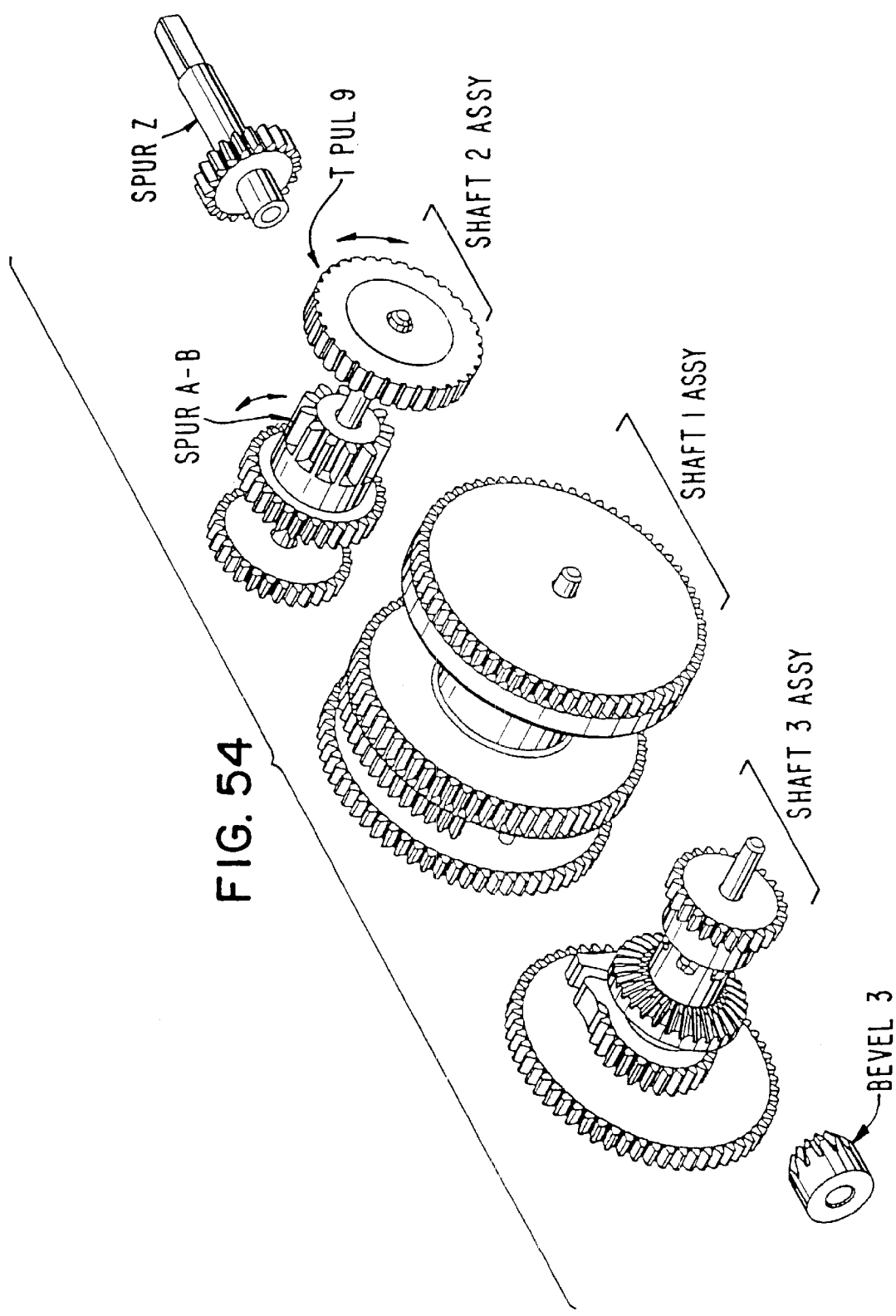
FIG. 54 is an exploded view of the gears and shafts making up the drive train assembly, according to the preferred embodiment of the invention.

FIG. 54 shows the three shaft assemblies of the drive train assembly 2510, whereby each shaft assembly is shown isolated from the other shaft assemblies. Also shown in FIG. 54 is gear Bevel-3, which is coupled to the index lead screw 2540.

One input to the drive train assembly 2510 is via gear Spur-Z, which provides the pitch amount that results in the medical instrument 700 indexing an operator-desired amount when the trigger 180 is moved from position B to position C.

Another input to the drive train assembly 2510 is the movement of compound gear Spur A-B, which is caused to rotate due to linear movement of the drive rack 2570 that is engaged with that compound gear. The outputs of the drive train assembly 2510 are rotation of the drive belt 2530 due to rotation of gear TPUL9, and rotation of gear Bevel-3 (which is coupled to the index lead screw 2540).

Figure 55:
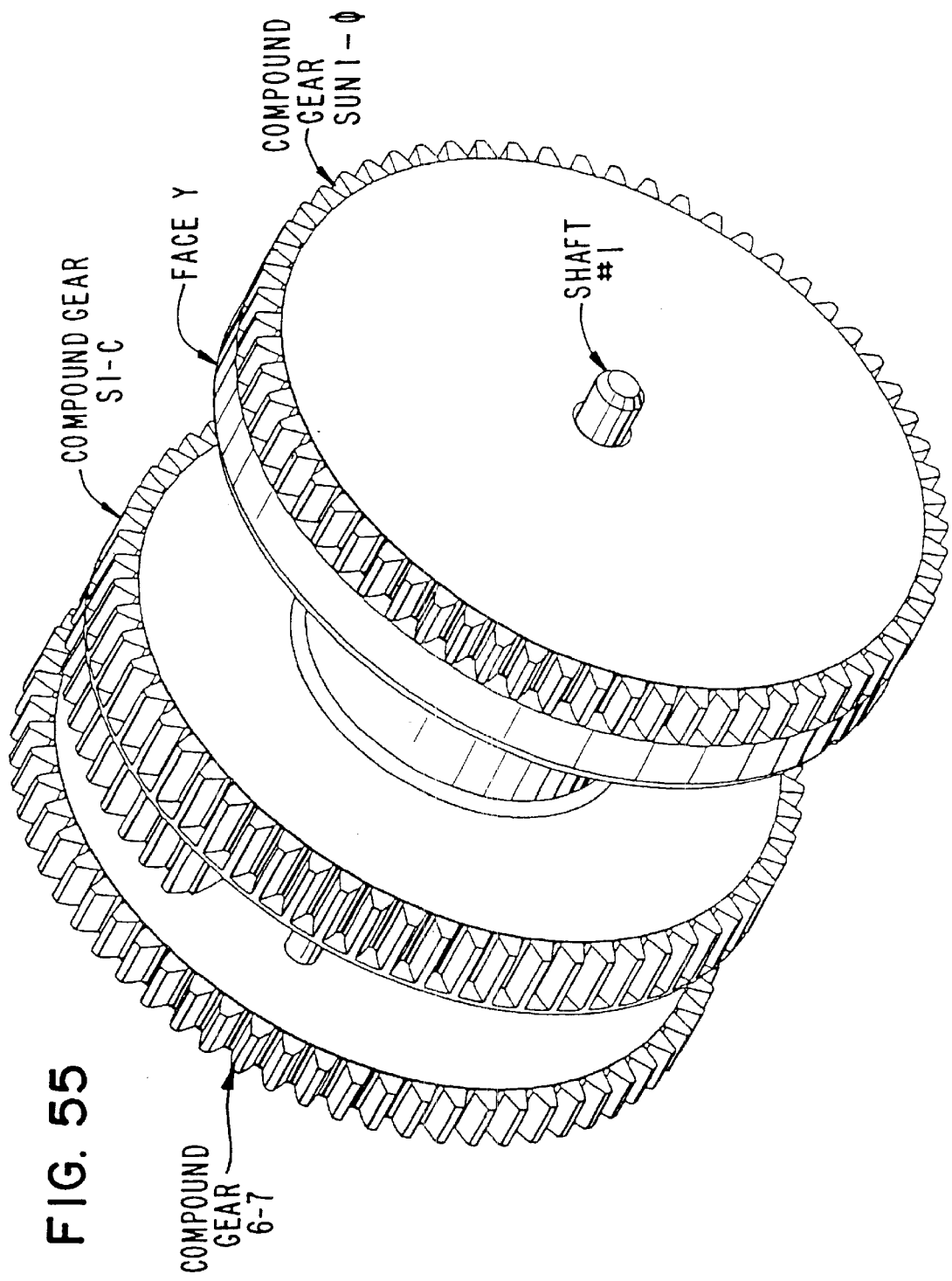
FIG. 55 is a view of the elements of the shaft#1 assembly of the drive train assembly, according to the preferred embodiment of the invention.

FIG. 55 shows the gears on shaft#1, as a complete shaft#1 assembly. The shaft#1 assembly includes compound gear 6-7, compound gear S1-C, gear Face-Y, and compound gear Sun1-0. All of these gears rotate around shaft#1, but none of these gears are registered to shaft#1 (that is, as these gears rotate, shaft#1 does not rotate with them).

Figure 56:
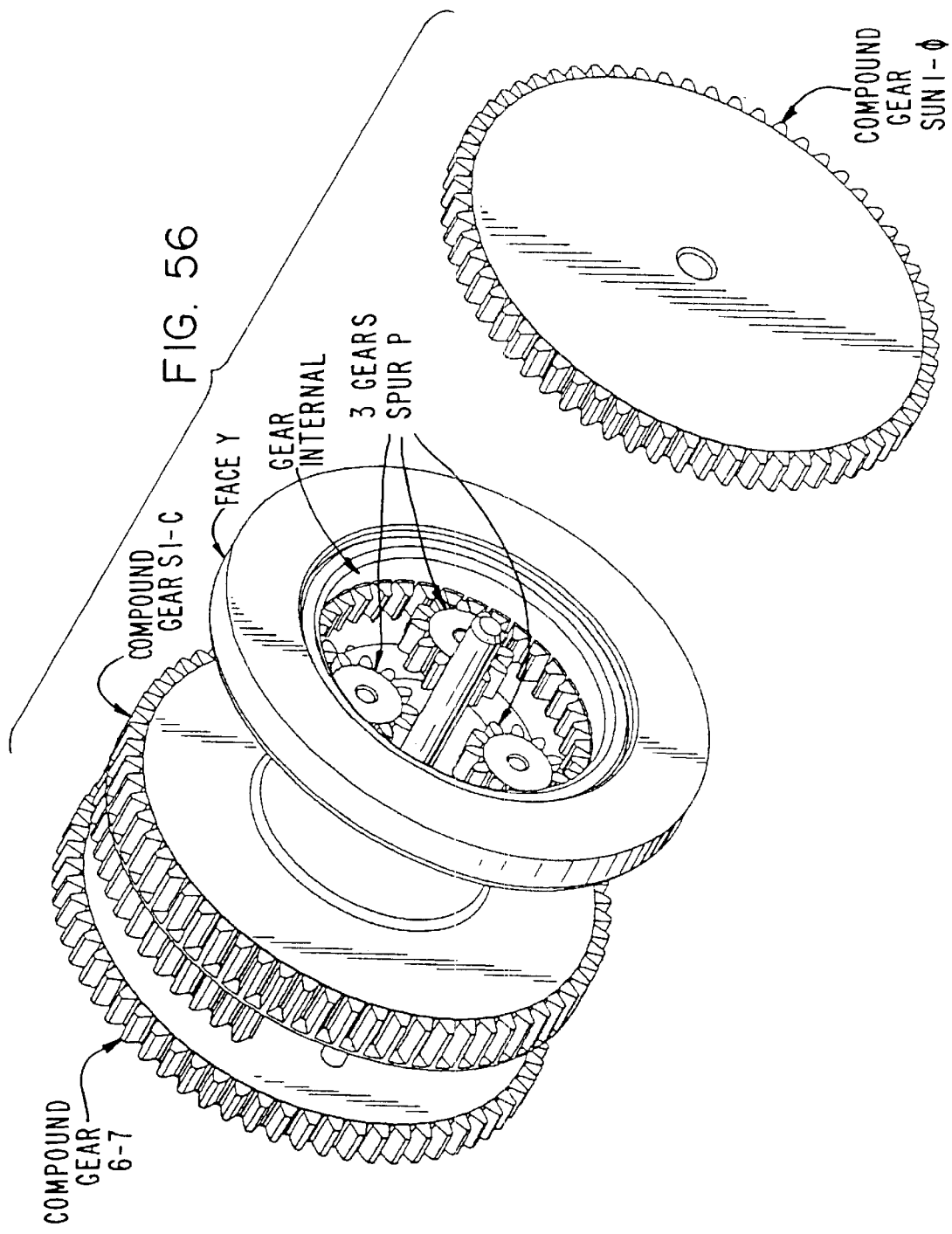
FIG. 56 is a partial exploded view of the shaft#1 assembly of the drive train assembly, according to the preferred embodiment of the invention.

FIG. 56 shows an exposed view of the shaft#1 assembly, the planetary gears Spur-P within the gear Face-Y are shown. These elements provide the mechanism for compound gear S1-C to drive compound gear Sun1-0.

Figure 57:
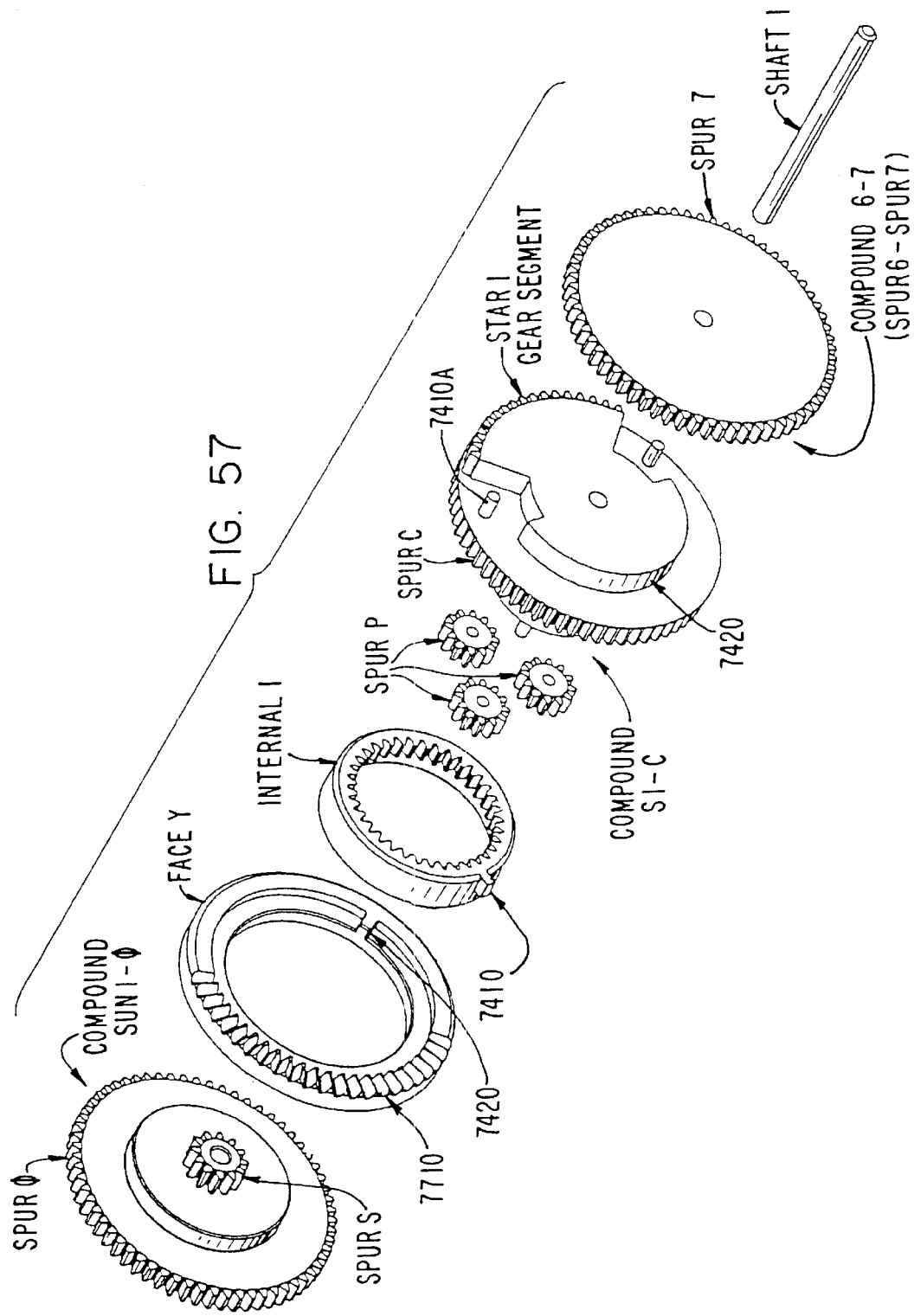
FIG. 57 is a fully exploded top perspective view of the shaft#1 assembly of the drive train assembly as viewed from one angle, according to the preferred embodiment of the invention.

Referring now to FIGS. 56 and 57 (showing a full exploded view of the elements making up the shaft#1 assembly), at the center of compound gear S1-C is a hub. The hub has three pins extending from it, as seen best on the view of compound gear S1-C in the exploded view of FIG. 58 (showing an opposite view as the one shown in FIG. 57). Those three pins extend from a front face of the compound gear S-1C, and are denoted as shaft#4 in FIG. 58. Gear Spur-6 cannot be seen in FIG. 57, but it can be seen in FIG. 58.

Three planetary gears Spur-P are respectively provided on the three shaft#4 pins, to hold them in place. The planetary gears Spur-P are free to rotate on the three pins, respectively. With this coupling, when compound gear S1-C rotates, the three pins rotate, and this rotation imparts motion to the three planetary gears Spur-P.

The three planetary gears Spur-P are each engaged with sun gear Spur-S, which is part of compound gear Sun1-0.

FIG. 57 shows gear Spur-S, which has twelve teeth in a preferred configuration. FIGS. 75, 76, 77 and 78 show the engagement of the three planetary gears Spur-P with the sun gear Spur-S.

The planetary gears Spur-P are controlled by two simultaneous inputs. One input is the motion of compound gear S1-C, and the other is the motion of gear internal-1. The output is motion of compound gear Sun1-0 which is the output of the shaft#1 assembly.

In more detail, gear internal-1 has a stop tab 7510 on its outer diameter. The stop tab 7510 of gear internal-1 rides along the inner diameter of gear Face-Y. That way, the outer diameter of gear internal-1 is registered on the inner diameter of gear Face-Y.

There also is a stop tab 7520 on gear Face-Y. Gear Face-Y also has an internal counter bore, which allows the gear internal-1 to rotate along the internal surface of gear Face-Y, and eventually as gear internal-1 rotates its stop tab 7510 comes into contact with the stop tab 7520 on gear Face-Y.

The stop tab 7520 on gear Face-Y limits the angular rotation of gear internal-1 to a rotational value determined by the angular position of gear Face-Y. The angular position of Gear Face-Y is set by the pitch control knob 170, and once set is fixed in position and cannot move.

Figure 58:
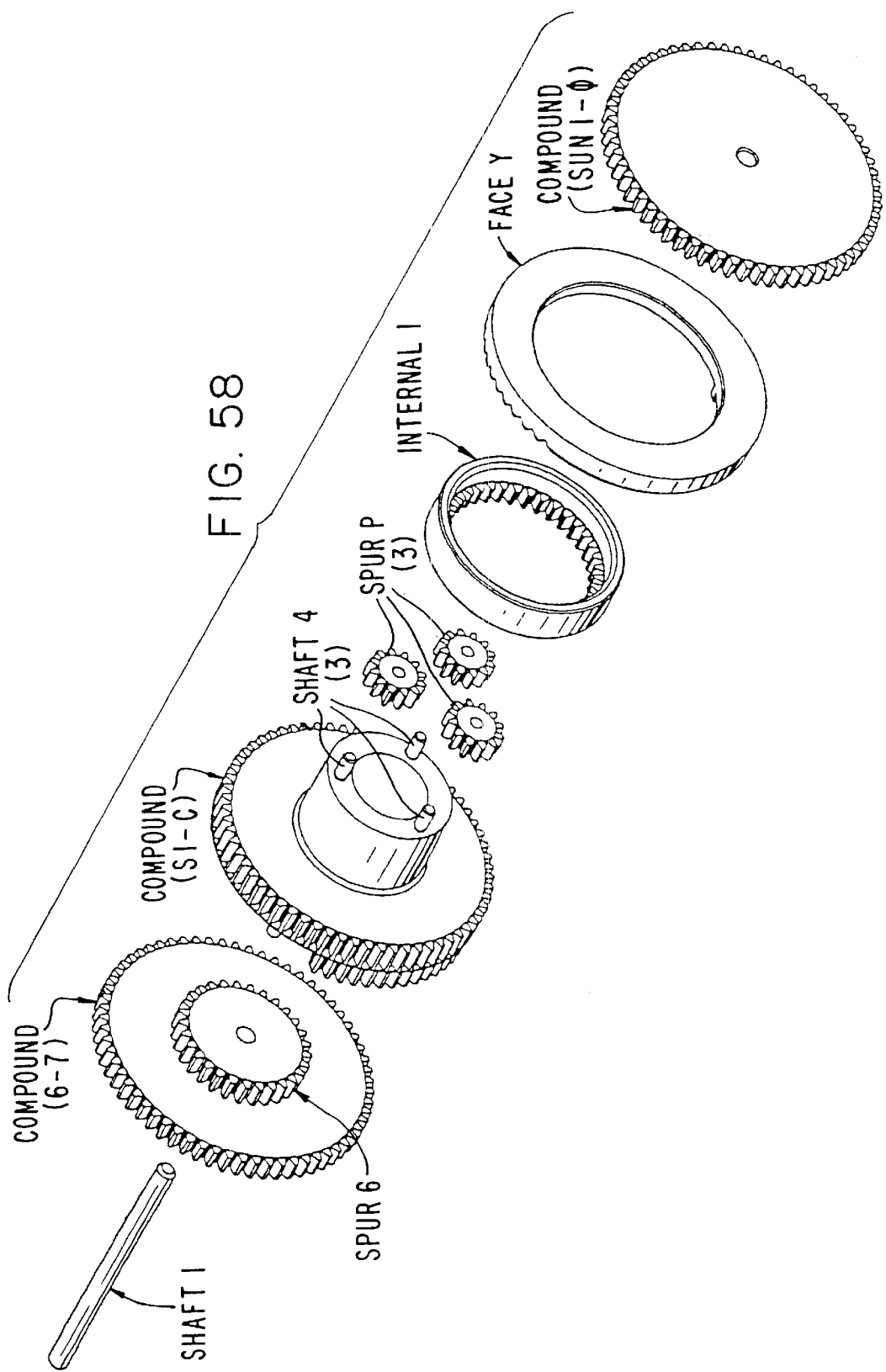
FIG. 58 is a fully exploded top perspective view of the shaft#1 assembly of the drive train assembly as viewed from another angle, according to the preferred embodiment of the invention.

FIG. 58 shows, in exploded view form how the three planetary gears Spur-P engage the three pins denoted as shaft#4, as viewed from an opposite side as the exploded view of FIG. 57.

The operation of gear internal-1 and gear Face-Y, with respect to causing index movement of the medical instrument 700, will now be explained below.

Figure 75:
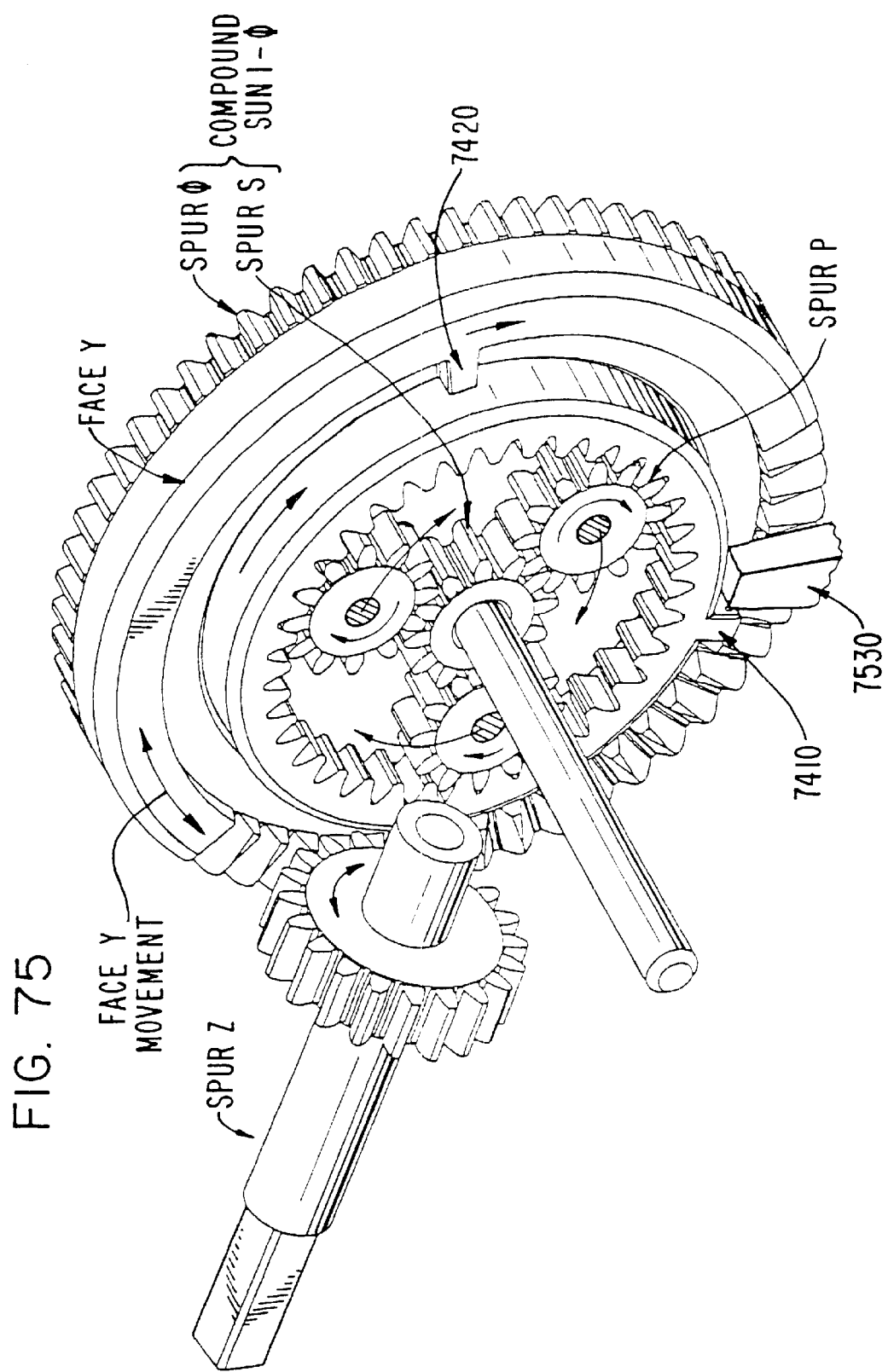
FIG. 75 shows a perspective view of an index-pitch adjustment mechanism, showing the motion of elements due to movement of the trigger from position A to position B, according to the preferred embodiment of the invention.

FIG. 75 shows the components of the drive train assembly 2510 that provide for indexing of the medical instrument 700 by an amount corresponding to a particular setting of the pitch adjustment knob 170. Gear Spur-Z is coupled to the pitch adjustment knob (not shown, but see element 170 in FIG. 1), and is rotates in accordance with the rotation of the pitch adjustment knob. The pitch adjustment knob is rotated by an operator to a desired pitch amount, to result in a desired amount of indexing of the medical instrument between seed implant locations.

In the process of rotating of gear Spur-Z, gear Face-Y rotates due to its engagement with gear Spur-Z. In FIG. 75, the stop 7510 of gear internal-1 is abutted against a frame stop 7530, with this corresponding to a home or rest position of gear internal-1.

Every time the medical instrument 700 is cycled (e.g., trigger 180 moved from position A to position B to position C, back to position B and then back to position A), the stop 7510 of gear internal-1 comes in contact with and strikes the frame stop 7530.

The arrows provided in FIG. 75 show the movements of the various gears when the trigger 180 is moved from position A to position B. As stated earlier, the three pins denoted as shaft#4, on which the three planetary gears Spur-P are disposed, move clockwise as seen in FIG. 75. The three planetary gears Spur-P rotate clockwise during this movement.

Sun gear Spur-S, which is provided at the center of the gear internal-1, is provided around shaft#1. Sun gear Spur-S has friction on it due to the resistance from downstream components such as the index lead screw 2540, which is indirectly coupled to shaft#1 (by various gears of the drive train assembly 2510). That is, even though gears Spur-P rotate and thus provide force on sun gear Spur-S, they do not overcome the friction that is maintaining sun gear Spur-S at a rest position, and thus sun gear Spur-S does not rotate at this time. The design of these gears so as to provide enough friction on sun gear Spur-S so that the rotation of the three planetary gears Spur-P does not cause it to rotate can readily be determined by one skilled in the art, and will not be discussed herein.

The rotation of planetary gears Spur-P impart motion onto gear internal-1, to which they are engaged by their respective gear teeth. This causes gear internal-1 to rotate clockwise, in a same direction as the rotation of planetary gears Spur-P. Note that the forces required to motivate sun gear Spur-S are higher than the forces required to motivate gear internal-1.

Gear internal-1 will continue to rotate (see dashed line in FIG. 76) until its stop 7510 hits the adjustable stop 7520 on gear Face-Y. All during this time, no motion is imparted onto sun gear Spur-S.

Figure 76:
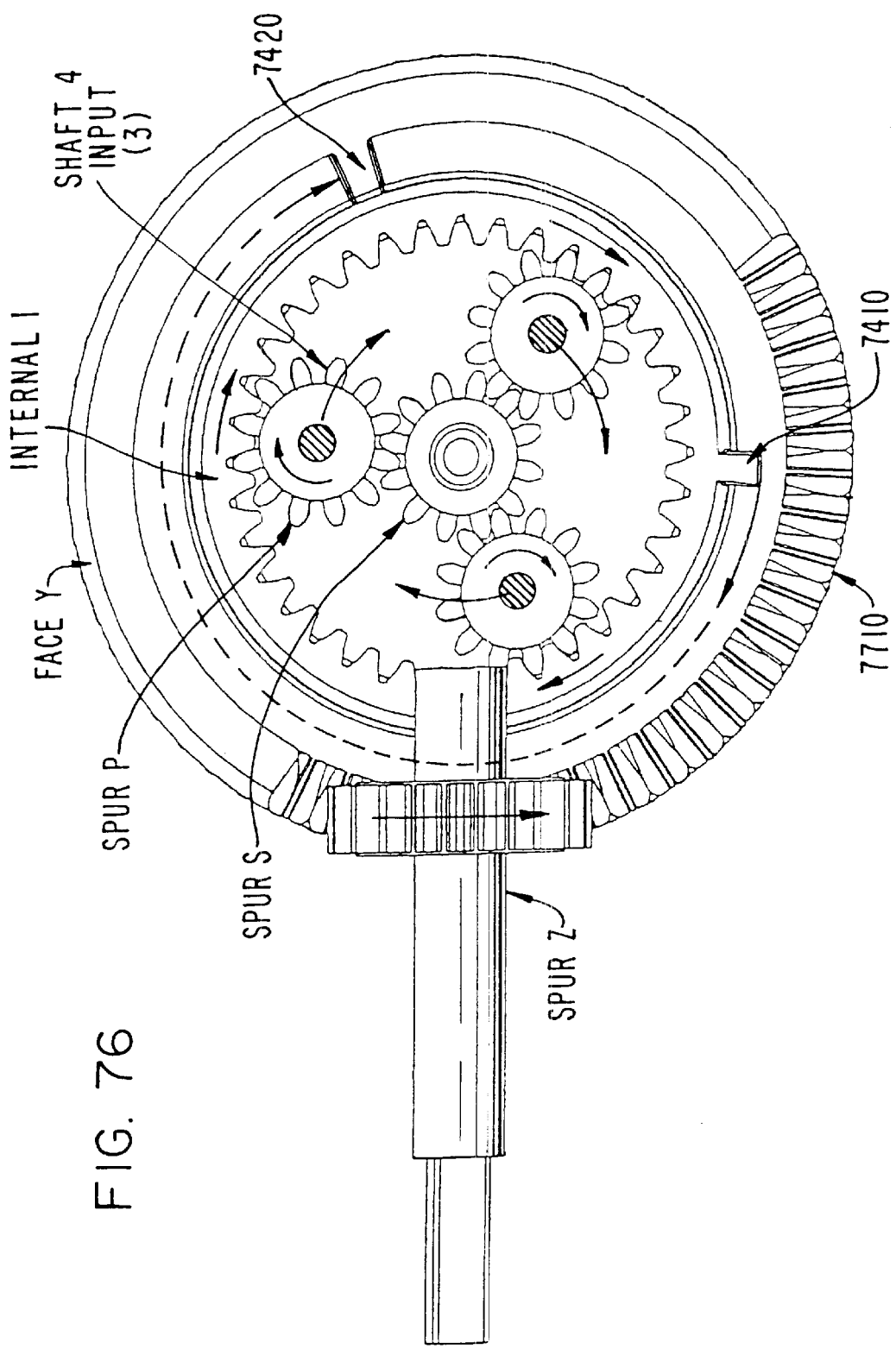
FIG. 76 shows a side view of an index-pitch adjustment mechanism, showing the motion of elements due to movement of the trigger from position A to position B, according to the preferred embodiment of the invention.

FIG. 76 shows a side view of the indexing elements shown in FIG. 75. In that figure, gear Spur-Z is held in a detent position between 0 degrees and 288 degrees, which is the initial input range for pitch setting of the medical instrument 700.

Figure 77:
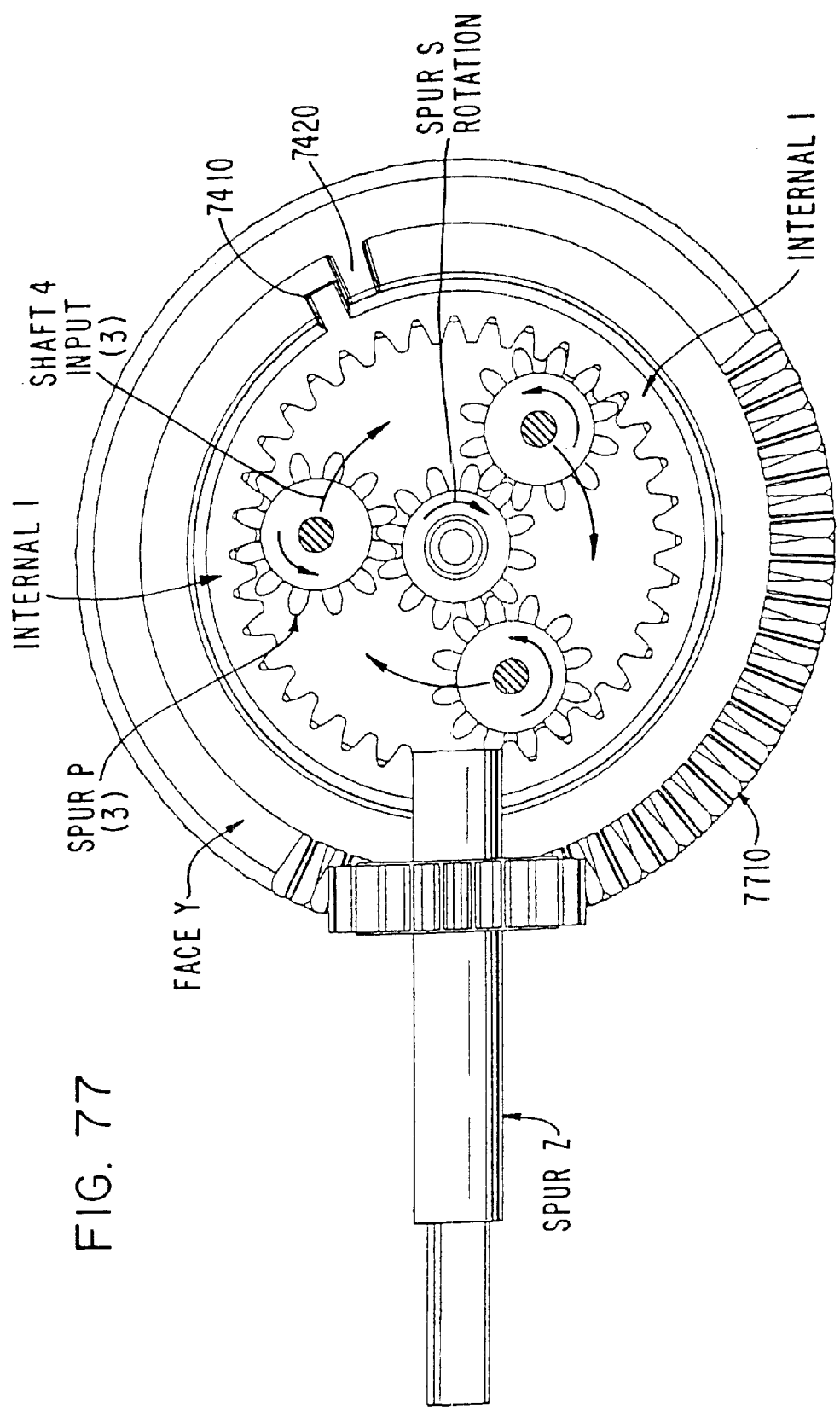
FIG. 77 shows a side view of an index-pitch adjustment mechanism, showing the motion of elements due to movement of the trigger from position B to position C and with the pitch amount at its maximum value, according to the preferred embodiment of the invention.

FIG. 77 shows the state at which the stop 7510 of gear internal-1 comes in contact with the stop 7520 on gear Face-Y. This point of contact corresponds to the trigger 180 being at position B. Now, as the trigger 180 is moved onwards from position B to position C, the contact of stop 7510 of gear internal-1 pushing against the stop 7520 of gear Face-Y prevents the gear internal-1 from rotating as gear Face-Y is fixed in its detent position. The rotation of shaft#4 in a clockwise fashion will cause the planetary gears Spur-P to rotate counterclockwise (this is a result of internal-1 stop 7410 being against Face-Y stop 7420).

The rotation of sun gear Spur-S results in rotation of gear Spur-0, since they combine to form compound gear Sun1-0. The rotation of gear Spur-0 causes rotation of gear Spur-1 on shaft#3, since their respective teeth are engaged. Rotation of gear Spur-1 results in rotation of gear Bevel-2, since they are coupled to each other. Rotation of gear Bevel-2 results in rotation of gear Bevel-3, which in turn results in rotation of the index lead screw 2540 coupled to gear Bevel-3. Refer to FIG. 53 for the coupling of these gears of the drive train assembly 2510, which results in indexing the medical instrument 700 due to the movement of the nut box assembly 2550 distally, as it rides along the threads of the index lead screw 2540 as it turns.

Figure 78:
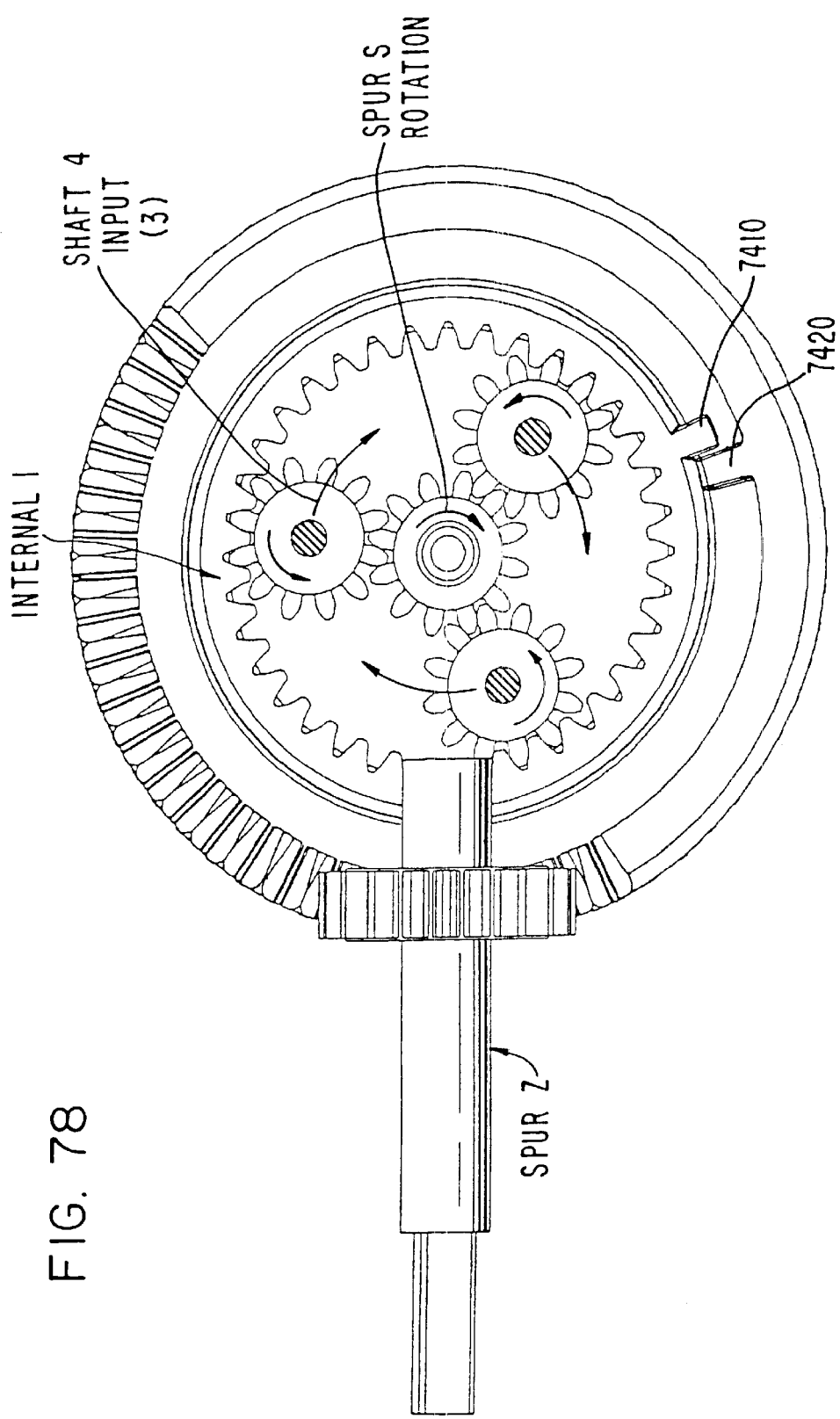
FIG. 78 shows a side view of an index-pitch adjustment mechanism, showing the motion of elements due to movement of the trigger from position B to position C and with the pitch amount at its minimum value, according to the preferred embodiment of the invention.

FIG. 78 is a similar view to FIG. 77, and shows the initial positioning of the gear Spur-Z with respect to the gear Face-Y, which causes minimum amount of indexing of the medical instrument 700. In the preferred embodiment, there are five possible index settings (5 mm, 7.5 mm, 10 mm, 12.5 mm, and 15 mm), with the minimum one being 5 mm, and with the maximum one being 15 mm. FIG. 77 shows the initial positioning of the gear Spur-Z with respect to the gear Face-Y, which causes the maximum amount of indexing of the medical instrument 700. The indexing difference is a result of the positioning of the stop of the gear Face-Y, whereby the earlier the stop of gear internal-1 comes into contact with the stop of the gear Face-Y (as the trigger 180 is moved from position B to position C), the more indexing will result (since gear internal-1 will stop its rotation as soon as the stops 7410, 7420 hit each other and thereby urge the sun gear Spur-S to move clockwise).

In FIG. 77, the gear Spur-Z is shown at one end of teeth portion 7710 of gear Face-Y, so as to provide for maximum indexing of the medical instrument 700. In FIG. 78, the gear Spur-Z is shown at the other end of the teeth portion 7710 of gear Face-Y, so as to provide for minimum indexing of the medical instrument 700.

Figure 59:
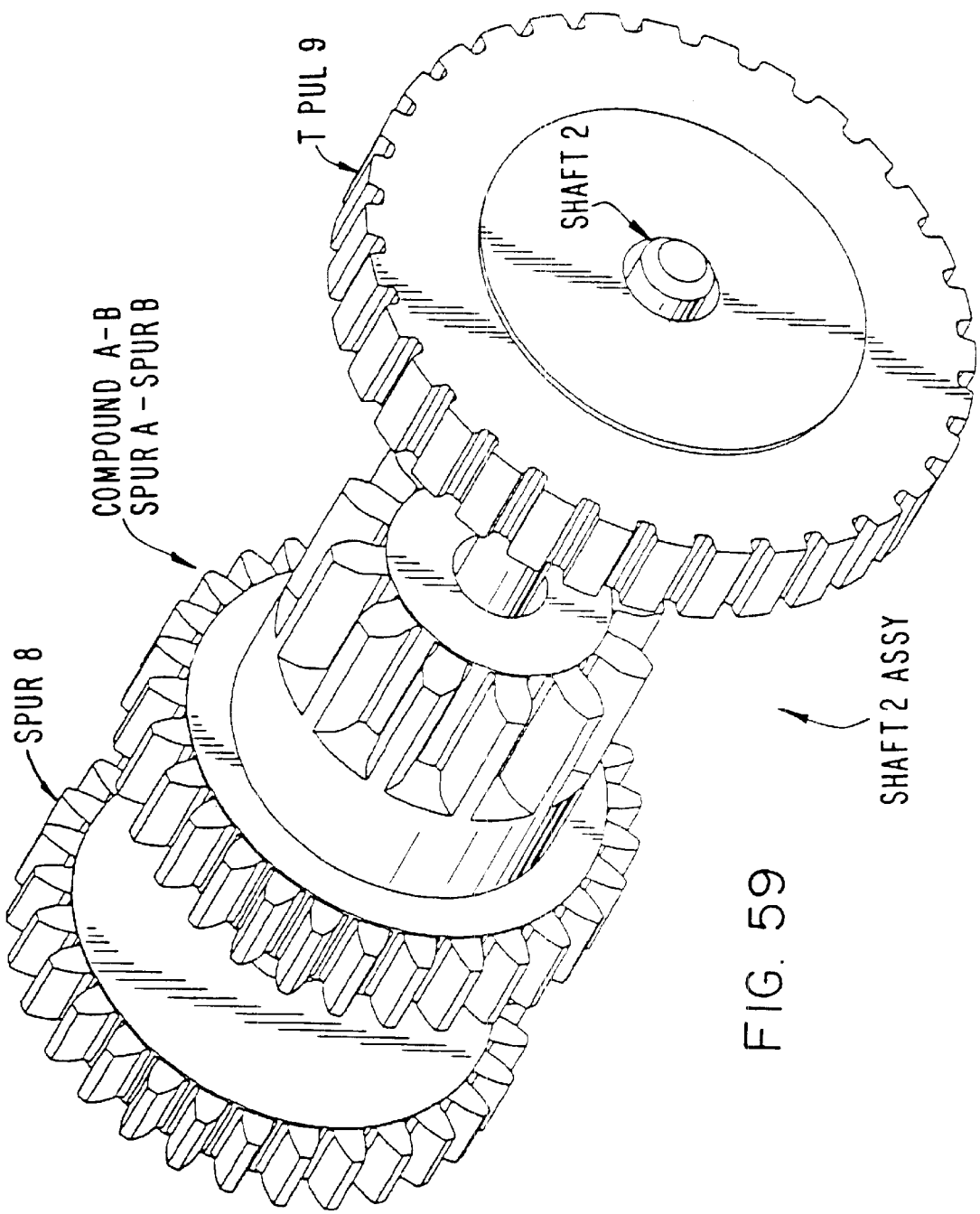
FIG. 59 is a view of the elements of the shaft#2 assembly of the drive train assembly, according to the preferred embodiment of the invention.

The shaft#2 assembly is shown in FIG. 59. These elements cause rotation of the drive belt 2530. As explained above, the drive rack 2570 causes rotation of compound gear A-B, which, through various other gears, causes rotation of gear Spur-8. Since gear Spur-8 and gear TPUL-9 are both registered with shaft#2 (but note that compound gear A-B is not registered with shaft#2), rotation of gear Spur-8 causes rotation of gear TPUL-9. Since the gear TPUL-9 is registered with the drive belt 2530, the drive belt 2530 rotates, thereby causing the stylet carriage assembly 2520 to move in a direction towards the distal end of the medical instrument 700.

Figure 60:
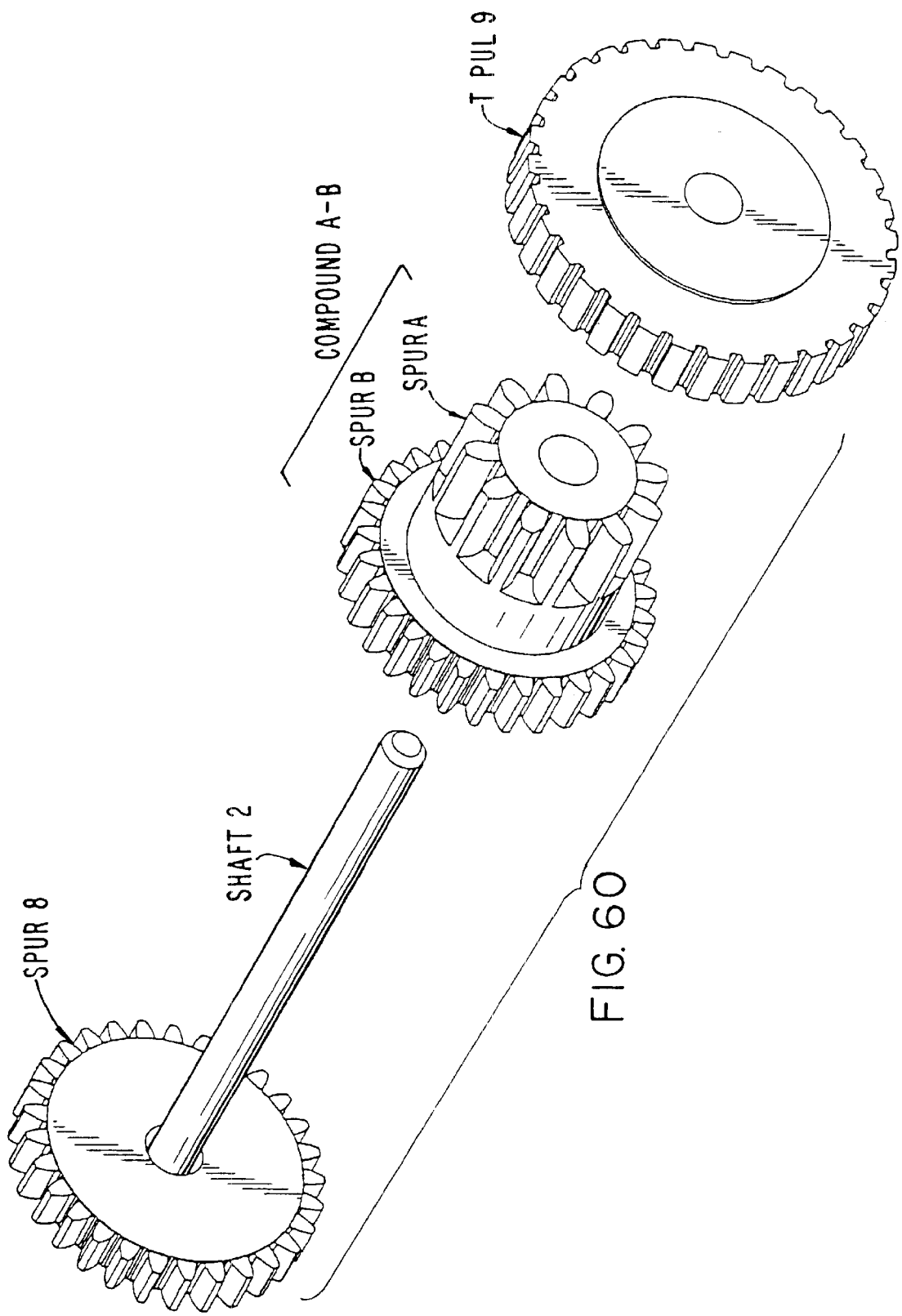
FIG. 60 is a fully exploded top perspective view of the shaft#2 assembly of the drive train assembly, according to the preferred embodiment of the invention.

FIG. 60 is an exploded view of the gears making up the shaft#2 assembly, whereby the compound gear A-B that includes gear Spur-B and gear Spur-A can be seen. Shaft#2 assembly includes gear Spur-8, compound gear Spur A-B, and gear TPUL-9.

Figure 61:
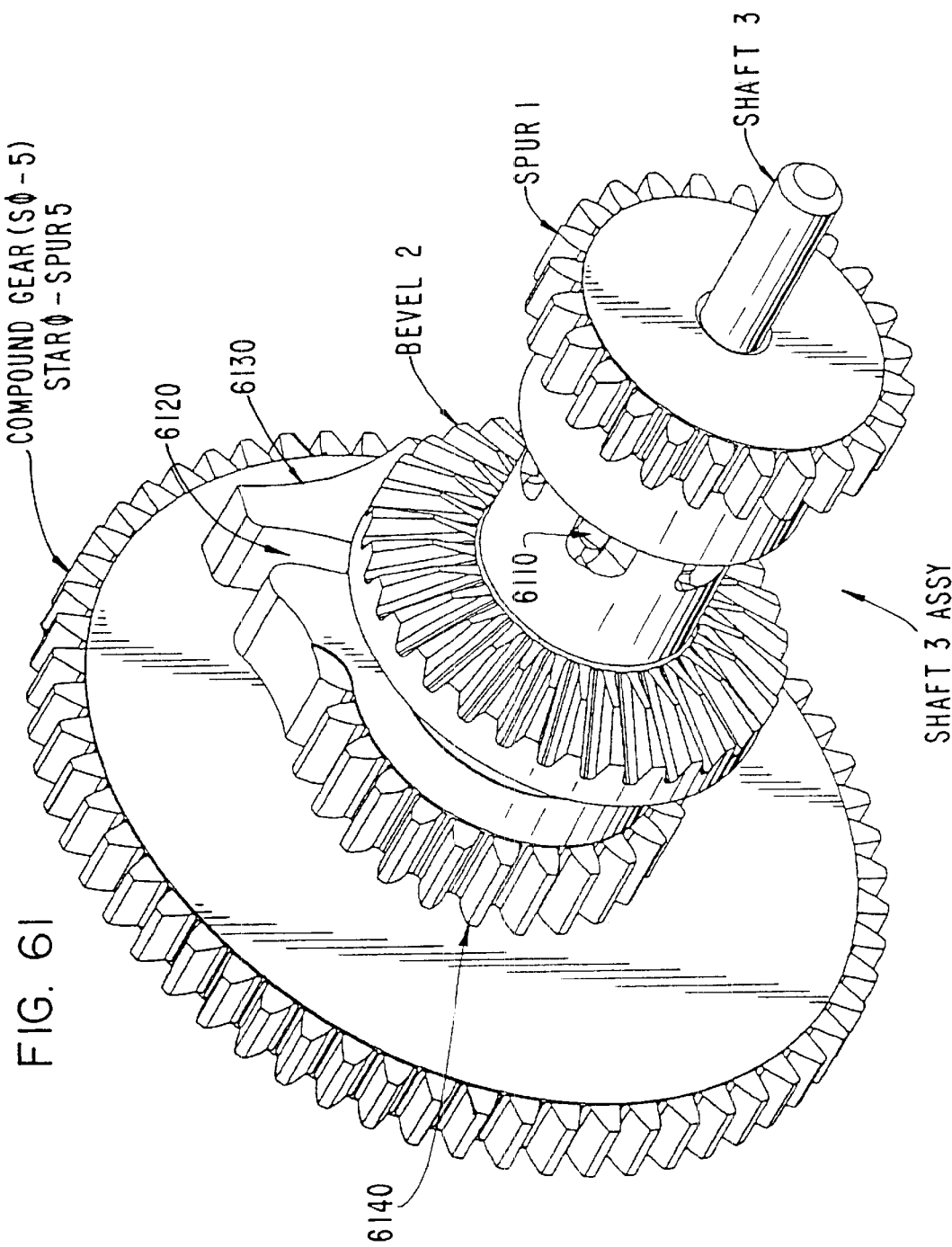
FIG. 61 is a view of the elements of the shaft#3 assembly of the drive train assembly, according to the preferred embodiment of the invention.

FIG. 61 is a perspective view of the shaft#3 assembly, which provides for indexing of the medical instrument 700. A clutch insert 6110 is provided in the shaft#3 assembly, to assure that the index lead screw 2540 is only rotated in one direction (when the trigger 180 moves from position B to position C), and not in the opposite direction (when the trigger 180 moves from position C to position B). FIG. 61 also shows the Star-0 cam 6130 and one of the Star-0 slots 6120, as well as the Star-0 gear segment 6140.

Figure 62:
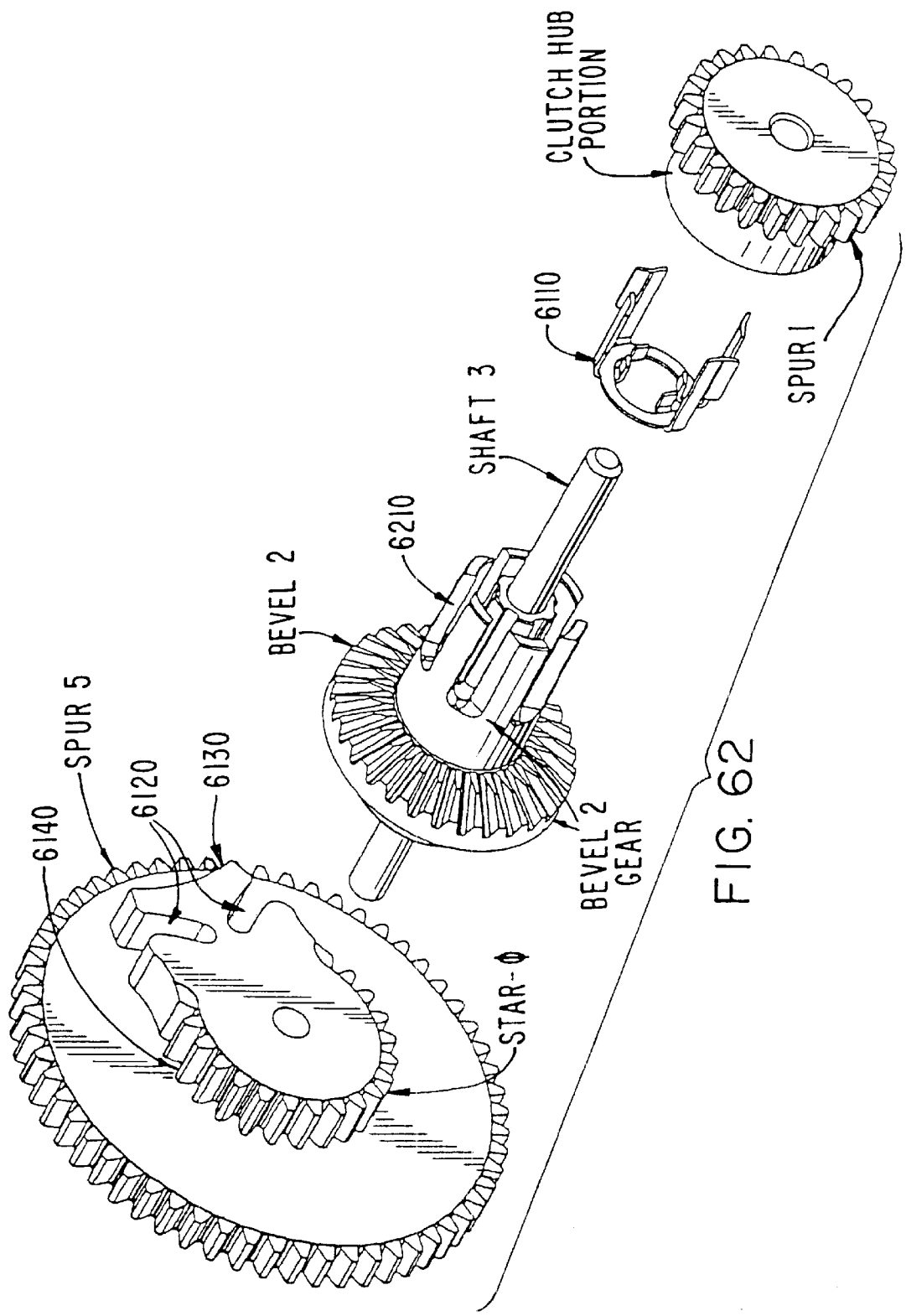
FIG. 62 is a fully exploded top perspective view of the shaft#3 assembly of the drive train assembly, according to the preferred embodiment of the invention.

FIG. 62 shows in exploded view form the various elements making up the shaft#3 assembly. The compound gear S0-5 is shown, and its movement that is used to provide stylet movement has been described previously. Also shown in FIG. 62 is the gear Bevel-2, which includes a clutch housing element 6210. Furthermore, FIG. 62 shows the clutch insert 6110 and a clutch hub portion (part of gear Spur-1), which form part of a clutch assembly used to provide one-way driving of the medical instrument 700.

Figure 63A:
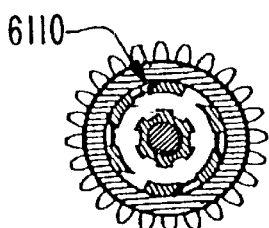
FIGS. 63A–D are different views (including section views) of the shaft#3 assembly of the drive train assembly, according to the preferred embodiment of the invention.
Figure 63B:
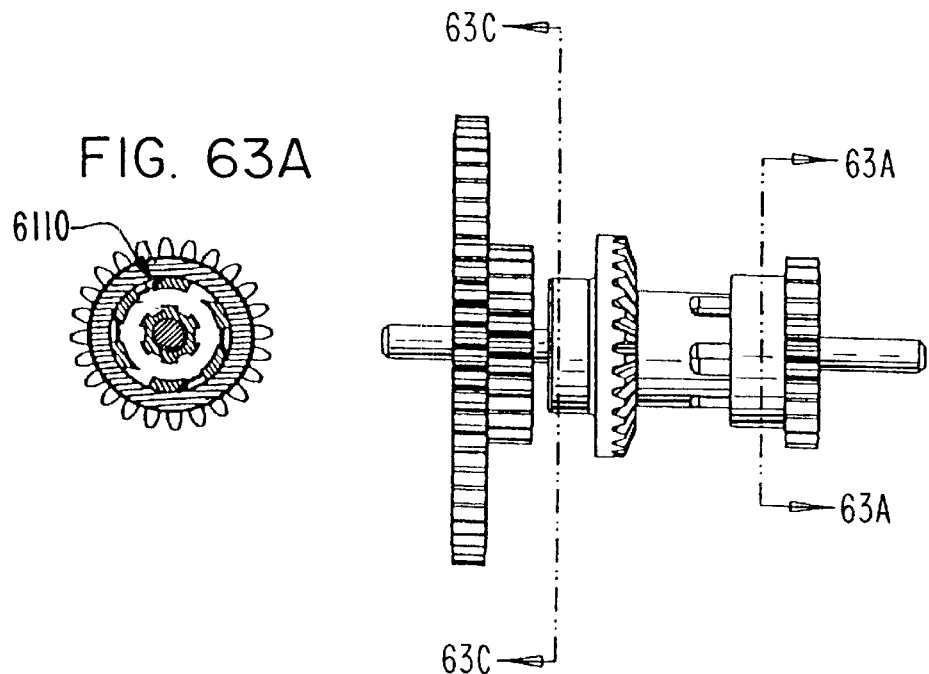
Figure 63C:
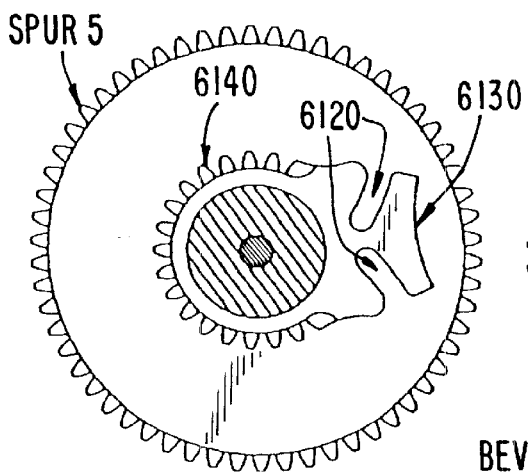
Figure 63D:
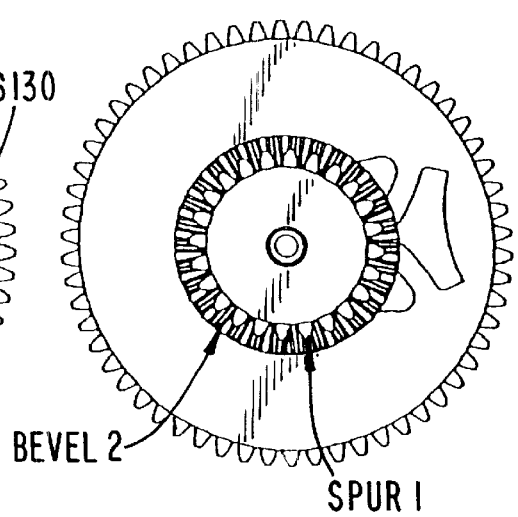
Figure 64:
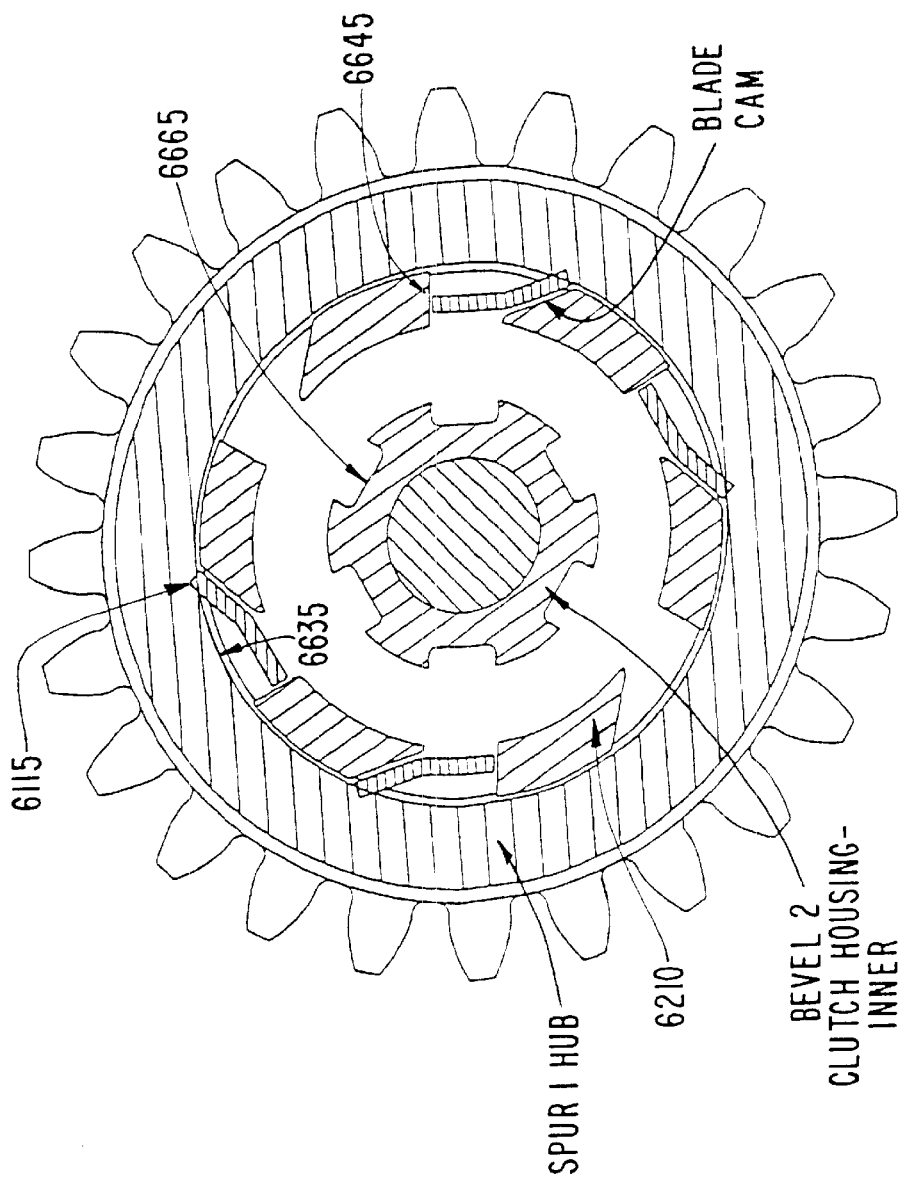
FIG. 64 is a blow-up of the section view of FIG. 63A, showing the clutch section.

FIG. 63B shows a side view of the elements making up the shaft#3 assembly, and FIG. 63D shows a view along the axis of the shaft#3. FIGS. 63A and 63C show two different cross sections of the shaft#3 assembly. FIG. 64 shows a blow-up of the section view shown in FIG. 63A.

Figure 65:
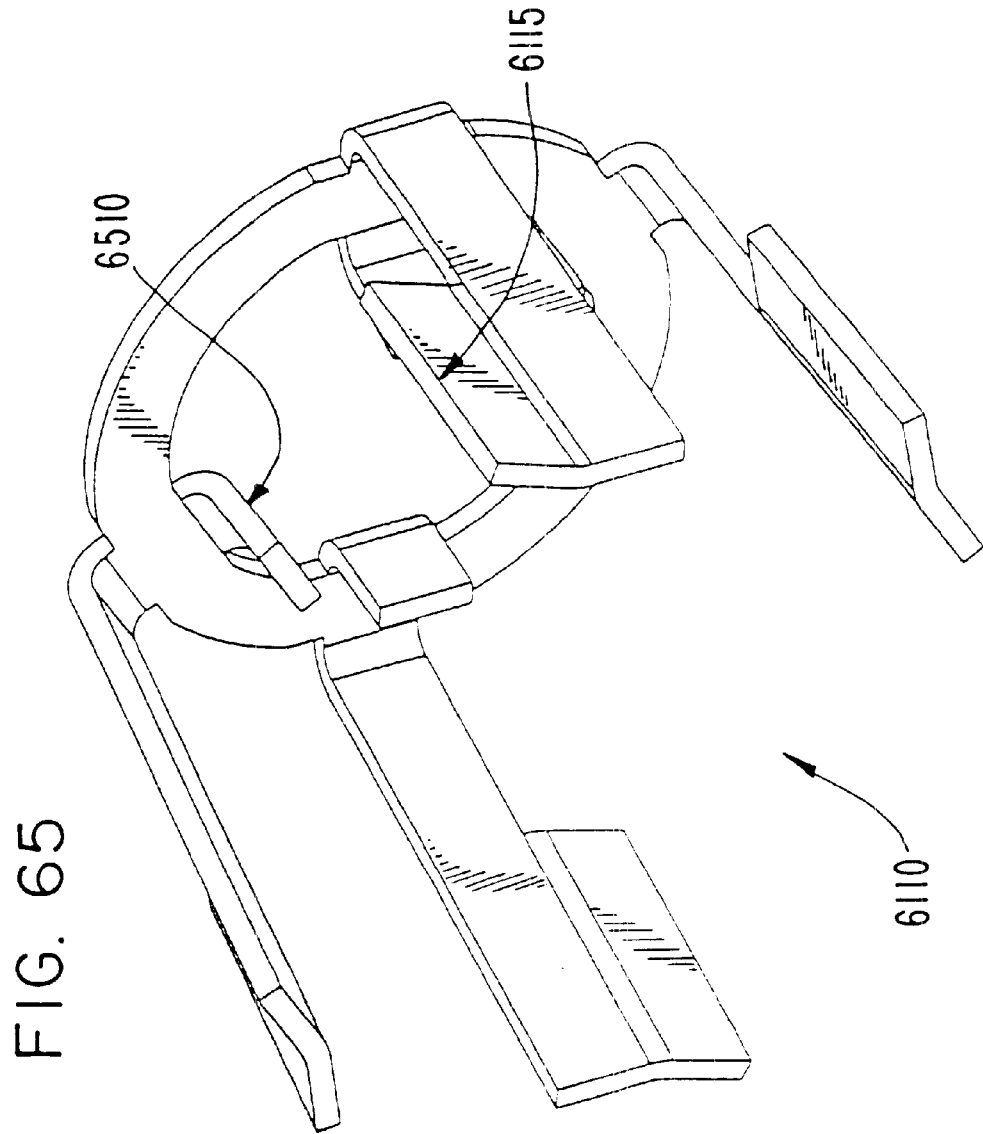
FIG. 65 shows a clutch insert of the clutch section, according to the preferred embodiment of the invention.

FIG. 65 shows a blow-up view of the clutch insert 6110. The clutch insert 6110 is preferably a sheet metal part with tangs extending from one side of it. The tangs have sharp edges in the preferred construction. The clutch hub portion of gear Spur-1 is preferably a plastic part, and the tangs of the clutch insert 6110 either dig into it or ride along it.

Figure 66:
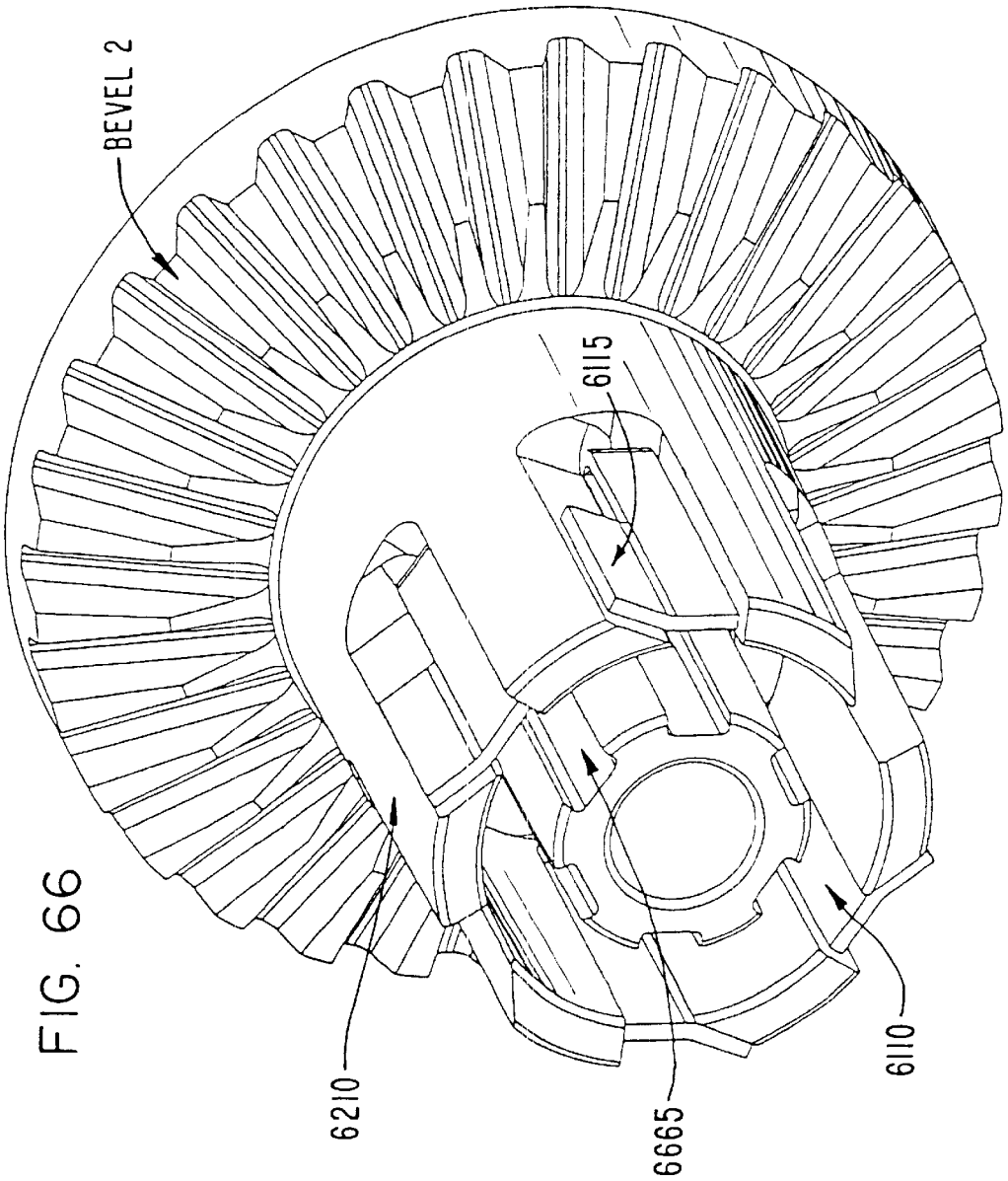
FIG. 66 is a perspective view of the bevel-2 gear with the clutch insert, according to the preferred embodiment of the invention.
Figure 67:
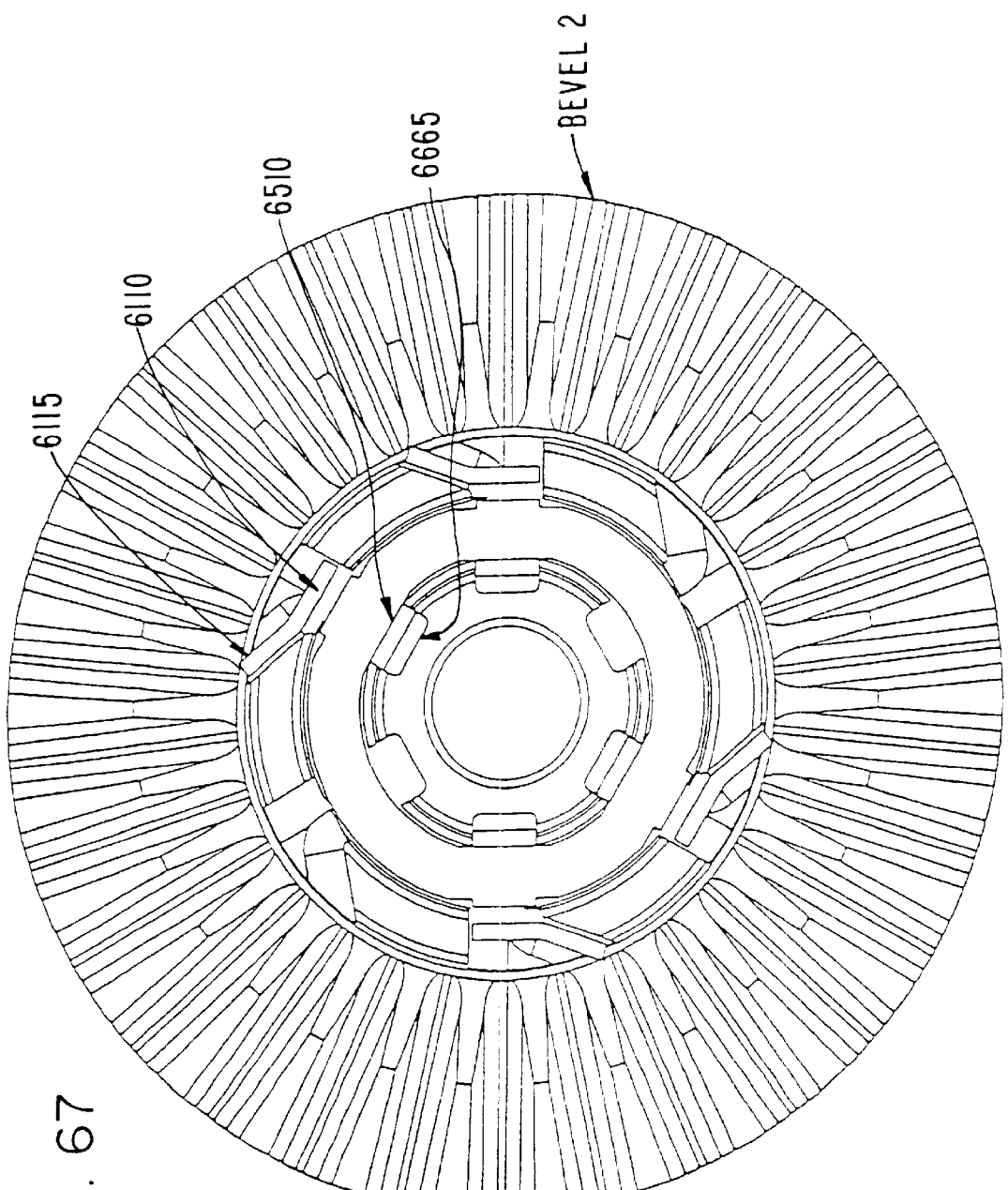
FIG. 67 is a side view of the bevel-2 gear with the clutch insert, according to the preferred embodiment of the invention.

The tangs of the clutch insert 6110 are engaged or held in place by respective slots of the clutch housing 6210. FIGS. 64, 66 and 67 show this engagement in different views of the clutch assembly according to the invention.

Referring back to FIG. 65, the clutch insert 6110 has a set of tangs on its inner diameter, which are referred to as clutch locating tabs 6510. The clutch locating tabs 6510 are fitted within clutch insert locating recesses 6665 of the clutch housing 6210, as seen best in FIGS. 66 and 67. The clutch blades 6115 are sprung outward and cause an initial compressive force on the surface Spur-1 Hub inside diameter 6635 when assembled.

When the hub of gear Spur-1 rotates counterclockwise, the clutch blades 6115 of the clutch insert 6110 drag and slide along the Spur-1 Hub inside diameter 6635. Since the clutch blades are able to move inward radial against the compressive force, minimal tangential forces are imparted on the clutch housing 6210, and the gear Bevel-2 is not able to rotate.

When the hub of gear Spur-1 rotates clockwise, the clutch blades 6115 catch and bite into the Spur-1 Hub inside diameter 6635 because the blades become wedged against the clutch blade backstop 6645 located on the outer clutch housing 6210 that is adjacent each clutch blade 6115. The Spur-1 Hub is preferably made from a relatively soft plastic. Wedging of the clutch blade insert between the Spur-1 Hub and the clutch housing causes direct engagement of the Spur-1 Hub and the clutch housing resulting in rotation of gear Bevel-2 in the counterclockwise direction.

The rotation of sun gear Spur-S (see FIG. 57) provides the impetus for causing rotation of gear Bevel-2, and the clutch assembly described above only allows the gear Bevel-2, and thus the index lead screw 2540 (indirectly coupled to the gear Bevel-2), to rotate in only one direction. Thus, in this configuration, the medical instrument 700 can only be indexed to move in a direction away from the patient's body between seed implant locations. To move the medical instrument 700 inwards into the patient's body, the nut box assembly 2550 has to first be disengaged from the index lead screw 2540 by actuating sheath button 791. Following the release of the sheath button, the medical instrument 700 can be physically repositioned either towards or away from the patient's body.

Referring now to FIG. 67, as shown in that figure, each of the clutch blades of the clutch insert 6110 are shown having a shallow V-shape, whereby one part (the left part) of the clutch blade sticks out slightly from the outer surface of the clutch housing. The clutch assembly according to the invention allows the gear Bevel-2 to rotate in one direction, but not in the other direction.

Figure 68:
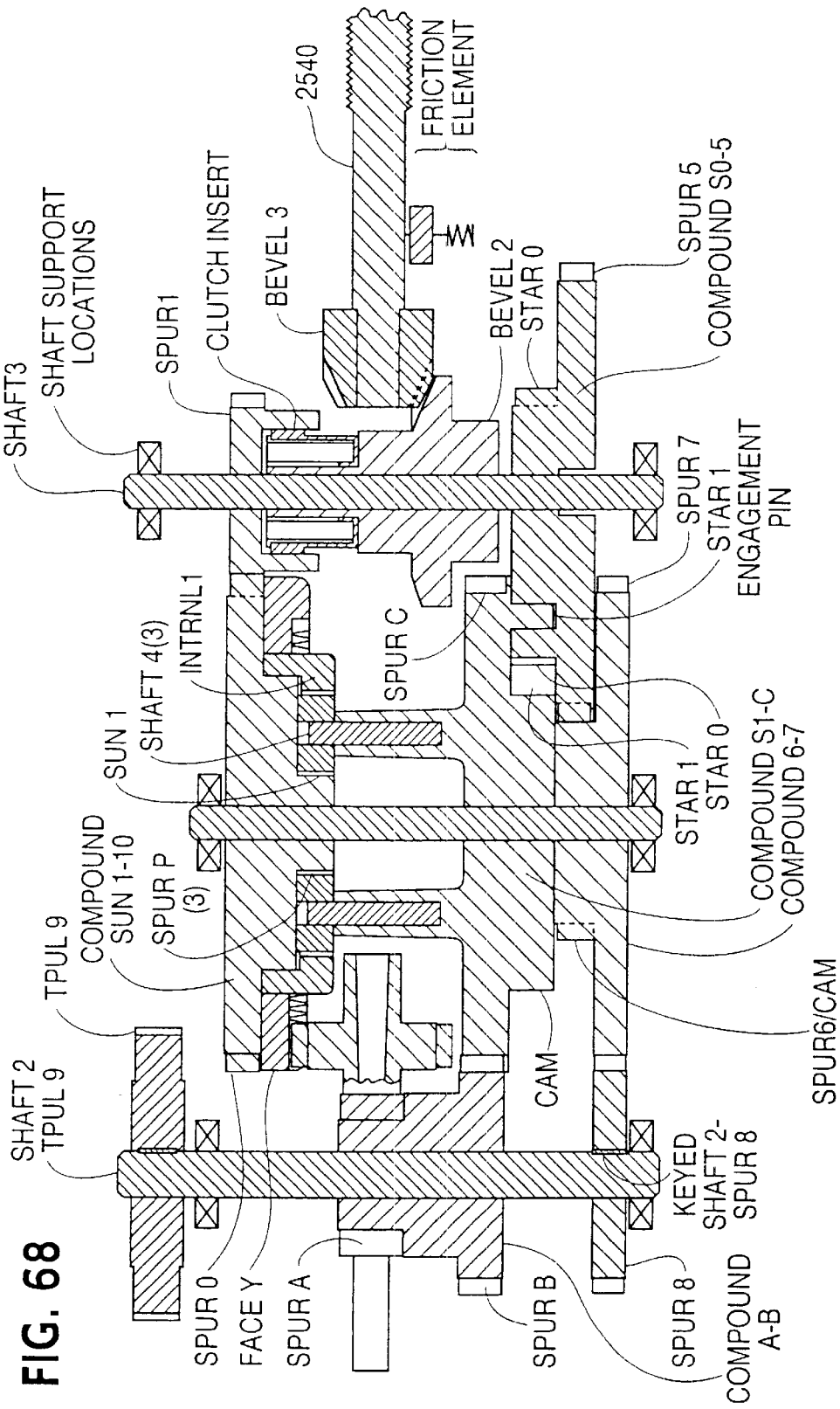
FIG. 68 is a drive train schematic component section view, according to the preferred embodiment of the invention.
Figure 69:
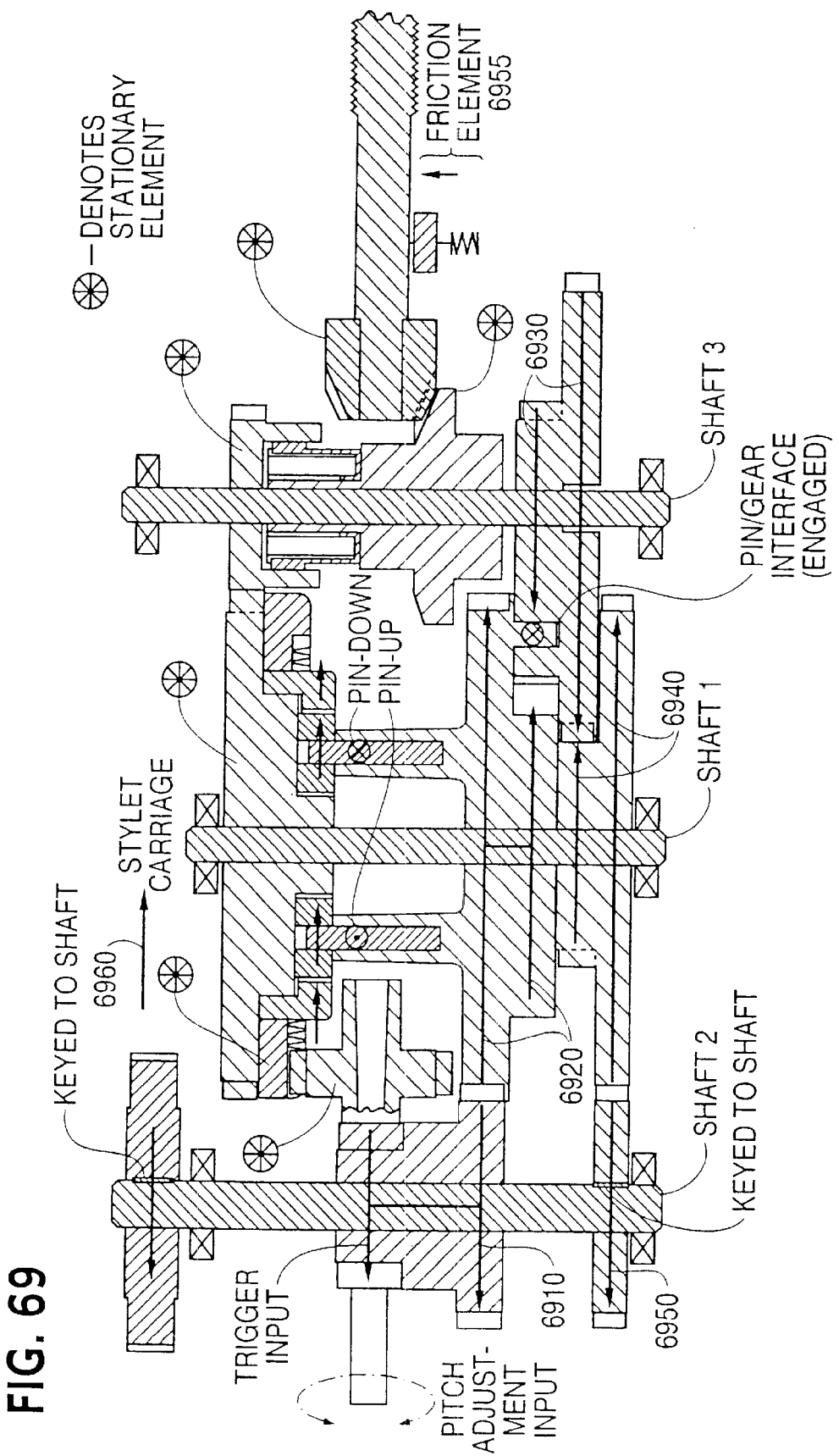
FIG. 69 is a drive train schematic component section view, showing the rotation of gears to cause stylet motion (due to movement of the trigger from position A to position B), according to the preferred embodiment of the invention.

FIG. 68 is a schematic component diagram that shows the disposition of the various gears making up the drive train assembly 2510. FIG. 69 is a schematic component diagram with arrows that denote the rotation direction of the respective gears of the drive train assembly 2510, as a result of movement of the trigger 180 from position A to position B (same view as in FIG. 68). The movement results in motion of the stylet 2410 only, and does not result in indexing of the medical instrument 700.

FIG. 69 also shows the pitch adjustment input, via rotation of the pitch adjustment knob 170 (see FIG. 1 also). The pitch adjustment can only be made prior to actuation of the trigger 180.

When the trigger 180 is moved from position A to position B, the drive rack 2570 moves in a direction towards the proximal end of the medical instrument 700. This movement of the drive rack 2570 results in the compound gear Spur A-B, which is engaged with the teeth of the drive rack 2570 to rotate in a counterclockwise direction (when viewed from the left side of the medical instrument 700 as given in FIG. 69), as shown by the double arrows 6910 connected together by a straight line in FIG. 69. This counterclockwise rotation of compound gear Spur A-B results in compound gear S1-C to rotate in a clockwise direction, as shown by the double arrows 6920 connected by a straight line in FIG. 69.

The clockwise rotation of compound gear S1-C results in compound gear S0-5 to rotate counterclockwise (see also FIGS. 74A to 74F for the precise movement of gear Star-0 with respect to gear Star-1), as shown by the two arrows 6930 in FIG. 69.

The counterclockwise rotation of compound gear S6-7 results in compound gear S6-7 to rotate clockwise, as shown by the arrows 6940 in FIG. 69.

The clockwise rotation of compound gear S6-7 results in gear Spur-8 to rotate counterclockwise, as shown by the arrow 6950 in FIG. 69. Since gear Spur-8 and since gear TPUL9 are both keyed to shaft#2, clockwise rotation of gear Spur-8 results in clockwise rotation of gear TPUL-9. Since gear TPUL-9 is registered with the drive belt 2530, the drive belt 2530 moves, thereby resulting in the stylet carriage assembly 2520 (and thus the stylet 2410) moving in a distal direction within the medical instrument 700, as shown by arrow 6960.

FIG. 69 also shows the clockwise rotation of planetary gears Spur-P, as well as the clockwise rotation of the pins that are coupled to the planetary gears Spur-P (the pins rotating since in this manner since they are coupled to compound gear S1-C). FIG. 69 further shows a friction element 6955 coupled to the index lead screw 2540, which is indirectly coupled to the sun gear Spur-S. Due to this friction element 6955 (downstream elements from the sun gear Spur-S, including the index lead screw 2540), sun gear Spur-S does not rotate based on the rotation of planetary gears Spur-P. However, the gear internal-1 does rotate until its stop 7510 makes contact with the stop 7520 of the gear Face-Y (see FIGS. 76 and 77 also).

Figure 70:
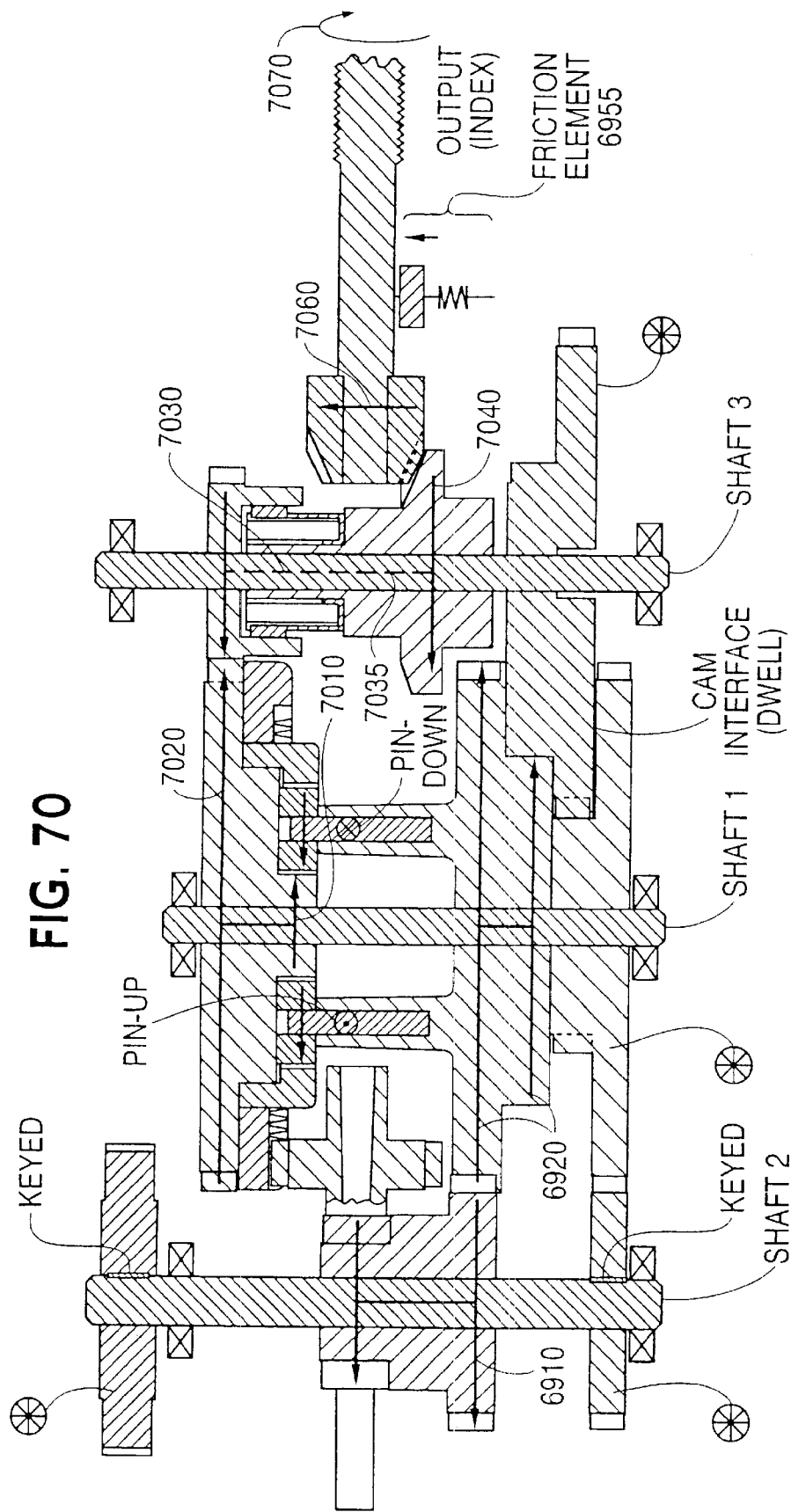
FIG. 70 is a drive train schematic component section view, showing the rotation of gears to cause index motion (due to movement of the trigger from position B to position C), according to the preferred embodiment of the invention.
Figure 71:
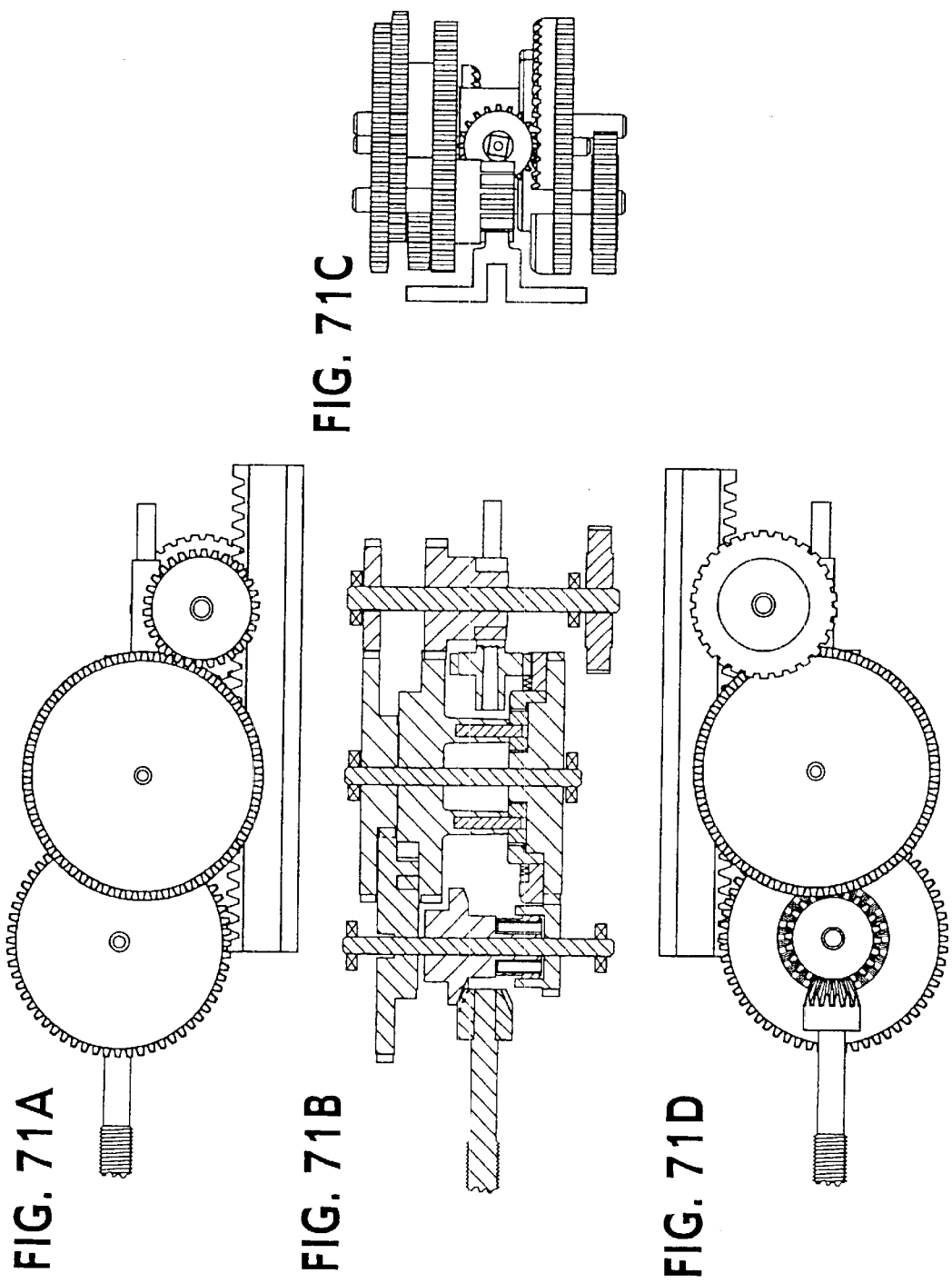
FIGS. 71A–D show additional views of the drive train assembly, according to the preferred embodiment of the invention.

FIG. 70 is a schematic component diagram with arrows denoting the rotation direction of the gears of the drive train assembly 2510, as a result of movement of the trigger 180 from position B to position C (same view as in FIG. 68). This movement of the trigger 180 results in indexing of the medical instrument 700, whereby the stylet 2410 remains at its most-distal position within the medical instrument 700.

The planetary gears Spur-P rotate in a counterclockwise direction (see also FIG. 77), since the stop 7510 of gear internal-1 has hit the stop 7520 on gear Face-Y. This results in sun gear Spur-S rotating in a clockwise direction, as seen by the arrow 7010 in FIG. 70, whereby it rotates since the friction element (that had prevented it from moving as the trigger 180 was moved from position A to position B) has been overcome. The friction element 6955 may be on the index lead screw 2420 or on gear Spur-1 or on gear Bevel-2, or on any combination of these elements.

Since sun gear Spur-S is part of compound gear Sun 1-0 (see also FIG. 57), gear Spur-0 also rotates in a clockwise direction, as shown by arrow 7020.

The clockwise rotation of gear Spur-0 results in the counterclockwise rotation of gear Spur-1, as shown by arrow 7030. Gear Spur-1 is coupled, via a clutch assembly (see dashed arrow 7035 in FIG. 70) to gear Bevel-2, whereby clockwise rotation of gear Spur-1 results in clockwise rotation of gear Bevel-2 (the clutch assembly prevents counterclockwise rotation of gear Spur-1 from causing any rotation of gear Bevel-2), as seen by the arrow 7040 in FIG. 70. Note that, due to the clutch assembly, when the trigger 180 is released, whereby it moves from position C back to position B and then to its home position A, the clutch assembly prevents the index lead screw 2540 from rotating during that time.

The clockwise rotation of gear Bevel-2 results in clockwise rotation of gear Bevel-3 (as viewed from the back of the medical instrument 700), as shown by arrow 7060, which in turn results in clockwise rotation of the index lead screw 2540, as shown by arrow 7070. The rotation of the index lead screw 2540 results in movement of the nut box assembly 2550 to a more distal position on the medical instrument 700, thereby resulting in the medical instrument 700 indexing away from the patient's body, to be positioned for a next seed implant location in the patient's body.

Figure 72:
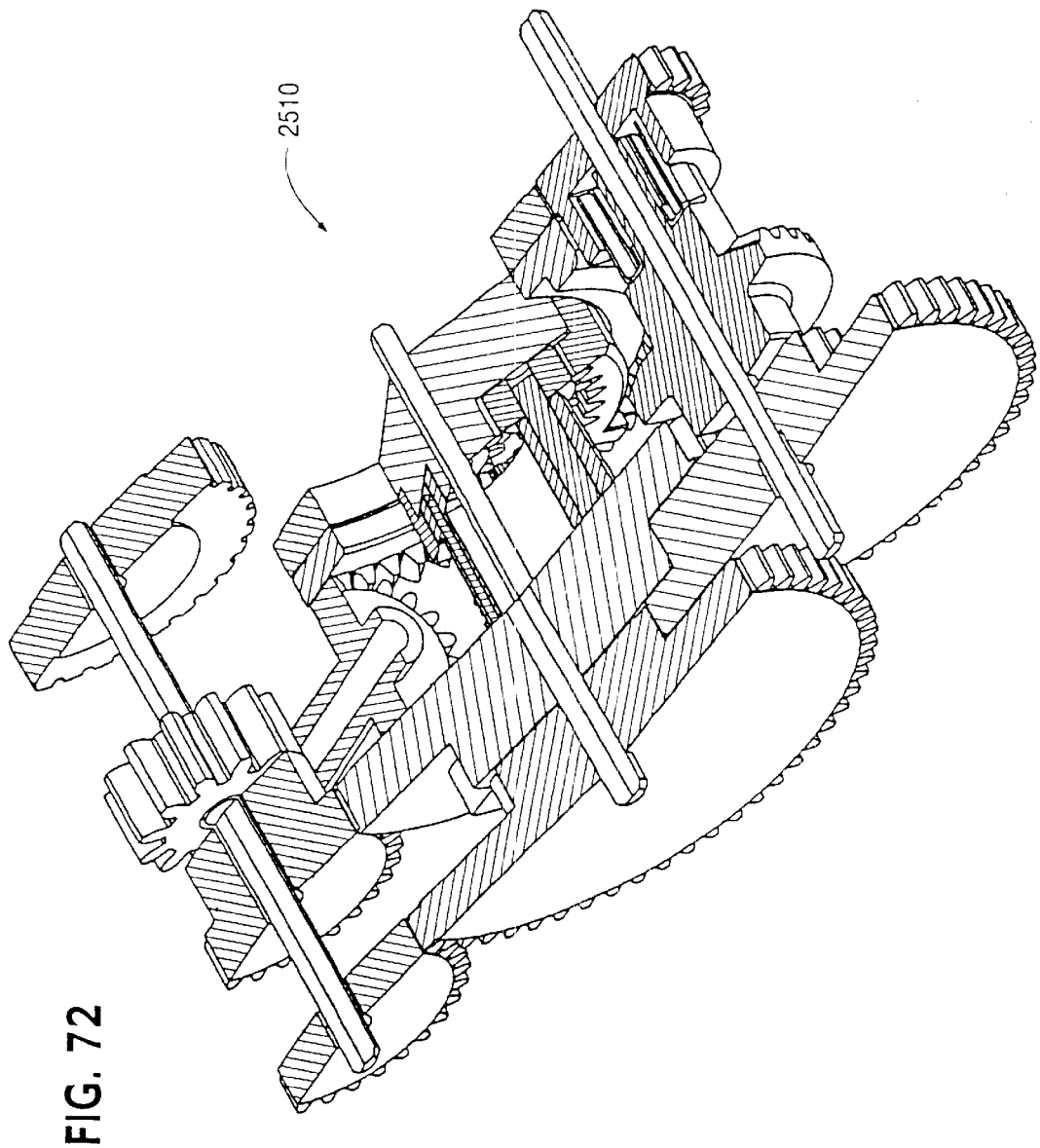
FIG. 72 shows a first ISO multi-level section view of the drive train assembly, according to the preferred embodiment of the invention.
Figure 73:
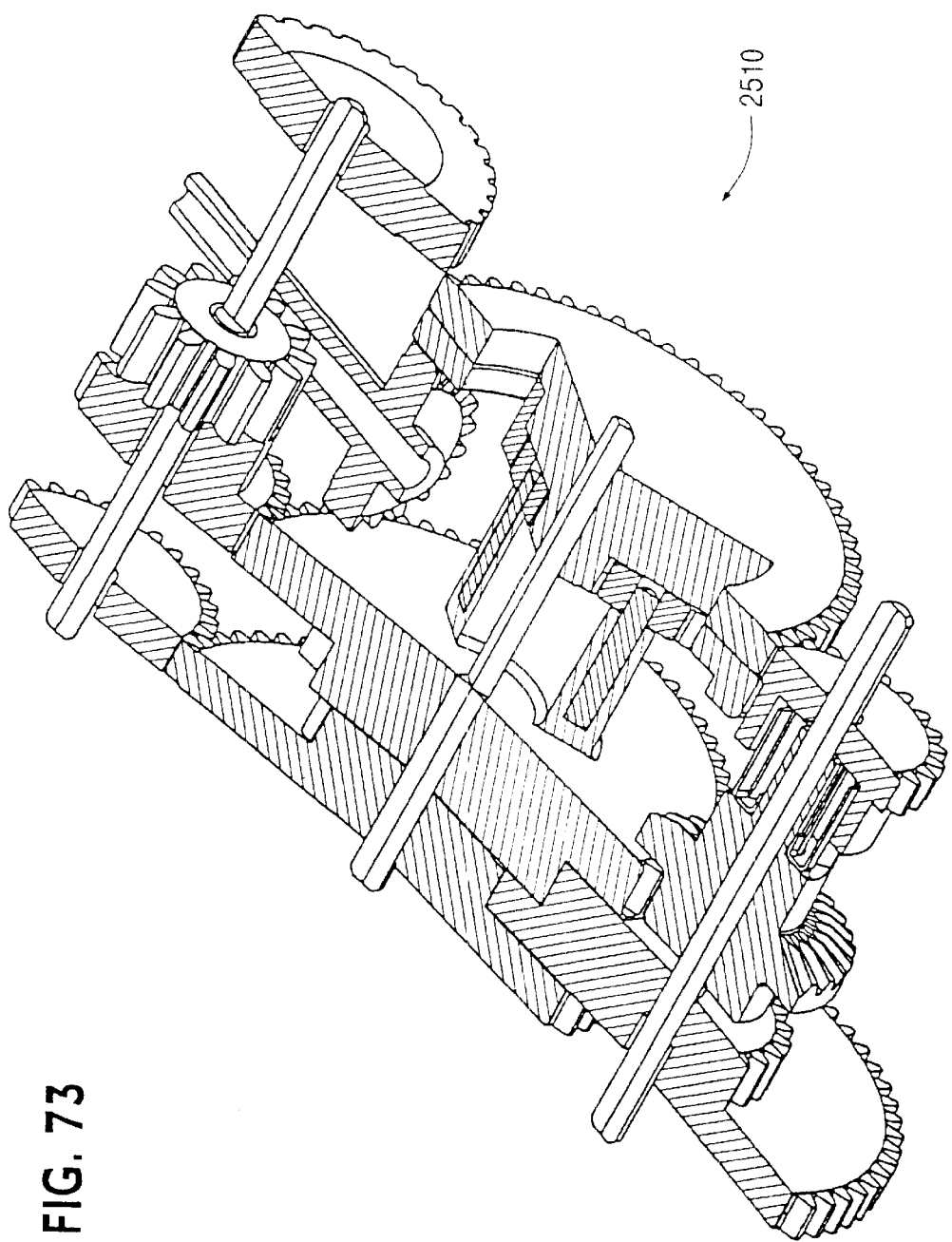
FIG. 73 shows a second ISO multi-level section view of the drive train assembly, according to the preferred embodiment of the invention.

FIGS. 71A through 71D show views from different directions of the drive trains assembly 2510, and FIGS. 72 and 73 show different multi-level section views of the drive train assembly 2510.

While the above components are described with respect to the preferred embodiment, other similar types of components may be utilized, while remaining within the spirit and scope of the present invention, as exemplified by the claims. For example, other types of medical procedures using implantation devices, whether they be seeds or other things, and whether they are for treating prostate cancer or something else, may be utilized based on the teachings provided above. For example, while the embodiments described above are with respect to a specific drive train assembly, one of ordinary skill in the art will recognize that other types of drive train assemblies may be contemplated, which perform the functions needed to move the stylet forward when the trigger 180 is moved from position A to position B, and to index the medical instrument 700 when the trigger 180 is moved from position B to position C.

Other applications for driving an instrument a precise amount based on operator input can also be envisioned by use of the drive mechanism according to the present invention, such as a machining operation in a manufacturing plant, for example, or any other industrial or commercial application. The present invention provides for a drive mechanism that has two inputs, A and B, and that provides two outputs C and D, whereby output C is modified by input B, and whereby input A drives output C and output D, and whereby output C dwells during output D movement.

As an alternative configuration of the medical instrument described above, the stylet may be configured to provide optics to assist in a seed implantation procedure. In that case, the stylet operates as a seed pusher and a light and image providing device, whereby the stylet carries optical fibers to provide the light and imaging capability to the seed implantation location.

What is claimed is:

1. A medical instrument comprising: a coupling portion for coupling to a needle cannula; and a stylet that is provided within a housing of the medical instrument and that is configured to move from a rest position to an engaged position, to thereby propel a seed obtained from a cartridge within the medical instrument into a distal end of the needle cannula;
    a drive belt; and a stylet carriage assembly, wherein the stylet carriage assembly is coupled to the stylet, and wherein the stylet moves to the distal end of the needle cannula due to the drive belt being driven; further comprising a trigger wherein actuation of the trigger will cause the medical instrument to index to a next seed implant position within a patient.

2. A method for implanting at least one seed into a patient, comprising:
    a) actuating a trigger of a medical instrument from a first position to a second position, to thereby cause a seed to be placed at a distal end of a needle coupled to the medical instrument;
    b) as a result of the actuating in step a), moving a stylet within the medical instrument from a first position to a second position, whereby the stylet is moved from a proximal position within the medical instrument to a distal position within the medical instrument, and whereby the stylet pushes a seed to the distal end of the needle coupled to the medical instrument as a result;
    c) actuating the trigger of the medical instrument from the second position to a third position, to thereby cause the medical instrument to index to a next seed implant location within the patient; and
    d) causing a drive screw within the medical instrument to rotate in one direction,
    wherein a nut box assembly is coupled to the drive screw and engages with threads on the drive screw,
    wherein the medical instrument is coupled to a targeting fixture by way of the nut box assembly, to thereby provide a fixed position with respect to the patient, and
    wherein, as the drive screw rotates in step d), the nut box assembly moves distally within the medical instrument, thereby causing the medical instrument to index away from the patient to the next seed implant location.

3. The method according to claim 2, further comprising spinning a needle cannula while the medical instrument is indexed.

4. A drive mechanism for a medical instrument, comprising:
    at least one gear that causes index movement of the medical instrument in accordance with operator-actuation of a trigger on the medical instrument;
    wherein a drive screw within the medical instrument rotates in one direction in accordance with said at least one gear;
    wherein a nut box assembly is coupled to the drive screw and engages with threads on the drive screw;
    wherein, as the drive screw rotates, the nut box assembly moves distally within the medical instrument, thereby causing the medical instrument to index away from a patient.

* * * * *